(12) United States Patent
Nagy et al.

(10) Patent No.: US 9,119,834 B2
(45) Date of Patent: Sep. 1, 2015

(54) NON-PATHOGENIC SEROTYPE 4 FOWL ADENOVIRUS (FADV-4) AND VIRAL VECTOR THEREOF

(75) Inventors: Éva Nagy, Guelph (CA); Bryan Griffin, Guelph (CA); Helena Grgic, Guelph (CA); Davor Ojkic, Guelph (CA)

(73) Assignee: University of Guelph, Guelph, ON (CA)

( * ) Notice: Subject to any disclaimer, the term of this patent is extended or adjusted under 35 U.S.C. 154(b) by 57 days.

(21) Appl. No.: 14/005,380

(22) PCT Filed: Mar. 16, 2012

(86) PCT No.: PCT/CA2012/000238
§ 371 (c)(1),
(2), (4) Date: Sep. 16, 2013

(87) PCT Pub. No.: WO2012/129645
PCT Pub. Date: Oct. 4, 2012

(65) Prior Publication Data
US 2014/0010834 A1    Jan. 9, 2014

Related U.S. Application Data

(60) Provisional application No. 61/453,297, filed on Mar. 16, 2011.

(51) Int. Cl.
*A61K 39/235* (2006.01)
*C12N 7/02* (2006.01)
*C12N 15/861* (2006.01)
*A61K 39/00* (2006.01)

(52) U.S. Cl.
CPC .............. *A61K 39/235* (2013.01); *C12N 7/02* (2013.01); *C12N 15/861* (2013.01); *A61K 2039/552* (2013.01); *C12N 2710/10221* (2013.01); *C12N 2710/10234* (2013.01); *C12N 2710/10243* (2013.01)

(58) Field of Classification Search
None
See application file for complete search history.

(56) References Cited

U.S. PATENT DOCUMENTS

| 6,296,852 | B1 | 10/2001 | Johnson et al. | |
|---|---|---|---|---|
| 2010/0150958 | A1 | 6/2010 | Sheppard | |
| 2010/0158939 | A1 | 6/2010 | Sambhara et al. | |
| 2014/0010834 | A1* | 1/2014 | Nagy et al. | 424/186.1 |

FOREIGN PATENT DOCUMENTS

WO        03/039593 A1    5/2003

OTHER PUBLICATIONS sequence alignment of instant SEQ ID No.: 2 with GenEmbl access No. EF458161 Feb. 27, 2007.*

Davison, A. J., et al. "The human cytomegalovirus genome revisited: comparison with the chimpanzee cytomegalovirus genome." J Gen Virol, 2003b, 84, 17-28.
Broker, T., "Animal Virus RNA Processing. In Processing of RNA." pp. 181-212. Edited by D. Apirion. Boca Raton, Florida: CRC Press, Inc., 1984.
Reddy, P. S., et al. "Characterization of early region 1 and pIX of bovine adenovirus-3." Virology, 1999, 253, 299-308.
Zheng, B. J., et al. "Transcription units of E1a, E1b and pIX regions of bovine adenovirus type 3." J Gen Virol, 1999, 80, 1735-1742.
Perricaudet, M., et al. "Structure of two spliced mRNAs from the transforming region of human subgroup C adenoviruses." Nature, 1979, 281, 694-696.
Virtanen, A., et al. "mRNAs from human adenovirus-2 early region 4." J Virol, 1984, vol. 51, No. 3, 822-831.
Wold, W. S. M., et al. "Mapping a new gene that encodes an 11,600-molecular-weight protein in the E3 transcription unit of adenovirus-2." J Virol., 1984, vol. 52, No. 2, 307-313.
Griffin, B.D. and Nagy, E., "Coding potential and transcript analysis of fowl adenovirus 4: insight into upstream ORFs as common sequence features in adenoviral transcripts." Journal of General Virology, Jun. 2011, vol. 92, pp. 1260-1272.
Smith, R.R. et al., "Studies on the use of viruses in the treatment of carcinoma of the cervix." Cancer, 1956, vol. 9, No. 6, 1211-1218.
Cody, J.J. and Douglas, J.T., "Armed replicating adenoviruses for cancer virotherapy." Cancer Gene Ther., 2009, 16, 473-488.
Yamamoto, M. and Curiel, D.T., "Current issues and future directions of oncolytic adenoviruses." Mol Ther., 2010, vol. 18, No. 2, 243-250.
Lasaro, M.O. and Ertl, H.C.J."New Insights on Adenovirus as Vaccine Vectors." Molecular Therapy, 2009, vol. 17, No. 8, 1333-1339.
Buchbinder, S.P., et al., "Efficacy assessment of a cell-mediated immunity HIV-1 vaccine (the Step Study): a double-blind, randomised, placebo-controlled, test-of-concept trial." Lancet, 2008, vol. 372, Issue 9653, 1881-1893.
Mcelrath, M.J., et al. "HIV-1 vaccine-induced immunity in the test-of-concept Step Study: a case-cohort analysis." Lancet, 2008, vol. 372, Issue 9653, 1894-1905.
Gallo, P., et al., "Adenovirus as vehicle for anticancer genetic immunotherapy." Gene Ther., 2005, 12, S84-S91.
Shashkova, E.V., et al., "Avian adenovirus vector CELO-TK displays anticancer activity in human cancer cells and suppresses established murine melanoma tumors." Cancer Gene Ther, 2005, 12, 617-626.

(Continued)

*Primary Examiner* — Shanon A Foley
(74) *Attorney, Agent, or Firm* — Bereskin & Parr LLP/S.E.N.C.R.L., s.r.l.; I. Laurence MacPhie

(57) ABSTRACT

A high level replication fowl adenovirus (FAdV) isolate capable of reaching a viral titer of at least 3 log 10 is described. Said FAdV is a non-pathogenic strain of fowl adenovirus serotype 4, identified as FAdV-4 ON1. Additionally, the present disclosure also provides a viral vector comprising the fowl adenovirus, which has inserted an exogenous nucleotide sequence coding for at least one antigenic site of a disease of concern, as well as a method for obtaining said viral vector and an immunogenic composition comprising the same.

12 Claims, 9 Drawing Sheets

(56) References Cited

OTHER PUBLICATIONS

Barouch, D. H. "Challenges in the development of an HIV-1 vaccine." Nature, 2008, 455, 613-619.
Sharma, A., et al., "Evaluation of Cross-Reactive and Cell-Mediated Immune Responses among Human, Bovine and Porcine Adenoviruses." Gene Therapy, 2010, 17(5), 634-642.
Adair, B. and Fitzgerald, S. "Group I Adenovirus Infections." in Diseases of Poultry, 12th ed, 2008, pp. 252-266.
Benko, M., et al., "Family Adenoviridae." In Virus taxonomy Eighth report of the International Committee on the Taxonomy of Viruses, 2005, pp. 213-228.
Reddy, P. S., et al. "Nucleotide sequence, genome organization, and transcription map of bovine adenovirus type 3." J Virol, 1998, vol. 72, No. 2, 1394-1402.
Ojkic, D. and Nagy, E. "Antibody response and virus tissue distribution in chickens inoculated with wild-type and recombinant fowl adenoviruses." Vaccine, 2003, 22, 42-48.
Francois, A., et al., "Avian adenovirus CELO recombinants expressing VP2 of infectious bursal disease virus induce protection against bursal disease in chickens." Vaccine, 2004, 22, 2351-2360.
Sheppard, M., et al., "Fowl adenovirus recombinant expressing VP2 of infectious bursal disease virus induces protective immunity against bursal disease." Arch Virol, 1998, 143, 915-930.
Johnson, M.A., et al., "A recombinant fowl adenovirus expressing the S1 gene of infectious bronchitis virus protects against challenge with infectious bronchitis virus." Vaccine, 2003, vol. 21, 2730-2736.
Chiocca, S., et al. "The complete DNA sequence and genomic organization of the avian adenovirus CELO." J Virol., 1996, vol. 70, No. 5, 2939-2949.
Ojkic, D. & Nagy, E. "The complete nucleotide sequence of fowl adenovirus type 8." J Gen Virol., 2000, 81, 1833-1837.
Corredor, J. C., et al., "Sequence comparison of the right end of fowl adenovirus genomes." Virus Genes, 2008, 36,331-344.
Corredor, J.C., et al., "Sequence analysis of the left end of fowl adenovirus genomes." Virus Genes, 2006, 33, 95-106.
Bangari, D.S. and Mittal, S.K., "Development of nonhuman adenoviruses as vaccine vectors." Vaccine, 2006, 24, 849-862.
Ferreira, T. B., et al., "Use of adenoviral vectors as veterinary vaccines." Gene Ther., 2005, 12, S73-S83.
Corredor, J. C. and Nagy, E., "A region at the left end of the fowl adenovirus 9 genome that is non-essential in vitro has consequences in vivo." J Gen Virol., 2010a, 91(1), 51-58.
Corredor, J. C. and Nagy, E. "The non-essential left end region of the fowl adenovirus 9 genome is suitable for foreign gene insertion/replacement." Virus Res, 2010b, 149, 167-174.
Guardado-Calvo, P., et al., "Structure of the C-terminal head domain of the fowl adenovirus type 1 long fiber." J Gen Virol., 2007, 88, 2407-2416.
El Bakkouri, M., et al., "Structure of the C-terminal head domain of the fowl adenovirus type 1 short fibre." Virology, 2008, 378, 169-176.
Romanov, et al. "Detection and quantitation of fowl adenovirus genome by a real-time PCR assay." Journal of Virological Methods, Jul. 2009, vol. 159, Issue 1, pp. 58-6.
Ojkic, D. and Nagy, E. "The long repeat region is dispensable for fowl adenovirus replication in vitro." Virology, 2001, 283, 197-206.
Idamakanti, N., et al. "Transcription mapping and characterization of 284R and 121R proteins produced from early region 3 of bovine adenovirus type 3." Virology, 1999, 256, 351-359.
Alexander, H., et al. "Growth characteristics of fowl adenovirus type 8 in a chicken hepatoma cell line." J Virol Methods, 1998, 74, 9-14.
Sira, S., et al. "Multiple reiteration of a 40-bp nucleotide-sequence in the inverted terminal repeat of the genome of a canine adenovirus." Virology, 1987, 159, 76-83.
Murphy, E. et al. "Reevaluation of human cytomegalovirus coding potential." Proc Nati Acad Sci USA, 2003, vol. 100, No. 23, 13585-13590.
Cao, J. X., et al. "Sequence and transcriptional analysis of terminal regions of the fowl adenovirus type 8 genome." J Gen Virol, 1998, 79 ( Pt 10), 2507-2516.
Ojkic, D. et al. "Unique features of fowl adenovirus 9 gene transcription." Virology, 2002, 302, 274-285.
Payet, V., et al. "Transcriptional organization of the avian adenovirus CELO." J Virol, 1998, vol. 72, No. 11, 9278-9285.
Francois, A., et al. "Construction of avian adenovirus CELO recombinants in cosmids." J Virol, 2001, vol. 75, No. 11, 5288-5301.
Lehrmann, H. and Cotten, M. "Characterization of CELO virus proteins that modulate the pRb/E2F pathway." J Virol, 1999, 73, 6517-6525.
Rigoutsos, I., et al. "In silico pattern-based analysis of the human cytomegalovirus genome." J Virol, 2003, vol. 77, No. 7, 4326-4344.
Berk, A. "Adenoviridae: the viruses and their replication." In Fields virology, 2007, 5th ed, pp. 2355-2394.
Davison, A. J., et al. "Genetic content and evolution of adenoviruses." J Gen Virol, 2003a, 84, 2895-2908.
Chiocca, S. "Viral control of the SUMO pathway: Gam1, a model system." Biochem Soc Trans, 2007, 35, 1419-1421.
Glotzer, J. B., et al. "Activation of heat-shock response by an adenovirus is essential for virus replication." Nature, 2000, 407, 207-211.
Weiss, R. S., et al. "Human adenovirus early region 4 open reading frame 1 genes encode growth-transforming proteins that may be distantly related to dUTP pyrophosphatase enzymes." J Virol, 1997, vol. 71, No. 3, 1857-1870.
Washietl, S. and Eisenhaber, F., "Reannotation of the CELO genome characterizes a set of previously unassigned open reading frames and points to novel modes of host interaction in avian adenoviruses." BMC Bioinformatics, 2003, 4, 55.
Tan, P. K., et al. "Defining CAR as a cellular receptor for the avian adenovirus CELO using a genetic analysis of the two viral fibre proteins." J Gen Virol, 2001, 82, 1465-1472.
Roelvink, P. W., et al. "The coxsackievirus-adenovirus receptor protein can function as a cellular attachment protein for adenovirus serotypes from subgroups A, C, D, E, and F." J Virol, 1998, vol. 72, No. 10, 7909-7915.
Favier, A. L., et al. "Structural studies of human enteric adenovirus type 41." Virology, 2002, 293, 75-85.
Clamp, M., et al. "Distinguishing protein-coding and noncoding genes in the human genome." Proc Natl Acad Sci USA, 2007, vol. 104, No. 49, 19428-19433.

* cited by examiner

List of primers for RT-PCR

| mRNA target | Primer name | Sequence (5'→3') | Position | Polarity | TM (°C) | SEQ ID NO: |
|---|---|---|---|---|---|---|
| fiber 1 | fiber 1 1st | TCGGAGCATGGTTGTTCC | 31708-31725 | antisense | 53 | 54 |
| | MLP leader 1 F | TCCTGATCGACTTCGGAGA | 9267-9285 | sense | 52 | 55 |
| | fiber 1 R | TAGGAAAAAGGGATAGGACCG | 31661-31681 | antisense | 54 | 56 |
| fiber 2 | fiber 2 1st | TAGAGCACGGGTCCCACAAT | 33094-33113 | antisense | 56 | 57 |
| | MLP leader 1 F | TCCTGATCGACTTCGGAGA | 9267-9285 | sense | 52 | 58 |
| | fiber 2 R | TTCCGCTGTTGGCTGGATT | 33070-33088 | antisense | 57 | 59 |
| GAM-1 | GAM-1 1st | AATATGGCATGAACCGTAGC | 40039-40058 | antisense | 51 | 60 |
| | TR-1 F | GGTGATTTTCTTCAATCAAAC | 39107-39127 | sense | 48 | 61 |
| | GAM-1 R | GATGGGTCTAGGAATATGCTT | 39827-39847 | antisense | 49 | 62 |
| ORF22 | ORF22 1st | TGATCGTCCATTTGTCCGAA | 39827-39847 | sense | 56 | 63 |
| | ORF22 F | CTCAATCGGTATGCACGAAA | 34480-34499 | antisense | 53 | 64 |
| | ORF22 R | TTTGTTCCCGCGTCCAAT | 33229-33246 | sense | 56 | 65 |

FIG. 8

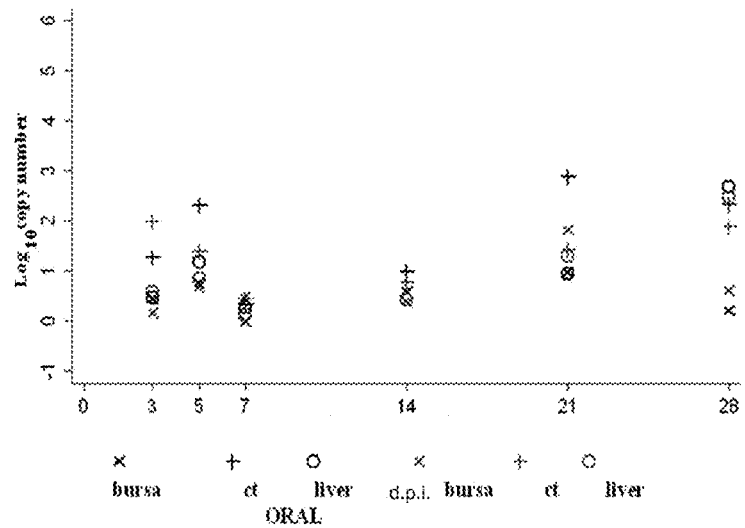

FIG. 9

SEQUENCE LISTING

<160> NUMBER OF SEQ ID NOS: 65

<210> SEQ ID NO 1
<211> LENGTH: 834
<212> TYPE: DNA
<213> ORGANISM: Fowl adenovirus serotype 4, strain FAdV-4 ON1

<400> SEQUENCE: 1

| | | | | | |
|---|---|---|---|---|---|
| acccgaaatg | tcacgacaga | aaaggctcaa | cggctgcaaa | tccgcttta | ccccatccaa | 60 |
| accgacgaca | cgtcgacggg | ctaccgcgtg | cggtacaaca | tcaatgtggg | cgacggttgg | 120 |
| gtcctggaca | tggggtcgac | ctatttcgac | atcaagggaa | tcctagaccg | agggccgtcc | 180 |
| ttcaagccct | actgcggcac | ggcttacaac | ccgctggctc | caaggagtc | catgtttaac | 240 |
| aactggtcgg | agacggcgcc | cgggcagaac | gtgtccgcct | ccggtcagct | gtccaatgtc | 300 |
| tataccaaca | cgagcaccac | caaagacacg | acggcggcgc | aggtgacgaa | gatttccggc | 360 |
| gtctttccca | ccccaacca | gggacccgga | ataaatcctc | tgcggcaggt | agaaaacgcc | 420 |
| aacaccggcg | tgctcggtcg | cttcgccaag | tctcagtaca | attacgctta | cggtgcctac | 480 |
| gtcaagcccg | tcgccgccga | cggttccag | tccctcacgc | agaccccta | ctggatcatg | 540 |
| aataacgcgg | gcaccgaata | cctgggggcg | gtagccgtcg | aggactacac | caacagcctc | 600 |
| tcgtacccag | ataccatgat | cgtgccgcct | cccgaggatt | acgacgatta | aacataggc | 660 |
| accacgcgtg | cgctcaggcc | caactacatc | gggttcaggg | ataacttcat | taacctgctg | 720 |
| tatcacgact | ccggcgtgtg | ctcgggcacc | ctcaactcgg | agcgttcggg | catgaacgtg | 780 |
| gtggtcgagc | tgcccgaccg | gaacaccgag | ctcagctacc | agtacatgct | ggcg | 834 |

<210> SEQ ID NO 2
<211> LENGTH: 45667
<212> TYPE: DNA
<213> ORGANISM: Fowl adenovirus serotype 4, strain FAdV-4 ON1

<400> SEQUENCE: 2

| | | | | | |
|---|---|---|---|---|---|
| catcatctta | tataaccgcg | tcttttgaca | cacttacaac | cgccgcgcgc | agcgcggctg | 60 |
| agtcattgca | tgaatttccg | ggtttgcgca | ctagggttct | gaactttgat | ctcatgacgc | 120 |
| cagtttcgct | ttcgcgtgta | gttcgaaact | ggcaacgcct | gggcaaagtc | ctaacgtgat | 180 |
| gtgtaattta | agtgtttttc | ccggtacatc | ccatatcctt | gaaatgttta | ccgttcgttg | 240 |
| caagtttgaa | ggtcatgttt | tattcgcttg | tttgtgttaa | atatttacgt | ttcagtgtac | 300 |
| ttcggtcagt | aattgtacta | attgcgggtc | aagtgacagc | cttaatagca | ccacgagttt | 360 |
| agatatcgat | cagataccat | tacccgttgt | cacgaaaggt | attttttccac | tccgtttaag | 420 |
| ggacggtcct | cacgatataa | gtactggcga | gtccgtcctt | tcgttacaga | tcttcctatg | 480 |
| agctatagga | gaactgttcc | tcttactcgc | tgtgcattgc | ttgacgctga | aaacgccgat | 540 |
| atcgcgatca | gcgagccttg | cctaaacttt | gaaattcaat | ttcaccctat | tacgcctcgg | 600 |
| cgtgtattcc | tccactgctt | cgaacccaac | cggttttgga | ccgaaatcct | ctggaacggc | 660 |
| accgtgaagc | agagtgaact | gaacgcggcg | ttggagaaga | tcgttgaact | gttataggtg | 720 |
| aggattgttt | tctgtacgtt | tttcgcggtg | gtgtcatccc | ttgacaattt | tctctcttt | 780 |
| tctacaagga | tggctgccgt | ttctgcgtct | ccgtctgtgc | ctaaacttct | ctataagaag | 840 |
| gttaaatcgg | atgctttcgc | tcctgtccgc | atgtcgccag | atgcagcggg | tttagatttg | 900 |
| cttagttgtg | aggacgtagt | ggtaccacct | cacgacaagg | cgctgatttc | tacggggtta | 960 |
| attttaatcc | tgcctcccgg | cacttatggg | agaatcgctc | ctcgctcggg | attggctgca | 1020 |

```
aagttcttta tagatgtggg ggcgggtgtg atagatgctg attatcgcgg tgaagtgaag    1080
gtgctcttgt tcaattttc gcaacatgcg ttcaacgttc ggaagggaga ccgtatcgct    1140
cagctcgttg ttgagcgaat ctttacaccg gagctcgagg aggtgtcctc cgttgatgac    1200
acgatccgag gagggaacgg attcgggtcg actggcactg gtagtgaagc gatgtcctct    1260
caaaggactc tacatttgtg gcttaaaccc aacggtactg gttcttcttc gtaggctgat    1320
tctgcgtgtc acgaacgcgc tttcgacgaa cccgactttg cggtgaagat ttccgcagaa    1380
gtggaggcag ataacgacgc ttacacgaat tgttttgcg aggggatac tggaagaaat    1440 tcttgctctc tctgtaattg ttctccgtgt gtaattcttt aggtatgttt cttaagattc    1500
tagttctctt ctgtttgatt gttgtagatt gttacatctt tcatactctc ggtgttcact    1560
ggcctaccgc gatgcttgtc ggtacttgga tgcttgttgc cgagctgctt aacgcctggg    1620
atgacttccg cggtcgaccc cgactgcgat ttatgtccat gcctgacttc gatgcccttt    1680
cacgcgccgc tgacgaactg gctgctatgc tagatgagaa ccgtaacgct gctccgattc    1740
agcgcggtga agaagaagtc tttgaagaca gcgaccgcga ccgcgattcg ggaaccgatt    1800
gtaactgatt gtaactgatt gaaatgtatt aaatgtgctc gcattacaga tggcttcgga    1860
ccgttactgg gatttagtga actcgctaat aaacaggggc atcgtgacga gagaacagtg    1920
gcaatctgcg gatttggctg aatatcgtcg gtactcgaag ggatacgtta gggggttcag    1980
cgtacgcaaa gttttgcgcg atgttattag acacatgtgc tggacaaaag tcctcggtga    2040
ctacttagta tgccctgtcg tgtgccaaga cgacattcat ctgaatccgt tttatgtaat    2100
tctgatgaaa aacggttaca accccgtgt tgtaggaaca attttgcata agtggtccat    2160
gcttacatca aataagaata ctgtgtgggt gtgggcggg gcagaaacgg gagggcccta    2220
tttggcagag gcaatagctt atacctctcc tgttgtcggg tgtgtggatt ggcggaatag    2280
ggccaatcct tttgcgcgca attataattg tttggtgtat tggttagatg gcgggctttt    2340
cccagagagc gcgatagggc tgtgtgaaca agtgttgaga ggggagggaa ctatggttga    2400
ggaggaggat acgtcgggag aacgtagatg gcgggaggtt aaccgtaccc ccgtactcat    2460
ttctacgagc cacgatgtaa cgttgaccta tgtgaaatat ggtcaaactt gtaaggatca    2520
cactaattcc ctgaggagcg ctatgtacgt gattcgcttg actgagcgca tggaacccgg    2580
ttttgttatt acttgtaatg acgcgcgtaa atttgtaacc tgggctagta ataatccaca    2640
cattaatgca gaagacatgt tgtaatttat tcaaatttgt caaatggaaa acattcaatc    2700
ttgatagtaa acttcaattg agacaaattt ctctgtattt gttcgcatgc ggctttact    2760 cgcgggctga agtatttggg gaggatcagg attctgtaac cggtcggggt taggccgatg    2820
cttaagtttt cgagaatgga tcttttgcag aagagcaatt gtaagcccca gagcgggttg    2880
cagtttctct cttttgcgcag actgcaacga cacatgatga tgtcttcgat ggggcagtga    2940
gggaagggat cgatgggac gtgttcttcg ataaattctt gaatggtttc gaaccagtag    3000
gtgaatacga gttggcctag gctctcgcag aatagggaat ggggcattct gcaggaacat    3060
tcggatcgga tggcgggagt accctcatcc gccgtgtagg gataaaagtt caggaggcgc    3120
agtctgactt tgaaaggggg catctcgagt ttgggaaaca gttcgtctgc actcacgtag    3180
tctcgacgac agaatgggaa catgcgttgt cccacgagga agtttaagaa atgcgagtcg    3240
aacgccagat gggtggggat tcgttcgaaa aggcgattaa gttggatagt cttggagtgg    3300
aaaacaattt tctgttaaaa gaaaatgagg gtataattaa taaagtagat ttccatggct    3360
```

```
cgtattaagc acctatatgg aaaagcgtcc ttcttgatcc tcgggatgca tatttgcacc   3420
cccctttggt gaaactcgga atgggttttg tgatatttcg gggtagggtt cattgttggg   3480
attaaccgca gtgatcaaga tgaatagaag tgtttcgtcc ttgcacgcat ggcagtgatc   3540
gaggtaggta tgggcgagaa tgcccagatg taccgggagt gggatttcgc gtgtagttgc   3600
tcttatttcg tcaacccaac gtatataggt tttcattcgg agggaatggc agaagagact   3660
atgaggtttg ggacaggtgc acctgtattt gagcaaccat ctggttgcac agttttggt    3720
ttcgtcggct ttgatatcgc gtagacgtat ttccactcgg aatgatttga atcgaggata   3780
gaaaacgaat tcctgaaagg aatgggtgt tccgggagtg aaaaactgag actttcccac    3840
aaagaaggcg aaaaattctt tactcgtgag gacttggaat gacacagagt gaataggagg   3900
catggaaatg atatgggaga cgtgcccgtt gcggtcagat cgtttgtgaa tgaatacagg   3960
gtgtagttct tcggagggta tctgcaacga gaaggattac ctagtgtgta tgcgcgttgg   4020
gtaggggaaa gaattgtgca tgtagtgcat gaagcatgga aggctaatgg cttggctggc   4080
ggattctgaa agcctgagga tgatttcacc gttttcgatg gagagtggtg ctacaccatc   4140
gttatgacaa tgctgtacta tttctgagat tagttcgaga ggcgtagctc ccgtgcaaaa   4200
cgcgcagtgg catagttcat ccgaggtaag gggacctaga tctacgggga agggttctgc   4260
tctgactccg ttttgtatag cttctttcca agagtggaaa aggagctctc tgagagactg   4320
gcaaaatagg gaattgccgt ctccgcaatt gcaacgcagc tttactatcc atccgagttc   4380
ggtatcctcg gacggtctga gaatacagta aacagagatg tctgctctga acggtctaac   4440
tctagggtaa aggctcgttt gtgaatactc gtggggaccc gggaagggga attgaatgtc   4500
accgttcatg aactctacga atcggtggtc gaatagcatt tgtatgttta tgacatcgaa   4560
gaggtcgtag gttctgatgg tgaaactgtg ttcagagtgt cgtacttgat cgtcttcggg   4620
tgtccagcga aagatggaag tgggtcgtcg tgtggtctgc aagagattag taataataga   4680
catgaatgct gtgtggcaga atttcgaggg ttttaaggaa gcaggacagg tggacgtagt   4740
cgcgaaaaaa tttgggatg cctaatctaa ttcgaccctc ttgtctccta aagatgacga    4800
tacttcgccc ttggaaggtt tgtttgacga tctcggtgag aatttcgtag atcgtgtgga   4860
aagtgcagtg gctgcagtgc cctgtgcgcc ttttagcata agcgcgaatg gagatgggat   4920
ggcgtatggg tacggaggcg aggtgctccc gtacatctaa tcgccattgc tgggccacgt   4980
attgattaag cgctcgacaa acaacgagt atgggtcttt gcaacggcag tggctgtaga    5040
gaatccagta ggtggatgat cttttttaggt ccagtttgat ggtgatttgg aaggcaggga  5100
ggcataggtt gagctctcga tgtgagtaat gttctgctga ggggaagggc agtagggctc   5160
gcccgttgat gaattcgagg aaccgtaggt cgaaaaagtg aatggcgtcg catatgtcta   5220
gggcgggtcg acagaggatg gtgtagtcgt ggcggtggtg aggaggggaa gccctcgaac   5280
cggtcaaaag caccatatcg gacacggggt tgatctgaaa caagatttat tagagtgcat   5340
cagagggcga agcccgtata caattatcac aaatctcatg gtctttctta caatggatac   5400
tgagtaagca tggtaacccg gtcgcgttca aaaccaagtc ccttagttct tttcgtggag   5460
agtgacaggc gggcaccgat ctgttttcct gtacagaata gaggatgcg gtgtttcgac    5520
tggagaagct gtccgcgata ctgagatccg agcagtgtat cagaacagag gtgtgaggga   5580
tatgcctcat ttttccttg atgacggtgt tcagaaagtt ccttccata aagtgtagca     5640
ttatggcgtt gggtctctct tgcacgaagg gcaggcagta gagcggcgtg atgggggaga   5700
tttctgcgag tgtgtcgagc gagttgatcg cactgtcggt gatagccatg gggaagcagc   5760
```

```
tcgaaatgac gttgaagagc attttggcgt tggagtgtcg gtcaccgcac aggacaagcg    5820
tgttgagctc acccttgagc catgcaccga tggtcgcgga tgctactctg gcgttgtagc    5880
cttcttttc gaggagttgg tagaaccagt tttccctggg gttgtagaag gcgctggaaa    5940
tagggtcgga cgcttcggga ggcagttgga ggaacaggct ctgtgacggt ccgaagcgct    6000
ccctgaggac cgacaggacg tattctcgct cgtgggcagg cagcagatgc ttggtgggga    6060
aggtccattg gagatcgtgc gcgatgccct cttcgaagag ctgttcgatg agaacggtga    6120
ggggatgcat gggaggggct tcttgcgaag agtcttcgaa taggaagaat tgatcttcgt    6180
gcgaatcctc ttctcgtttc gcacgcttag tagtcgtctg aaaggagag aaaatcagcg    6240
tgatattcgg aacatgtaga gcacatatca ccagcggatg acttggaaca taggtatccg    6300
tacgggttgc agcattcgag gacgtcgttg gaggtcgcgg cgtgagtttt gagtctccgt    6360
atgtacccga cgagttcagc agcctcgaat gcgagaccta cggtgggcgc ttcgaagttg    6420
atgatgacgt gctggttttt attggtgggc agtcgatcgg ggtgtgggag ggatctgagt    6480
ctaactaagc atttggtcgg cttgatggtg actaattcac cgtcgctcgc gatggtcgtc    6540
tctcgtccct ggagcatgtt gttgacggtc gggcttgga aaggaaggga gtggaaagct    6600
agaggaaagt agaggaactt ggtttcgcgc tgcaccctgg cgtattcttt catgtcaaat    6660
tgattaatgt cgcccatgag cacacactcg aaagctcgta cgaggagaa ggcgaatgga    6720
tcagcgcaac tggacgcgtc cccgactacg tacatagtgt taacgtagtc tttcctgggg    6780
ttgtagggga atgcgtctag ccaggaggtg atggcgttga ccagagaggt gagatgcatt    6840
ccttctttgg cagcgatgga cgccagctgc ctcgagttgg aaagcggcga gcgaccatgt    6900
ttcgagcgca actctagggt ttgataaaga ccgtaattgc aatagatgcg cttggcttcg    6960
aggagcagtt cggcggcgtt gttggcatgc cttttatact gctcggcgtc gatttcttcc    7020
cactgtgagg gagtgaaaat ggacctgagc tgcagatgga aggcgagctc tgacatctgt    7080
tcgtgattgc taggccttt ttgtctcgtc tggcgagtct gagggagaaa tggtttcgag    7140
aaccgttagt ttacgacgct ttcccaatg gggtttgtga ttatctgtaa atcgcatgat    7200
tagtttagcg gctttaagga aattttcctg aatgtttata ttcaggggta tgatatcata    7260
gtttctgtct agagtgcacc agcgaaagga gtcggagacc gggtctgggg tgtatacgat    7320
ccagctgaac ttttggttct gctggagata ggcaaagtac gctttgagga ggaccatgat    7380
gtccttcgaa atgttgtgcg cgaacgaata gaggaagcgc gagaactgaa attggggat    7440
gtgacaggac atgatatgaa ttttggcatt gactttgaga gtggggacgt taccgatggc    7500
cgttctggga gccatgttgt ggagaacaac aaagatgtag aaagcggagc aagcagcaga    7560
gcgagcgaaa gcttggagg ggagcgcgtg aaagagcacc gagacgctag aacccgaaca    7620
cagtttgtcc atgcattcgt ccatcacgat agctagaggg cccttcttcg aagccgtcac    7680
atagatattg ttggggttct cgatattgag gttctccggt gtagtagctt cttcgtaggt    7740
catctcgata aaatccggtc tgaacgtgca agtcctgggg gcgaatgtcc cgtcgtccct    7800
gcagtcgtag ttggattcca ggagctgtag gttccaagca gtttgctcga taggggggat    7860
catattcttc tccggcgtga taagataac cgtttccggg ataggttgca gcatgttgca    7920
cgagatgagt gcgcgcagca gatgactttt tccggatccc gttggaccgt agatgacgcc    7980
gatgacgggt tgtcgtccca tgttgagcga ctgtagttga ccgttctga gatactgcct    8040
gtcgtggtgt tcttgttgtt cgacgttttg ctgtagttcg tggaacttgg cgtctgttcc    8100
```

```
gccgagactg tagaactcgt cgaacgggag aaaccggtgc tccttgaaga gctggggcgc    8160
cagatcggtg gctcctgcgt accatcccgt gactcggttg tagaactgtt cgccggagag    8220
gtagtcttct tctcgatact gccaggcttt tcttttctta gggatcgcgc tcatccgttt    8280
ctccgaggag ctcgagtatt tcgtcacact cttctgccgt taggaaggca taggggtcta    8340
ttcgcagcgg cgcaagcggt tcctcgtcgc ccggtacgga cacgtggcgt acttcctcaa    8400
ccgtgcgcgg gttggggtgt tcggtgtcgt aggggtagag ggcgttaccg tactgatatt    8460
gcgtggggtc cttccagggc ctcaggatcc gcgttagctg ctcgttgtgg atcgtgaatg    8520
gctcgtagcg gctgaccttg ttaagcagcg tggtcttgaa gatggttcgc ctggtgtgta    8580
gttcgggaat gcggctgtct gctccgaaca gttggtcttc atagcgcatc cagcaacgta    8640
ggagggtatc gtaaataagc tccgcctgtt tgtggccctt ggatcgaatt ttcccggtgc    8700
ccacatagcc gcattgaggg ttcgtgcaca ccgcgtcttt gagaccgtag agttttgggg    8760
cgaggaaaat cgcttcggaa ctgtaggtgt cgctaccaca ctgtttgcac ttgatgtcac    8820
aatcacatgc ccagtatagg tctggttttct cggggtcaaa cgtgaggcgt gtgctcttag    8880
acttgatgcg gtgagctcct cgcgtcttca tgcgttcgta acccgtctcg ctgaggaata    8940
agctatcggt atccccatag agcgtttgca gctctcggtg tagaatgtgt gtgccctgt     9000 ccggtccgtg taaaatttca caccattcgc taaaaaatgc tcgtgaccaa cccaaaacaa    9060
agcatgctat ttgggtggca taacgtttgt tttcgacttg tttgtccagg cttttctaggt    9120 ggagtacggt gagcgcctcc ggtggcgcgt cgaggaatcg aacgggcttg aatgcggtct    9180
cgttggctcg cgagtgggcg gggtttgttt ctgccggcgg tcgcccgtca tctatataaa    9240
ggccgcaggt gagcgcttct tccagctcct gatcgacttc ggagaggtct gcctcctcct    9300
cggcggtaag tacgacgttt tcgtccttac tggtactctc gcagtgttcg gagtcctcct    9360
cctcctcgtc atcgctctct tccgggggtt taaaatgtgc taataaggat ggcgcagaga    9420
agggatctcc cgtctcgtaa agagttttgc ccgaaaacga cctgtcgttg agaagcgtga    9480
catgtttgac tacctgggtg ccctcgtaga tctccttttt gtccttgtcc gtgaggtctt    9540
gctcgaacac gatacgcgtg gtatccatgt tggtcgcgaa ggccccgtag agggcgttgc    9600
tgagcatttt cgagatggat ctcatgacct cattttctc ttgatcggct ttttccttgg     9660
ccgcgatgtt cttgctgacg taatccgcac aaatggtctt ccactcgggg aagacaatgt    9720
tcatgtcgtc atgcagggcg gtgactttcc acccgcggtt gtgaagcgtg atgatgtcta    9780
ggacggtgac gacctcgtcg tagagcacct cgttggccca tacgaggcga ccgcctctgc    9840
ggttgcacag cggagggagg gtatcgagct gttcggggg cggcgggtag gcttctattt      9900
tgaggatgga aggtttgatg cgtgcgtcga agtagctgat gggtgccggc tggagcaata    9960
tggcgttcag ctcgtccacg tgcgccgctg tgaacttggg atcgagaggc ataccgtggg    10020
gcatggggtg ggtgagggcg gaggcgtaca taccgcagat gtcgaacacg tatacgggtt    10080
gcgtgaacgg ccctagcacg ctgggatagc atcggccccc gcgcagcgcc tggcgaatgt    10140
acttaaacat gggtcgatgg ggagcgtaaa cctcggccac gtaatcggtg ggtatggatt    10200
tgttggtttt gttgccttttt ttgtttcgtt tcgcgggttt ggattgtctt ttgtcgagct    10260
gttcctgaac gtactgcgag aaggtaagtt gcttccagaa ggcatgtgta ttgctgggga    10320
tggtgggcct gacgaagatg ttgtaattgc cgtgcatgcc cagctcttgc ttaaagtatc    10380
ggtcgtagct ttcaaagagc gtgtgcgcca gcttttgggt gacgcgcacg tcctgcatgc    10440
agtactcgag acaggctcgt acgaggtcgt acggctgtcc ggggtgattt tggttccaca    10500
```

```
gctgttttttg ttcatcgagg acagaggcgt cctcccagta acgagcgacg gggaagccgt   10560
cggcgtcccg atcgtagtgt ccgcgcgaca cgtgttcgtt gatggcttcg tacgacagt    10620 gtcctttgga cagttctaag gcgtaagcgc tcgccgcttt ggcgagtttg gctccgctgg   10680
taagctggag tgtatcgcgc accatgaatc gcacaaagac ggaccgcatg tcgcgttcgt   10740
ctacgacgcc tttcacccac cggtgtaacc gggtggggtc cttttttgctg aagttggggt  10800 tgggcatgtg gaataggatg tcgttgaaca atagtctgcc gacgcgaggc atgaaggatc   10860
gatcgcagcg gcaggcgtcg gggaagaggt ctcgtcgctc gaccagttcg gtggcgagga   10920
gcagttcgtc gaacttggtg atgttgtgac ccaacacgat gacgtctacg gagtagaaat   10980
cggacggtaa ggtgagaggc ttgctgggct gtaggaatttt ttcgtacggg atgtgataga  11040
tggatgtgta gttccgtcg ctcatgagtt ctccgcagaa ctctcgattg gctcgacagt   11100
agcggcgcac gaggtgttcg gcgaagtgct gctggagtcg tgtgcggtaa gtccggaatc   11160
gtcgcgcgac ctcgcccggc ttcgggtcga tccagtagaa gccttcgtcg agctgtcgga   11220
cgtcggtgtc ttcgagcgct attttttcgcg cgacctcgac gagcgcgggg tctccgctga  11280
gcatgaaaca gagcatgaac ggttgcatgc gcttcccctt ttgttcgaag acggtgtacg   11340
tttcgatgtc gtaagtgaga aagagctgtt tgcagtgggg gctttgcgcc gggcacgaga   11400 aatgacgtgtt ttgccacatt tcgctacctg ttttctgtac ggcgtggtag tagaaggcgg  11460
atcgcctttc gttgcacgcg tggtttcgca cccagtgtcg cccgcaggtg ggacagtgtt   11520
ggacggcggt tcgcgagagg acccagagcc agcgttcggg ctctcgacgg gcgtcccgag   11580
ctagcaggat gggaggtagg agcggtgctt cgtcctcgaa gaggcgttcg atgtcggcgt   11640
ttcttccgag gaacttgagg acgccgatgt atttcggtcg gaagacgcgc agggagttcg   11700
tcgggtcacg ctcgtagaag ccgtagtcga taatgtcgta ctggcgactg cgttcggtaa   11760
ggaggaactt gtgcagtttg aggaattttt tcatgccccg cgcgaagggc acgcattgta   11820
atttgaacgg ctctccttcg atgtagaaaa tgccattttt taacacgtct ccgggtacgg   11880
ttttgaacag ggtcgatggg gggcgcccgg gtgcgctgtc gggatcgttc cgctgacgcc   11940
tgggtaccgt tcgcacgagg tgagagtgct cgcccaggat ggagcgtcgc agacgtcccg   12000
ctgcgacgtg ttccatgacg ctagcggcgc tgttggggat ggtatcgctg ttggaagtcg   12060
cgctcttccc tcctgttttg taggacttgg cgtaagttgt cggtaatgcg ctgattggtg   12120
gagatggcta cgatgccccg gtacttgagt cggaagctga tgtcgatgct ctcgatgagc   12180
tcctcgctaa ggttgagttg cttgaggacc tcgtcgatgt ctcccgactt gtctctgtat   12240
tggatatcgg agagaaagag ttgttgatca gtttcgtcca tgccctcgaa ttgtcccgtg   12300
cgctcgacca ttagcaggaa gtcgcggaga atgcggttcc atagggtttc gaaaatgcgc   12360
gacgagttgg actgctcgct ccaaattcgt ttaaaaacct gctgcgcgtt gacatcccaa   12420
cccacgatga gcacttgcag cgtgtcgatt tccacgtagc gtctgaactc gcggtagttg   12480
ataaagtgac tgtacaggta gtatagcgtg gaggcgatgt gctccgcgag gaagaagtag   12540
aggacccact tcctgaggaa ggagtcggtg acgagagcca cgtcggattg ctgtgtctgc   12600
aggagcagac ggtagaaggc ggtggcgaac tggaacaggt cgtgcctctg cgcggtgcga   12660
ctgagctctt gctgtaaggc gtcgatggcc tcgagcgcgg tccggacgac ctcgtcgagg   12720
agctgttctt cctcttcctc ttcttcgggc gggaagggct ccagttccgg gaggtattcc   12780 tcgggggggtt ggggggaggg gggtctgggg cgccgtcggc gacgcgtgag cctcggcaac   12840
```

```
ctgtcgacga agcgctctac cgccctccgt cggatctggc ggatctggga cgcggtgatg    12900
gcgcgtccgt gacggtcgcg aggccgtaat ccggatctgt cggtgactct gcggtttcgc    12960
aaggtaatgg cgcctcccga gagcgaggtg tcgctagcca gagtactaac gagacatctc    13020
gccattatgg acgcaggatc ctgtccgagc catcccgctt gaggatcgtt ttcgaccgcg    13080
cggacgaggc gctgagtgtc tagctcgcta aaggcttcga cgaagaggtt gagccaatcg    13140
tcttcagcga acacttccga tccaggtaag aatctgtacg tgctttcggt ggtaaagagg    13200
tcgtaggcgt tgcaaaatag gtagtgacac agcgcaacgc ggaggtaacg gatggccgcg    13260
aggatcgcgg cgtcgcgatg cgaagccgtg cgaaggacga cgtcgtccct gagcccgctc    13320
gcgccgctac ccgtcagata gctgtgatcg tcggcgttga aaggttgcgg aatgacccgt    13380
ccgtctcgac ccacgacgac tcctctgcct cggagatacg ctccctgcat gtcggccgcg    13440
atgcgatcca tgagcaccgc gttgtgcatc tgggtgaagg tgccgtgaaa gttgtctagg    13500
tcgaggaagc gcatgtactg tccgacgctg accgagtacg agcagtcggt gaggcaggtc    13560
cagaagagcc tgcgcggtcg ttgtgtcgga gggctctcga atccgagctg catgaagacg    13620
cggttgtcaa agaagtagtt gttgagcgtc ctgtgcatgt actggtagcc gagcaacaga    13680
tgcggggcg gcagtccgtt gtaggggttc tgcgcgacgt tggctccccc cggcgttagg    13740
tcgcgcagct gcatgagtct gtagtcgtag attcggctga cgagaaagac gctacgggga    13800
tgcacgaggg ctggttgcgt gcgcaccatc gggaaatcgg cggcgatgac gggttcgcag    13860
aagcgtacgg tgtttaggct ttggccggtg agctccgcga agatcctgta agcctgaaat    13920
cgaccctga cgtttttaga cacgcgcgtg gctgcataat gcacccggtt cttcaaaacg    13980
tgcgaaacgc gagtttgggt tccggcggaa gatcgagtca gtcgcagcag caccagcagc    14040
aggagttgcc gcccgtctac gatcagcagc gtcaagccta ccagcaccag cagccgtacc    14100
aggaccgcag cgcgggcggg ggtggcggcg cgcgagctcc ccccgaccct ccccgatacc    14160
cagcacagca cgcgcttccg gtggcgacgg ggcctccgga gatggcggcg gggggcgtgc    14220
cagaggagcc tccgtcgtgt gggatggcgg tgggagccac gctagacccg acccgcatgt    14280
acgaacgtga cgcggctaga aaggggggcca ttcccgaggt gaacctgttt aaggcgaagc    14340
cggacacggt tcctcaaggc gattacgatc gagacatgat gtatcgctcg ggacaggtag    14400
tgcagttgga caggaaccgg gtgctgcgcc ccgaagactt cgcggcggac gcgggtgacc    14460
cgacgttctc gcccgcggtc aatcacatga aggccgccga gttgaagcgc gcctcggagc    14520
aaacggcttt cggggaggag atgcgcaacg tgtgtcacca gacgcgtatc cgcacggcgc    14580
tctcccgacc ggaggtcggc gcgggcatct actacctgta cgatttcgtg cagacgtaca    14640
tggagcaccc ggacgggcgc gtcaaactga acccgcagct ggtgctggtg gcgcagcacg    14700
cgggaaatac gtcgctcgcg caacgcctat gggcgatcgc ggaagagaaa aacgcgtggc    14760
tgagagacct gatagagatg gcgtacatga tcgtgaccga cccgtacttg agcatagagc    14820
agcaggtatc ggcggtgtgc acgacggtgg tcgagctgag catgaagtac gccaagctgg    14880
ccgcgaagaa cggctacccg tccatggctc agatggccaa ggcccaggaa tttttctacc    14940
gggtgatgca ggcggtgctg gacttggggg tgcagttagg cgtgtacaac aacaggccgg    15000
taaccttccg tcagaagcgg atgagcgaga ttccgcagat gactgacgcc gagtacatgt    15060
tcggtttgac ccaggcgctc gagaaccgac ctccccaagg ggagtttccg gccgacggag    15120
agttttccga cagcggagag gaggatgagt tcgactgaag tcttcggcgc gctggcgccg    15180
gtggggcgta ctgaggtggc cgacgcgctg agctcccacg ccaacagcaa ggatgcccgc    15240
```

```
agtctccgtt acgaaccgta cgctaaccgc ctgatcaaat tgcaaacggc gatggtgccc   15300
cctaaagtgg acgggacttc ggaacgggta gcggaggtgg tcaagggctt ggcagagcag   15360
ggcgccatct accccgatca gatgggagcg atccattcgg acttgctgaa ccgcgtgtac   15420
acgtggaact ctatgggcgt tcaggagagc attcaagctc tggtgaacga cgtcatccac   15480
ggtcaaaata aagtgttgca ggacgaactg gcccgcacgc gcgagatcgc gaacgcttcc   15540
atgttgactc gtttcttcga cagtctgtat aagacggtcg accgggggca acgcaacttt   15600
gagggcttta agaagttgct ccgcttgttc gtgaataacg ttccgaacgc ggaagtgtac   15660
agctcgggcg gctccttcag cttgcagatt aacatggggg gtcagagtca gaacatcaat   15720
ctgacgaacg ccttcgacaa cctgaaggac atctgggggg cgcggtggga tgccgtaaac   15780
aatccgcgca taggggcgtt gctgacgcct aacacgcgcg ccctgctctt cttcgtgagc   15840
accttctacg actacggctc gatggagccg ggtagctacc tcgataacct gatgcgtctg   15900
tacaaggagg ccattagggc cgacacggac gcggagggcg acgccatcat ggaactcggc   15960
gacgcgggcg ccaacctgaa tctcaagttt aaccagtaca aggacacgct caactatctg   16020
ctgcagaata agccgtccgt cccgcagacg gggccgctag agatgagccc cgagcaggag   16080
agtcttttta agtatttgat gcgtcagctg agacgggcgt tgaaagacgg cgtcaactcg   16140
gacatagcca tcagcacgat ggcgcagtac gtggatccgc gattgtatac gagcaataag   16200
gtcttcatcg acaagctcca gaactacttg ctgatggcga gcgcgcgcaa tccctactat   16260
tacaagacga tcgtgctgga tcctcactgg gtgccgccgg cgggcctttta tacggacaac   16320 tttgtgatcc cggaaatgat gcccaatttt agtgactttg cgagcgagct cgagtacggc   16380
ggtccctcgc gggacgagta ctttgacgac agtccgttcc gtccgccgcc ccagaaaaag   16440
tttacggaga aagagcaggc cgactacgat tcgctgatca acttttttcga ctcgactttg   16500 ggcgtgcagt cggaggccgg ttggattgca gatcaccgcc tcccgcaggc cttcgacggc   16560
gcgctgaacg tgtccgagcg cactccctac aacacccccc tgcccgacga cgcaccgatg   16620
cgcagtcgca acgcctcggt gagctcggcc acggacgcct tagggcagct gaagctgagc   16680
ggcaccgggg gcgccggctt cttcgacagc ctgaagccga gcgtgggcac acgccgttcg   16740
acaggtctgg ccaagggact tgcgggcacg ggacaaccgc cttgcccatg gccggcgagc   16800
gtcggctacg cgtccgcggg atacgggccc gctcgcggaa tcagagggtc gggactggct   16860
agacgagcgt tagcagcgag gggtctccgt caaggcaagc gcctacgctt ttactaacga   16920
gagctagata ccattattaa gggacactta ccgccatttc gacaggatct ccgacaagga   16980
gtggtgcaat gtgggggttg cagccgccga cgtcgattcc gccgcctcct ccgccgaccg   17040
agttaacgcc ctcgacctat ccggcgatgg tgaacggcta tccgcctccg gccgcgtccg   17100
cgcagagctg ttcctctagc ggcggtcaga gcgagctgta tatgcccctt cagcgggtga   17160
tggcccctac gggggacgg aacagcatta agtatcgcga ttacgcccg tgtcgtaaca   17220 ccaccaagct gttttacgta gacaacaagg ctagcgatat cgatacgtat aataaagacg   17280
ccaaccatag caatttccgc accacggtga tccataacca ggatctggac gcggacacgg   17340
ccgccaccga gtccatccag ttggacaacc gctcctgctg gggcggtgac ctaaagacag   17400
ccgtgcgtac caactgcccg aacgtgagca gtttttttcca gagtaacagc gtgcgcgtgc   17460
gcatgatgtg gaagcgcgac ccgccgacta gcacggctcc tccagagcgcg gtaggcagcg   17520 gctattcggt gcccggcgcg cagtacaagt ggtacgacct gacggtcccc gagggtaact   17580
```

```
acgcgctgtg cgaactgata gacctgctca acgagggcat cgtgcagctc tacctgagcg    17640
agggtcgcca gaacaacgtg caaaaatcgg acatcggggt caagttcgac acacgcaact    17700
tcggcttgct ccgcgacccc gtgacgggac tggtaactcc gggcacgtac gtgtacaagg    17760
gttaccaccc cgacatcgtg ctgctgcccg gatgcgcgat cgactttacg tacagccgcc    17820
tgagcctgct cctgggcata gggaagcgcg agccctactc gaagggggttc gttattacct    17880 acgaggatct gcagggaggg gatatcccgg ctctgctgga cctcgactcc gtcgacgtga    17940
acgacgctga cggtgaagtg atcgagctcg acaacgctgc tccccttttta catgacagcg    18000 cgggcgtgtc gtataacgtc atttacgacc aggtgacggg aaaacccgtg acagcgtatc    18060
gctcgtggat gttggcttac aacgtgccta actcgcaggc caatcagacg accttgctga    18120
cggtgcccga tatggcgggc gggatcgggg cgatgtacac gtccctgccc gatacctta    18180 tcgcgcctac cgggttcaag gaagataaca cgaccaacct ttgcccggtc gtcggcatga    18240
acctgttccc cacctacaat aaaatttatt accaggcggc gtccacgtac gtgcaacgcc    18300
tggaaaattc ctgccagtcg gccacagccg ccttcaaccg ctttcccgaa aacgagattc    18360
tgaagcaagc gccccccatg aatgtttcgt ccgtgtgcga taaccaaccc gccgtcgttc    18420
agcagggtgt gttgcctgtg aagagctcgc tccccggact gcagcgcgtg ctgatcacag    18480
acgaccagcg tcgtccgata ccctacgtgt ataagtctat cgcgacggtt cagccgaccg    18540
ttctgagttc cgcgaccttg cagtaggact gaacatgtcc attctgatat ccccgaataa    18600
caacacaggt tggggtatgc gtcgccgctc tagatcatca tccatgcgcg gggtggggat    18660
gcgtcgcagg gctcgccctc tgacgctgcg ctcgctcctg ggtctgggca cccggaggag    18720
acgcggctcc cgccgctccc ggccgaggac caccagccgg ctggtcgtcg tgcgcacccg    18780
caccagcagc atgcgaagac gtcgttgatc gtcgcagcgc ggactacgtc gcctaccgtc    18840
gcctccatct accgattcta gttcgaacga cttgttatag ccttcgtgac tttggtaacg    18900
actttgtacc gtccctgtac agacaggacg gaccagcgcc gccttcgtcg ttccccgacg    18960
cgtcgctaat tcttcgacca tgcccgccgt gcttttgacc ggggggtcgca ccgcctccaa    19020 gcgtaaattc agcaccaagc agcgtcgcaa gaaagcggtg tccgtgccca agatccgctc    19080
gcgcagcggc aagcgcagcg gcgttcggaa gcgttcgtcc atttcggtgc ccgtgagcgg    19140
cacggccagc gcctcggaga gagctgcctt gcaaaatctg gcgcaacgcc ttcagagggg    19200
caactacacg gcctggcgct cggcggaccc ctcggtcgcc gcgagcgaag ctgccaaggc    19260
ggccgccgcc agcggcgccg cagcctacgt gcgagacctg actacgggca ccgcggccga    19320
ggcggttccg ctcaccggca ccgggaggcg gcgccgcacc gggacaaggc ggtcgatgcg    19380
gggtggcttt ttcccggctc tgattcctct gatcgccgcc gccatcggcg ccatccccgg    19440
catcgccggc accgccgtgg gcatcgcgag ccttaaggaa cagcagagac aattcaataa    19500
gttgtatggc aacaagtgag agagagaacc gaagtgctga ctgtgtgact gtcgtctaag    19560
acgtttccaa taaaaatttt gtagacgatc gatcactcgc cgccgtcgtt atggactacg    19620
ccgccttgtc gcctcacgtc gggtcctggg ccctgagaga acatcacctg gaacctcca    19680 ccctgcgcgg gggtgccata aactggtcca acgtgggctc gcggctctcg agcgcgctga    19740
gctccaccgg acgatggctg tacaacaccg gcaaccgctt cgtccactcc aatgcttta    19800 accagataaa gcagggcctt aaggatagcg gcatagtgcg caacgtggcg tcgctggccg    19860
gtgagacgct cggcgccctg acggacatcg ggcgcctgaa gctgcagcaa gatctagaga    19920
agcttcgccg taaggctctc ggggaggaag gtcccgccac gcaagcggag ctccaaagcc    19980
```

```
tgatccaggc tctacaggcc caactcgccg ccggagccga ggtctcgccg cagggttctg    20040
cgcacgtccc gcagacggta ccggcgccgc ccgtgccgac cacacgcccg attcccgaga    20100
tggtgacgga ggtgaaccct cccatcacgt cctccgctcc cgccgtgccc gtggtggacg    20160
tcccgactac cctagagatg ccgccgcccg cgaagcgaag gcgaaagcga gccagagcgg    20220
gctcctggag agcgaggctc aacaccttgt caggcaccgg agtgaatgtc agcagtaggc    20280
gattgtgtta ctaaacgggt tgtgtatgta tgtcgcgttt cgtctaggtt cgcaccgtca    20340
tggcggccct cacgcccgac ctgactaccg cgactccgcg gctccagtat tttcacatcg    20400
cgggccccgg gacgcgcgaa tacctctctg aggacctcca acagttcatt ccgccaccg    20460 gaagctactt tgacttgaaa acaagttca gacagacggt cgtggcgccc acccgaaatg    20520
tcacgacaga aaaggctcaa cggctgcaaa tccgctttta ccccatccaa accgacgaca    20580
cgtcgacggg ctaccgcgtg cggtacaaca tcaatgtggg cgacggttgg gtcctggaca    20640
tggggtcgac ctatttcgac atcaagggaa tcctagaccg agggccgtcc ttcaagccct    20700
actgcggcac ggcttacaac ccgctggctc ccaaggagtc catgtttaac aactggtcgg    20760
agacggcgcc cgggcagaac gtgtccgcct ccggtcagct gtccaatgtc tataccaaca    20820
cgagcaccac caaagacacg acggcggcgc aggtgacgaa gatttccggc gtcttcccca    20880
accccaacca gggacccgga ataaatcctc tgcggcaggt agaaaacgcc aacaccggcg    20940
tgctcggtcg cttcgccaag tctcagtaca attacgctta cggtgcctac gtcaagcccg    21000
tcgccgccga cggttcccag tccctcacgc agaccccta ctggatcatg aataacgcgg    21060
gcaccgaata cctgggggcg gtagccgtcg aggactacac caacagcctc tcgtacccag    21120
ataccatgat cgtgccgcct cccgaggatt acgacgatta aacataggc accacgcgtg    21180 cgctcaggcc caactacatc gggttcaggg ataacttcat taacctgctg tatcacgact    21240
ccggcgtgtg ctcgggcacc ctcaactcgg agcgttcggg catgaacgtg gtggtcgagc    21300
tgcccgaccg gaacaccgag ctcagctacc agtacatgct ggccgacatg atgtcccgcc    21360
atcactattt cgccctgtgg aaccaggcgg ttgaccagta cgaccccgag gtgcgagtct    21420
tctccaatga cggttacgag gaaggcgcgc ccagctacgc cttaaccccc gaagcggtag    21480
gcgcgggaga aggctacggc cccgatctca gtcaaattaa actctacacc aacaacaccg    21540
ccgcgaacga caaaaacacc gccgtgacca acgccactac caacttctac ttcggcacgg    21600
taccctccta cgaaatcgat atcagcgcta cccgaggcg caactttatc atggccaaca    21660
tcgccgagta tctgcccgac cgttacaagt ttagcatctc cggcttcgac gccaccagcg    21720
tcgcgcctac cacctacgag tacatgaaca gcgcgtccc cctcaccaac gtcgtcgaca    21780
tgttcacgaa cgtgggtgcg cgttggtcca tcgaccagat ggacaacgtc aacccttca    21840 accaccacag aaactggggg ctgaaatacc gctcccagct gctgggaaac agccgctacg    21900
tcaacttcca catccaagtg ccccaaaaat tcttcgccat caaaaacctg ctgctgctct    21960
ccggctcgta cacctacgag tgggtgctgc gcaaagaccc caacatgatc ctacaatcca    22020
gtctgggcaa cgacctgcgc gccgacggcg ccagcatcgt ctacaacgag gtgaacctca    22080
tggccaactt catgccatg gatcacaaca ccagtaacca gctcgagctg atgctgagaa    22140
acgccaccaa cgatcagacc tttgtggact acctgggagc caaaaacgct ctctactcgg    22200
tgcccgcggg ctccaccgcc ctcaccatca acattcccgc tcgcacctgg gaggggatgc    22260
gcgggtggtc cttcactcgc atcaaggcgg ccgagacgcc tcagctgggc gcccagtacg    22320
```

```
acgtcaactt caagtactcg ggcagcatcg cctactcaga cggaggcttc tacctctcgc    22380
acaccttccg taacatgagc atcctcttcg acacgtccat caactggccg ggcaacgacc    22440
ggttgctcac gcctaacatg ttcgagatca agcgctcggt ggcgctcgac accgagggct    22500
tcaccatgag ccagtgcgac atcaccaagg actggtacct gatccagatg ccacgaact    22560
acaacttcgt ctataacggc tatcgattct ggcccgatcg tcagtacttc cactacgact    22620
tcctgcgaaa tttcgacccc atgacgcgcc agggacccaa cttcgcattg cccgcctct    22680
tcgacctcgt gtcttacacc cctaccacgg acaacagcgg acagcaggct agtcaggaag    22740
ccgtgcgcaa caattctggg tttatcgccc cccgctcctg gcccgtctgg agcgctcacc    22800
agggcgagag ctggcccgcc aactggccgt acccgctctg cggtcagcag gccatccaac    22860
ccggacaggt cctcagctac aagaagttcc tctgcgacaa ctacctgtgg accatcccgt    22920
tcagttccga ctttatgtac atgggcgaac tgacagatct gggtcagaac cccatgtaca    22980
cgaacaactc gcacagcatg gtcatcaact tcgagctcga tcccatggat gatcccactt    23040
acgtgtacat gctctatggc gtgttcgaca ccgttagggt caaccagccc gaacgtaacg    23100
tgctagctat ggcttacttc cgtacgcctt tcgccacagg caacgccgtg taaaccctta    23160
gagcgtcggc atgacgggga ccacggagtc tcagttgcgg gacctggtgg cagcgatgca    23220
tcctcgtcac cgcttctctgg gcgtgttcga tcgaaccttc cccggattc tggacccgga    23280
acgcccgcg tcggctatcg tcaacaccgg ctcccggtcc tctggcggca tgcactggat    23340
cgggttcgcg tacgacccgc agtaccggcg ctgttatatg ttcgacccct tcgggtggtc    23400
cgacaagaaa ctgttggagt tatacaaagt taaatacgac gcgatgctga aggccaccgg    23460
cctgagccag caagaccgct gcatcgagct ggtgcgctcc gtgcaagccg tgcagtgccc    23520
gtgctcgggc gcctgcgggc ttttcagcgc gctcttcatc gcctctttcg accgctaccg    23580
acggagtccg atgaacggaa accccatcat cgacaccgtg gtcggcgtca accacgagaa    23640
tatgtacaaa ccggccttc gcgagatcct gcaccggaac caggagcgca tgaacgcgtg    23700
gttcgcgcgg aataatccct atttccagcg tcacgccgag ctcctgaaac gcgaaacggc    23760
aataaacacg ttaccacaga atcacgtaca acaagcatag cgactccttt attgtgaaag    23820
gaaggcaata acattcgtt actctgaacg aacgtctctc tcttgttgcg tgcgtgcgtg    23880
cgtgcatgaa tgcgtgctcc ccttaagccc gcgtaaagca ctacgcgaat ggatcggaat    23940
gggacacggg acagacggga gcgatgactt ccgttttgta ggcgtacttg tcgttccagc    24000
ggaactcgcg gacctgcgtg gccgcctccg tgcccagcgc ggtggtgatc agctcgttcg    24060
cgaaaacgta cgcgtagcgg agatccatgt aggaaatgcg ccacgagcag ctcttctcgg    24120
tgcgcctctg cgcgcgactc gaacccgcgg ggttggaacc gccgggcgcc tgcgggttgc    24180
aacaggtgta caccatcgtg tgcgggtgct tgtggtgcgc cttcatgtcg gcgcgactct    24240
ccagcatatc cttggtgata tcgtcggtgc cgctcagctt gtaggggtc atacggcata    24300
tctgccgccc gctgatggga gcttcgcaac cgtaattgca gttgcagttg gtcgagatca    24360
acacgcactg ctcgatgcgc gagcgatccg cgttcgggta cagcgccatg gtccaactca    24420
ggtcgtgctt catggcgctc agagccttct gcgcgtccga aaagaccatc gcgcagctcc    24480
cggtcgcgtg cgggtacggg aagccgttgt gctccttgtc tttcgcgcat accgcgttgt    24540
tgtcgaagcg gagcaccacc acctgccgcc gaagcggtt cttctccacg cgaccgccct    24600
gctcggcgat ggcgcgcttg ccggcttcgc tggtcggatt caactccacc gtgcgaggct    24660
taaggctcat cggaatgccg tgaaagcact tcggcatggt ggcgcccttc cagccgtgtc    24720
```

```
gccaaacgtg cgcgcctccc ggtacgaact tcggttccaa cccggctaag ttgtaaatca   24780
tggcggccaa aaacctgccc aactgcccgt agaaggaatc gaagctggag aaggtgagtc   24840
ggaactcggg gtgccgtcgg cgcataaaga gaccggcgac cttggtccaa atggcgtcca   24900
agggctcgat ggtgcctccc tgccagcgca tatcgagaga ttcgcacacg gtcgtcaggt   24960
aggccatggc cttttgcgcg ctgaaagtga cgggatcctc cgcgagggcg cccgccatcg   25020
ggccgccggt agactggaac tcttcggtgt cgcttttgag ctcctgctcc gcttcgagaa   25080
catcgctatc cgcgagctcg gcggtgctgg tcgtcttctt cttcggcgga gggcgcttgc   25140
cgcgctgcgg cttggcgggc ggcttcagtt ccgccattaa ttccagctcg gaatccgagt   25200
cgtttaggca cgcggcctgg tgttttcgct tctcgccggg catttcgagg gagcgcgagc   25260
gtgagcggtg agacgtggac ggtcgttcta cggcgtcgtc ctctgaactt gaaaagcccg   25320
ggtcgttagc tatagacctt ttcaggtcgg tcttccgacc tataggaaag cggacacgcc   25380
caaatccgtt agctcctccc atcgtagcag tggcggggaa attaaacccg aagttgcgca   25440
ctacgcgctt agtcgcctcc tacctcgcgg accgcggatc gtcgacatct tcctcttctg   25500
cggcgaacgg taagttcgaa catccgactc cgcttccctc tcgtcctccg agctgaacgt   25560
cttcgttagc ggctctctgt aggccgcgtc cctctggagc ttcttttttcc tcttggtcgg   25620 tgagccgtac gaccggctcg tcgagagtct cgcgcttctc tcgcgctgct cttccgcgtc   25680
ggagggcatc gggtcctcgt agtcgctgtg ctcgcttcgg cttgaatcta tctcgacttc   25740
cattgctctc taggggacta aggcgcacat aatcatgatg tcgaatccgt cgggttacgg   25800
acagctgaaa agcttggcga cagtgggctt agtgctgcgc agcgccctcg agcggtttcc   25860
gtggaccgat tacgtaagtc atcttcgcga ccacgttagt accacctatc gcaaagagct   25920
gccctctagc gcggagttag tcgagatcga gctggacacc ctggccgaga tactcattga   25980
ccgactgggt caagaaacgg cggtgcttag cgcctacaaa agtcttggaa gaccttatcg   26040
aacgcgataa ggaagcgcca aaagaggaag cggaggcgcc gagtgggaaa gtacctaaac   26100
tcccgccgaa ccttccctcc attgttcccg aggagaacaa aagccccgag gctgacgtcc   26160
gaaaagacgt gggcgagatg gaaagcaccg ccgacgggga taaagcccgt ggcgaggagc   26220
ccgtagctga acgcgaggcc agcgacaccg ccggcgccga cggcgagttc cccgcaccgg   26280
aagacgagca tccggacgat ggggaaccgg atgaaccggc cgacagagac gaccgatcgg   26340
gcgaatcgga cgcggatagc ggttactatt cggcagatgg gggacgcgat gcagagtgcg   26400
acggagaggg cgctcgaccc gacacccccta cggacgagtc tagcgcgccg actactccat   26460
ccacagcagt gcgacgctca tcgggcgagt ctagccccga tcgcggtggc tgctttagcc   26520
actctagcga ctctgagctc ggctgtgcta ctgagactcg cgatccgttt gctgcggggc   26580
tgcgcaagtg catcgaacgg caagccatga tcctaacggg agccctcaaa gacgcgcagc   26640
tcgacccgcc cctcgacagc atgccactta ccgtagacgc ggtccagaga cagttagagc   26700
gctttctctt caacccccgac ccgaaagtgc cgcgcgagca cgtagaggct cgctacaact   26760
tttatccgcc cttcatgacg cctaaagcca tcgccaacta ccacatcttt gcggtaaccg   26820
cccccatccc gcctagctgc aaggccaacc ggagcggatc cgaggtgctc cgtgccgcgg   26880
agaacgctcg cttcttcaaa cgcttacctc gctggaagca gggcgtgacg gtcgacgacg   26940
gtctgggaga cgaggtgtcg cctataacag agctgaaaga cgccaaatta gtgccgttgc   27000
gcgatgacac ctcccgtctc gagtgggcca aaatgcgcgg cgaacacgta cgctattttt   27060
```

```
gctacccctc cctccacatg cctcccaaaa tatcccgcat gctcatggag gtactgctcc   27120
agcccttcgc tcaagaggta gcgagcggtc ccgagcaaga agaccccgag cccgtcgtat   27180
ccgacgcgga actggcgtgc atcgtcgatc cggagggcgt gatgcaacca cacgcgctag   27240
ctagagcgat agaggtcaga cggcgcatgg tagcgcaggc cgtccgctat accgctcagc   27300
tagagcttat ggaacgcgta ttccgagagc cttcctcgat caaaaaggca caagaagtgc   27360
tccatcacac cttccatcac ggtttcgtgg cgctcattcg ggaaaccgcc aaagtcaatc   27420
taagcaacta tgccaccttc cacgggatca cgtacaacga cccgctcaac aactgcatgc   27480
tagccaagtt gatggaaggc tcggacaagc gagattacgt ggtggacagc atctacctct   27540
tcttggtgct cacgtggcaa acggctatgg gcatgtggca gcaagccatc caggaggaaa   27600
ccatcgaggc ttatcgagag gcctttactc ggctccgaag agctatttac gccctcgaaa   27660
cacccaccga gatctccaaa gccatcgtgg acgtgctcat ggacggagac cgactgtgcg   27720
ccgaaatgcg caaagcgctc cccaacttca ccaatggcag ccaaatcagc gcctttaggc   27780
agtttatcat ggagcgcagt aacatcccca ccacagccgc cccccttccta ccctccgatt   27840
ttgtgccgct ctccttccga caagcccagc ccctgctctg ggaccaggtg tacctcctcc   27900
aaaccgcctt tttcctctgc aaccacgag gatacctgtg ggagcccgag gaaaccgaga   27960
atcccaaccc tcgcgatcgc acctactgtc cgtgcaactt gtgcagtccg caccggatgc   28020
cccaacacaa cgtgcctctg cacaacgaac tgctcgccat caacacgttt gaaatccgca   28080
cggacgacgg caagaccttc aaattgactc ccgaactgtg ggccaacgcc tacctagaca   28140
aattcgaacc caaagactac cacccttccg aagtggtgca cttccctcaa cacgaggaag   28200
cgttctctag agacctcacg gcctgcgtca ccaaaagccc cgaaatcctc agtctgattc   28260
gtcaaattca ggcttcgagg gaggagttcc tcctcacgcg gggcaagggc gtatacaaag   28320
accccgacac cggcgaggtc ctcactccgc agccagatct ccaagctgga gcagcccggc   28380
gacaagctct accaaccgct tacgccgatc acgccgagg agctgcgacg tcggcagagc   28440
cttctcgagc tctacggcct accagcgtcg caaccgccgc cggcgaaacc gaacacgggg   28500
gtgctcttca gcgcgctatc ggctcggtcc aaccctccgt cgcaggagca actcctcatg   28560
gcccagagaa tggtcgacct gaaggccagg gcttcggaac ctccggagcc cgaaatctac   28620
aatcccgagg aggcgaccga gtccgacggc gaaactctag gcagcgagga taccgatacg   28680
gaagaggacc agatgagcac gatctccgaa gaggaggagg aggaagacga ggcgtattcc   28740
gcggatctgg ctggggaaga caaggagaac agccccctc ccctacgat tcccccaaa    28800
cgcagccgaa aagcatcctc cgtcgccccg tccaggccc tgacgagacc tcccctgcgt   28860
accaacaaca ccgccaacac gaccggcacc gccaggagga tccgtccgca gcgcctaccc   28920
gaccgagcac cccgaggtaa ctaccggagc tgggcgcgct atcgggtggc catttgtcag   28980
gcgctgcggg atacggtgtt cgatagggtt caggcggccc aagtgcttaa aaatacacgt   29040
caactgtacg tgcccgcctc cgtgctggct tactacgcta gaaaactact agctatgacc   29100
gacgactctg cttttcaccca cagctgcgag ggctcgcaac gctagccgaa agcctgctgc   29160
gccacctaaa cctagaaaac ccgcttcggc cacttcttcg attctagaaa aaccgatacc   29220
ccagcacatc gcggaccttc gcgccgaggt tctcgagatc ctgctcaaga tcgaacagta   29280
cgctcgaaaa aaccccgaac ggcgagtttc cgtgcgcaat cgcacccggg agagcatcac   29340
tcgacaagtg cattacacca gctccgagga agcactcacc aggctcaagg cggacgcgga   29400
aaaaatccta gtcgcctgga gtggcagtgc ctagaccggg gacatttata ctgtcgaaaa   29460
```

```
tgaacctctt gaacgccgca cccacccctt acgtgtggaa atacaacccc gtgaccggta    29520
aatgcgccgg cgcccaacag aactacggcg ccactatcga ctgggtgttg ccgggcggta    29580
acagtttcgc ttacgcggcc gatgagataa ggcgccgatt cccagaaccg gcagtcacga    29640
gagcaattac cgcgcgcttc gaggctgagt cagaccaaca gccctacgcg ggcccgcacg    29700
aaaccaacat tatcacggca gatgtcgtgc gaagcgggc gccgcccagc gcggtgtacc     29760
catttgaccc cagcggagtc caacgggtgc aactctccgg aggcatgatg ggaggtcgca    29820
ccgagggcag ggtgcaatta tcgggcggac tgaccgaagg tcgcatgcaa ttagcgggcg    29880
gcgccgccgg gaaactaccg acccgggcgc gccctacttt acgaccgcct agatggtgcg    29940
gtaccaccct gaccggcaac ggtctcccgg ccgattaccc cgaaatgacc ccggacgcgt    30000
tcaagtacta tctacgtgtt caaggtccca gccaggaggt ggacgagccc ggagtcatgt    30060
cccagcgccg attcatgacc acgttcctcc cggccatggt cccccacccct ttcgacagcg    30120 aatctcccga cgccttcccg gcctacttca gcagcgtcta caagggcacc aacgctttcg    30180
aaccggtgtt ctggcagggt taaggggcgg tacttacgcg ctgctgacgg taatcggtct    30240
cggaataaag ctcttgcatt tccgaagcgg aaaatggctc cttctgggtc attacgaccc    30300
gctcgccgcc ttcgctgtgt acgcgcgctc taaacttgcg tctcaaccaa aacacgaaac    30360
cagggttaag cggttcgtcg aaccgtaaca tagcctgatc gtttattttt aaccaatatc    30420
ttctaggctc cgccatgtcg gccctaatcg cctccgcagc cgataccgtc tccgtcagcg    30480
gaaaaaaacg accccgcagg gccctatccg aacctatccg gtacctttcg gagggtgacg    30540
agcgtcgaaa acccaaacgc gcgccaccgg ccacccgcgc gaatggtccc ctcctcgatc    30600
tggtgtatcc atttgacttc aatgcggggg gaggtggcag cggtggcggt ggtggtgggg    30660
gaggtggagg tcagcagatc gcggtcgacc ccgatgggcc gctcgaactc actggcgacc    30720
tactgacccc caacaccaaa acgcccattt acgtcagcga tcgagcggtc agtctgctca    30780
tcgatgacga tactttggcc actaagcaag tcaacggggc gctcatggtc aaaaccgcgg    30840
cccctctaaa ctcgggcact ggcggcggcg tcacgctagg cttcgacccc cacaccatgg    30900
cactggattc cgttaccggg gtgctcaaag tgctcgtcga ctcacaggga cctctgcaag    30960
ccgacaccgg aggcatcact ctccagttca acactcaaga cttcgttgtc aacaatggca    31020
ccttagcgct agcctcctcg gtcggtccga cctatctgag cccctttgca acctacgaag    31080
tcacgcccgt attgggaata tcgcagagga acggcaacgt aaaaagcaag ggcttgcaaa    31140
actggtccat aggctattac atctacatgg tgagctcggc cgggatagtc aacggactca    31200
tcaccctgga gctagcccag gagctcacgg gggcgagcgg agaaaacagt ctgaccagcg    31260
gcctcaactt tacctttgtg ctcagcccca tgtacccgat agaaacagag gtgaatttgt    31320
ccctcatcgt gccgcccacg gtctcaccga ccaatcaaaa ccgcgtgttt gtgcccaata    31380
gcaaccagag cgacgtgggc tatctcggcc tgccgcctca gaccaaggac aattggtacg    31440
tgcccatcga ctcgcccggc ctgcggctcg tctctttcat gcccaccgcc accggaaacg    31500
agaaattcgg acagggcacg ttgggatact gcgccgccac catccagaac acgcccagcg    31560
gaaccacgcc atcggatgcg ctagccttca ctgtctcgct accgcagact tccggctcca    31620
actggtttga ccagtacgcg cccgacactg tggtgacgac cggtcctatc ccttttttcct    31680 atcagggtta cgtctactcc cccaacggga acaaccatgc tccgagcccc taaaagaaga    31740
cattccgaga ccgaagcggg accttccccg gctccaatca agcgcccgaa acgcatggtg    31800
```

```
agagcatccc agcttgacct ggtttatcct ttcgattacg tggccgaccc cgtcggaggg   31860
ctcaacccgc cttttttggg cggctccgga cccctagtgg accagggcgg tcagcttacg   31920
ctcaacgtca ccgatcccat catcatcaag aacagatcgg tggacttggc ccacgatccc   31980
agtctcgatg tcaacgccca aggtcaactg gcggtggccg ttgaccccga aggggccctg   32040
gacatcaccc ccgatggact ggacgtcaag gtcgacggag taaccgtgat ggtcaacgat   32100
gactgggaac tggccgtaaa agtcgacccg tccggcggat tggattccac cgcgggtgga   32160
ctcggggtca gcgtggacga caccttgctc gtggatcagg gagaactggg cgtacacctc   32220
aaccaacaag gacccatcac tgccgatagc agtggtatcg acctcgagat caatcctaac   32280
atgttcacgg tcaacacctc gaccggaagc ggagtgctgg aactcaacct aaaagcgcag   32340
ggaggcatcc aagccggcag ttcgggagtg ggcgtttccg tggatgaaag cctagagatt   32400
gtcaacaaca cgctggaagt gaaaccggat cccagcggac cgcttacggt ctccgccaat   32460
ggcctagggc tgaagtacga cagcaatacc ctggcggtga ccgcgggcgc tttgaccgta   32520
gtaggagggg gaagcgtctc cacacccatc gctactttg tctcgggaag tcccagcctc    32580
aacacctaca atgctacgat cgtcaattcc agctcgcacc ccttctcttg tgcctactac   32640
cttcaacagt ggaacgtaca agggctcctt tttacctccc tctacgtgaa actggacagc   32700
accaccatgg ggactcgccc tggggacaac agctccgcca atgccaaatg gttcaccttt   32760
tgggtgtccg cctatctcca gcaatgcaac ccctccggga ttcaagcggg aacggtcagc   32820
ccctccaccg ccgccctcgc ggactttgaa cccatggcca ataggagcgt gtccagccca   32880
tggacgtact cggccaatgc atactatcaa ccacccagcg gagaattcca agtgttcacc   32940
ccggtggtaa cgggtgcctg gaacccggga aacataggga tccgcgtcct cccagtgccg   33000
gttacggcct ctggagaccg ctacacccctt ctatgctaca gtttgcagtg cacgaactcg   33060
agcatttta atccagccaa cagcggaact atgattgtgg acccgtgct ctacagctgt     33120
ccagcggcct ccgtcccgta agcgcgccct ccccaccgcg tgacaaataa agagtcatga   33180
acgttgattg cttttattga tcgtccattt gtccgaaagc ttctctcctt tgttcccgcg   33240
tccaatcata caacagattt acgctttcta aaaaccaatc gggtgcgtaa aagcgagtaa   33300
tgttgtgttc cacactgatt tccatttttgc gcaaatagtg acaggggagc gccccccaagg  33360
ctccgagctg ggatactacc atcaggaatt cggcccgtct gtcgataggg taaagaggta   33420
catgaatcat catgcccacc acgccctgta ggtggtggac taccatcggg ccaaaggagg   33480
aaaacatggc acacgcccac gcgcacacaa aatagttccc ggctacccg tagtcctccg     33540
aaagtccctc gcacagctta tcccccgtacc tacagtacac cccggttccc acagacaagc   33600
ccaaattgcg caaaccgtaa ttgtgacaca cacagttttt gaccaccacc ctcattctct   33660
ccatgcaagc aagcaccatg ttttcattcg gattggctgc ggcctccgcc gctgcgagct   33720
cctcctcttc ggcaaggggg gcctcctcca tcggttcggg cgctgcgtca cgctcctcca   33780
tctctacacc tgggtctcgg tgggtgcaat ggaagtgtac acgtggtcgt aagggtcctc   33840
gagttcagag tatgggttca caggtacagg cggcagcggt cgagacgcgc ctagcccgat   33900
gcgcaaacta gagtacagcg gattggctga cagtacccac ctacccgaac cccgccttct   33960
gagggaccgg acctctgggg gcgtgcaacg ggccttcgga acctcaccag tccactccct   34020
gataataaag tacagcacaa tcaacaccat taaactgctg gtgagaaaca cggttatgac   34080
atagaacaac acactgacgg agcgttccac aaaaaggaaa ctgacggaaa tgcaggtaaa   34140
gtagagaccg accgccagca agccgatcag cagcagcggg agatatctcc gtcggcactc   34200
```

```
ctatttaaaa aacggagatt tgcgattgtg agtcacgcga gcgcgtctgc ggtcaaaggc   34260
caacttcaaa caagccattt gcgccagata gaacaagttc ataggagact tgacctcgca   34320
ccgatcacac ccattctcgc aatcacagaa gggaccgtgc acatgcataa accactcttc   34380
catgtcgcta taggtggcgc gcctgtgcgc tggtaaatag cacaccccgc gaaacacgat   34440
ttccctgtac ggtaatggca caaaatcgac cagcatgctt ttcgtgcata ccgattgagt   34500
gatacagcta ccattacctc gaggacacac cagagtcatc ctcacattgg ttttgcaaca   34560
ttctaggtaa ttgatgggca cctccataaa gggaacacag cgcggaactt tagaggtgga   34620
aatctcaaaa cacatggtgc gcagggccat cttgcagcat accatgctcc ccaaaaccaa   34680
tccgctcggt acgaaaataa aatcggtctt ccttttcctc tccatccacc tgaccatggg   34740
agcccttatc tcgggcggaa cgttaaaaga cgtcgggaaa tgaactgcaa aaattcccgc   34800
ttgtcagaag cggtgagcgg aatagcggcc tgaaagcgta tatcgcagtt caccactaag   34860
tgaactccgg accgcaggcg aagatagcgt gaacacctac atcccaccgc tacgtaaatc   34920
gatgaatgta tgtagcgcaa aaactcatct ccgttaaaag tgttcagatc caatatcgcc   34980
aaagtcaggt gatattctat catcctctca atctcttcct gatggagcac gataggctcc   35040
cgaggtgggg gtaccaatac actgaacgaa caacacccgc attccatttc aaaaccgcat   35100
ccgcgaacca gggccagaac gtcctagaaa tagtaataag ctctactcag cactctcatc   35160
agaatcaccc tccccgaacc cgaaaccccca ctcaccgatt cagcacacag aggcatgatc   35220
ttacagcaga ccgaggattt tatttacagc acggtctaga agaacaaata ataacaacg   35280 ggtcatttac gcggctccaa cacagcctat cggaatgcgc gacctcatat cacgggataa   35340
cataagactc aggggtggcc tgtatactaa tcccgtcact gacgacactc ggcgccaccg   35400
agtctgaact cgcattccta atgtcgcgcc attccaccac agcggctgtg tcaggagccg   35460
cagtgctggg agctctcgta ggcggcgctt tagacacgtg acaggtccac tccaccactt   35520
caaaagcata gtcgaagaag agggtatacg agccttcctg cttgaaagaa aattggaagt   35580
tgccccttct gcgatccgcg cgcaccgtca caaaaggtct cgcctcccta caaatgtccc   35640
agtaggaaaa tacggcacgc tttaaccctc cgtccttcac catgtcgatt ccgaacaact   35700
cgaaaaacca gtgtttcgga gacaattcca aatccaccct ggcgccgacg gtcacgttca   35760
tctcgctcaa cttggaggtc aatttcccgc tcattcccgc tcggttacgt aaacaccgtc   35820
ccggtttagg tggtacctgc atggtcatac ccgctccctt cacatccagc atatctctat   35880
aagccggcat catgcgagcc tcaccgacta acccacaaac actgctataa gcagtgaacc   35940
atttgcactc cactccctgt acaaaaaaac tactcatcgg cacggcacaa ttgtcatcct   36000
cgcatccgtg ggaccacatg acatgcgcac tcaataagat agcgcggtcc gtgtggttca   36060
cgacaaaccg gcttagagac tccttaggaa tcaaagccgt ttcgagttcg tattgcgtac   36120
cgtacgtaat catctctcta aacaccctac gactaccagc tgtgatgcgg gtgctggaac   36180
cggaatagga caggataaca acagctccgt aaggagtcac cccatcacct acgtgggtgg   36240
cgtaccaagc ggtttcggaa tcgaagtaaa gcgggtaacg ataatccttg ctaatgctgt   36300
acccgttcca agccgtgtgg aaatgtccgt aatacccaat gggaggtctc gaaacagatc   36360
ggaacatggt catagctcca agcacatcga gggacctcat aaacacgaaa atggaagaga   36420
ggtgactgca gacttgggaa tacgtcagcg gcgaggatag cttaacctca atatgctcac   36480
atactgtctt aagataataa ttggtgccgc aaatggtctt gtaaatggta agggactttc   36540
```

```
ggtagtcgca catgtcgctc tgtagaccgt cccaatctgt agtgatgtat tcgtgaccga    36600
acagtctagg attggaaaac ctattcctat tactagccag taccactaca tacttggcat    36660
ctttactgct caaagctctc tccctattat accgccacag actggtactg acaaatgcag    36720
ggctgggact aagcgccact attctgtgac acttccttcc gtgcacttgg taaaattgcc    36780
gacacaccgc cgcgcagacg tgcgccccca agtcgtgccc tatacaatgc atcctcttgt    36840
tttttggaaa ccgtcctaaa aactctgtca cattcactat catcacctcc tgtataaggt    36900
ccgacatcct taaaactcct tcctgtctcc acaggagtgt taccactcca gtatgtggag    36960
tcatcttttg gtggtacctc aataaatggt caaataaatt tggagcgaac atgccgggca    37020
ctaaaaagat gatgtccttc gaatggctaa acccgtcctt gatttcatca aagtttctc    37080
cgatgcatgg agcactttcg aattctccgc ggtcgtacca tctcagaaca gccaattcat    37140
cgctcaactc gtctgtcttc ctgggaggac cctcctctct ccactccgcc accgagcagg    37200
gttcggagcc gttgaaggta cacttccaac gggaaccatc ttcaaaagtt gatccggaag    37260
gaagaccgca caaggcgatc aaaacaaact aaaaaacacg caccataagg tcacatgcaa    37320
tcgaccctaa cctattctcc caaaatgata ctcaccacaa tcacgcaatg catagagtac    37380
ggctcagagg ctccttctcg agtggagtac tagccgggcg aataaactcc gatccgaaca    37440
tccgccatat aaaacacagct ttcgtaaaat attaacaaac actaacttcc tcattgaccc    37500
gcttaattgc cgtgtcagcg cgcgcctgaca atgagtcatc gatgagtcat cgctaagtca    37560
acaatggaac tttccacttg ctaacaaagc gaaaccagaa gttaatcatt aacgccacac    37620
ccatgatgag tcatcaccag taaaccttaa aaggacggct tccagccccg cagcgaaaag    37680
caaccttact tccaacacga gggctctgcg gaaccatggc cgaagagtgg ctcgaccttt    37740
tccacccctc cacttcgccg aatccagaag agagaaggtga ggacatgtcc ctcgaaaccg    37800
aatgccatgc ccctcttcaa tatatttcca tgctgtcttt tgatgacctc ctggcggctg    37860
ccggtccccc ggaatactct ccggaagaga accaggaaac accgccgctc gaaaccatag    37920
aggtaggaga catcatggcc gaactcggta ttccgataga gggacctccg accagccctt    37980
ccgactcttc ctccagtttg gattcagtac ttttctccgg tgtcgacttg tatgacttag    38040
actataccat cgtctttttcc cgactccgtg agttttggca atcgcacggc gcatacttaa    38100
aaaccgtagc ttcactcgag tgcatgcaaa acgacaggaa atttcaggaa gcatactgtt    38160
cactggtgag aatgcacgct gtttccgaag atgccaaaga gcatctcaat gaactcttac    38220
tagacgaatc caactaccaa cattgcgaac ccctcaatga tatgttggac ttgggattcc    38280
gatggctcaa tgacctaaaa ggaggaatgg agtggtgcat ggacactgcc ctggatcgcg    38340
catcaaaagt catgcctctg actgactatc aaccacaata aataaatttt acattaaaaa    38400
ctttctgagt aagattttc gaacctgaaa aattctaagt gcggttaatc attaatcaag    38460
ttaaatatta aactctagtt aaatattaaa ctctagttaa atattaaacg ctagttaaat    38520
attaagctga agttaatgat tcatccgagt taatggataa ccttgagtca atgattaact    38580
ctggttaata tgtaactcgg ctaatgatta acatgggtta accattaaca tggtttaacc    38640
attaactata gttaataaat aactctaagt taataagtag ctagtgacgt acgattgacg    38700
tcacggtgac gtcggtgttg ccatggagat gtaaccatgg taatgttaaa cattaaactg    38760
ctgacaccag tggaattttc catgttaacc attaacatgg accttgtcct gtttgtttat    38820
tcaccatggc aacataccat atatggacat ccgactccgc ctccccgtt atacattaac    38880
gatggcgtga taggcggagc tctctcccat tggctatcaa tgatgtcatg tagttacaca    38940
```

```
ttagcccgtt caacctatat aggtagacca ggtaggcagg ttcagacaga cagaccgggg    39000
accagcagac tgaacggagc tctccactaa accggtaggc ctctatattg aatcgatgaa    39060
taaataccga atcaactcaa tattatgatt ttccattgaa attaatggtg attttcttca    39120
atcaaactcc cacccccctt ggcacccccc tgtacacccc cctgtacagg cgaccacccc    39180
ctatgatcac ccccctgtac agccgaccac ccccatgac cacccccctg taccattaca    39240
gccaatggga tccatccat tgacatcaca tgatccccgc tggccctatg aggtggctac    39300
catatccttc accctattgg atcccatgcc gaggggcgga gaagatggga ggcgcccgta    39360
cctcgacaac caattggctg aggcccttca gttcagtccc gccctcactc ccgaccaatc    39420
caatgcattg gagttcacca cgtggctcgt gaaggggcgg agactcctcc ataagggaaa    39480
gcagtaccgc ctctacaata tggcggcccg gatatgcagt atccaccaat gggagagaag    39540
tgaggcccag ctgaccatgg aggccgtagc caatgggctg tgggatctgc cggatgaaat    39600
actcgggagc cccctactgc acaatactgg tatacacacc tggggctggg gggtccccgt    39660
cactaccgag atcagcctga agatggtgct aaagaccctc cgtgtcaata ctccattcaa    39720
ccgccagggg gagatgccta taccggtatc caaggaggtc catgtagaag ccccccaaca    39780
ttttgaagac atgctccagg gggtcctgac gaccaccgat ctaaaaaagc atattcctag    39840
acccatcttt tcccgatttt ttaacgaaaa accctcggtt tgggcctata agactttcaa    39900
atattcggcc ggtgaagaaa aatggcgagt ggtggtccct accgagggtc cctatggggg    39960
tcctaagaac cctgtttctc tgcaaaacct cgcgaaaatg ggtgtgttgg aaaattgtct    40020
aaaaatgaaa agggcggggc tacggttcat gccatattaa taaaccaatc agaaaacaga    40080
aatacgactc ctcctctttg tgggcggtac tggggaacac caatagaaat agagactccg    40140
cctatgaggc gtagacttag ttactgaata acttttcgga cttagaaaaa ttttcacctg    40200
cttaatcatt taccaatggg tctacgtcac tatgctccgc cttttaactcc gcctatagct    40260 ccacctctct ctccgccccg atggactttg gactttagat cacatgactg ctacgtcacg    40320
gagggaggag cttcggactt agaaaatttt tcgctctatc aatcattaac ttgaggatgg    40380
actttgaacc ccacgtaagc gacggggagg agctaacgtt aatcttcaac tcggactttg    40440
cccggaggcg gagcttcgga cttagaaaat tttccactct atcaatcatt aactgggcaa    40500
cggactttgg cactgacgtg cgcaaagagg aggttctaaa gttaaacttt aactcgaact    40560
ttgaacggag gcggagctcc ggacttagaa aaatttttca ctgctataat cattaaccaa    40620
ctgaatcaca tgacacagag ggaggagact gcgagtaatc acctttaatt attaacagct    40680
cagtcaacaa ttacatcatc agcggtacga agtccggtac atacacgcca cgcccctaga    40740
cattgaaatg cttcctcctt cacgcccag cgccccatgc ggtactcctc gggacaccac    40800
tgattgtcat acagcttcaa ccacacctgg cacggagagc cggtatctct ataaaaaacc    40860
agatgcagga accgtcgcat atcactccga cacttctcca actttccctt agtctgatcg    40920
gaacaatgga tacaaattaa caaagttgca tgacattcgc acacggaaaa ctcttgcaac    40980
ccgaacatgt acttcagagg acaacattca ggactgtact tctcaacaag tttagtccat    41040
atgaacttca gtccacggtg aacacatcta aacacctcag gcctctgaca ccattccgga    41100
actgccgctc cgaacacaag gtacattgtc atctgaaatt taaaccattt attcatacat    41160
gcactcgtaa atacaccccct ctctactgcc gacagcttct gctgttacac aatattcacc    41220
caagcggaac tcttccgcgt acccccccgtt acgcaaaagg catacaccct taagccactt    41280
```

```
ctcgctttca tgtggatatt taccaaaaaa caaacacttg acagccaagc ccactccctc   41340
cgcataagca cttccaaaat ctgtacaggg caaaaaacat tcgatgcaaa atccatcttg   41400
aaaaggatag agataaaaga aacccgttac tgctccagga aacaccttgc ctaaatccaa   41460
tttctcccaa gcattaatta catcacgacg aaagtcatga acattgcca aattcaattc    41520 ccacaagggt acgcgcaaca ttaagtaacc caacattacc caccgcacac gggaccgcca   41580
aaagagtgct ctgcagattt tcctgctctc tactaattat agttttgcct ctttaatcat   41640
taaccaagaa cgtcatggaa aatttcaaaa cacaaggtca cttccttatt acatagataa   41700
gatatcacgt tgccgatcaa aggtcacttc cttattacat agataagata tcacgttgcc   41760
gatcaaaggt cacttcctta ttacatagat aagatatcac gttgtcgaac aaaggtcact   41820
tccttattac atagataagg tatcacaagg tacatgaatc actagtaatg gtcctgaatc   41880
agcagtttcg atcacgccat cgccagtcaa tcattaaccc gagatcccta taaacttccg   41940
gcagactcgc accacggtac tccatccgaa gactgatcaa gtctgaagac aatcttctct   42000
tcggtgaaca gtcctgagga aaaacaccat gcgggtaagc atcattcatc cattataccc   42060
cttttactct ttcacctaac ctcgctaaca tagatctcct ccctctcggt ccacagctgt   42120
taaccctact agccctactc gctgcatggt tactaaatgg ggatgctgcc gtcaactcca   42180
tacagaacaa acccacggtc cctaccaaag gacccatggc caacttcagc ccggttcgcc   42240
atgaaggtca catcaattac ttttggtatg ggcaacacgg catggcaccc ccgagaatcc   42300
atggccctct ccacgacaat gacatgatct actggagact ccgtgaccgt ggattcctga   42360
gaggcggaag ggaaaagaac ctgatcctat tagtccatgg atggcacggt ctccaccgca   42420
cctttgatat cttcttcaaa ttcctccgct tccaccagaa gatgacccca gacgtaggcg   42480
tgctattagt cgattggggg gtacaaggcg ccgataacct cattctagga gatgccgctt   42540
accacgccgt cactatcaat atcgacggat tgctcaagaa cataaaccgc accgacttac   42600
actgcatagg acactccttg ggggctcatg catgcggtgc aatttgtcga agattcaacc   42660
agctccaaaa tagaaaatgt actagaattg ttggactcga cccagcagga cctctcttca   42720
aaaccaactc tccctatcct tacctcacca aagcccgtct gtctaaaaaa gatgctgact   42780
atgtagctct ctttatgacg aaccgccgga tgatgggact ccacgaatta aaggggatg    42840 agtacattac cccttacata gatggcacct atttgaatca ctgtcccttc attggcaaat   42900
ggacaggcac tatcactgcc gaaaattacc aaggaagaaa ggtcacggaa tacatcgact   42960
taggtacggt ggccaaatcg ggtgtaatcc cacacaccat ggatgcatgc tcacacctca   43020
tggctcctgt tctttttcatg gtgtccctag acacccgtca aggcctacct gcattccggt   43080
atgctgagaa ccctccccaa gatcaaggtg ccatgcatac ggtttggaat gggtacacca   43140
tagggaaaga ctaccagtat ccagcctatt tcaaacacga aactatctgg cttagtacac   43200
tcaccacgga tgcaaaccag ctctcaccct tcgaattcca acacgaagat tccatagatc   43260
cctctttcat ggcaatggca attagcgaca agggatgcat ctcggccggc tcccatctga   43320
gctaccacta cagtgtcatc ccttacggaa acaaatacga tttggtaaca tccttcagcg   43380
cactctcccc cggaatggca gatacgcact tcctcgaggt ctacatgaac tacaaacact   43440
gtcccgtcta tctagcccga tttctgattc ccaaaccttca ccaacagcag ttacctagac   43500
ccaccacagc cggactctcg tccgaaatgt taagttgcag gaaacaaacc acttatacgt   43560
ggagctgcta cagaacatgg aagcaagctg tcctacccgt gtaccgccag caactcgatc   43620
ttacgggtga cggaaggcac aacatccaag tccctcccaa acatggatgt ctgaaggaac   43680
```

```
aatccaactt taccgatatg ttccgtacat acatgggcgc atatgaagtc ttgactgatc    43740
agactgttac agtaaccagc ttgccatcgc cgttcgaact catccgtatt gctctgagag    43800
atcctgcctc gcacaccatt caaaacatca tgacctactg ggacatgtgc gatcctgtag    43860
ctagcacttg tagcttcaca gtaaatcgag ctacgagaac tctcaacata acctgccccg    43920
acccgaagac ctactggatc tccttctttt accaatggga agaagtcttg ctcaagatta    43980
ctgtccatcc taaacccact accactacca ccactaccac tacaaccact acaaccacta    44040
ctcccactac cactacaacc actactccca ctaccactac aaccactaca ccactactc     44100 ccactaccac tacaaccact actcccacta ccactacaac cactactccc actaccacta    44160
caaccactac tcccactacg acctccaccg aatcaatcac agaaccgagc tccgcttgtg    44220
atgaagaaga agatgaagat tgttggttcg aaaaatatcg cgatcagata gaagttcctc    44280
aaaaggtaca actcccgttc aaagtagcga acaatgaaat gtcagaacca actactgctg    44340
ctactactcc ttccagccct gccgccatag aggaagaaag caacagcaga gcatctacac    44400 cacccctct tcaactcacc gtagccccag gtactaaccc ccctcttcaa gaattcctct     44460
gggcggaacc atcatctaaa gattccctcc gcaaggacca agactccacg gtcaccattc    44520
ctgtcaccat tggactctta gccctagtct gtctcagtgt tatcattgcc gtattcattg    44580
cccttagaag gagagggaga ggtccaaggc caacctttat tattgttcct ggaacaggca    44640
ataatactgt ataccaggaa actactgaaa tgttgtaaaa tttataacgc tataaaagtg    44700
cgtgactaca ataagataa gagcatgaat caactcggtg tccgcccatt cctttctcta     44760
tatattctga catgaacaga tttcagacag aacgacgact gggaggcgag aagagctccg    44820
taaagctaga caggttcccc tactggggta ctctagaaga aatagatagg tatgctaagg    44880
ctaatcgcgg aacagtgacc cccatcgggt ccggcaaaca ctttctagtt ataggagatc    44940
tggaaggtac cttacatgcg ggtcaacatt taaggaata ctgcgaagtg ctgtatctac      45000
cttccccaaa aagaatgacc atcattggca tagtggataa cgtcatctca ttcgcggatg    45060
gattgcaagt agtcattttg gtggcggaag ataaaaccgt ctatggctac gaagaagaca    45120
ctctccataa attagcatcc accataccag aattctttcg tatcggaatg cagaactttg    45180
gaaccgaagt atttcactgc ggttcccaca tccccccatt ggtaagtgca gatcccacac    45240
cctctcatta cttacctgat agataccta cacactatat tccagtccga ggaggagcgt      45300
cagcgtgatc ccgagataag gcggctccga gaagaagctc gaaacttcat atcagccggc    45360
gaaagaaaaa cagactaacc aaccgcaatc cgatccgaac atagccacgc aatggtgtgc    45420
ggatccactt aaaatagatt acgcgtatta ccagaaataa actgattgaa atgagaggca    45480
agagctgtgt cattatttcg cgttcgttcg caaatacgga agtccatcac ggatatccgt    45540
aatcgtcatt tgggtggaga ccatgagtca ttgatgactc acttaaacgg tttcggtttc    45600
ggctatcacg acgcgctgcg cgcggcggtt gtaagtgtgt caaaagacgc ggttatataa    45660
gatgatg                                                              45667
```

<210> SEQ ID NO 3
<211> LENGTH: 79
<212> TYPE: PRT
<213> ORGANISM: Fowl adenovirus serotype 4, strain FAdV-4 ON1

<400> SEQUENCE: 3

```
Met Ser Tyr Arg Arg Thr Val Pro Leu Thr Arg Cys Ala Leu Leu Asp
1               5                   10                  15
```

```
Ala Glu Asn Ala Asp Ile Ala Ile Ser Glu Pro Cys His Asn Phe Glu
             20                  25                  30

Ile Gln Phe His Pro Ile Thr Pro Arg Arg Val Phe Leu His Cys Phe
         35                  40                  45

Glu Pro Asn Arg Phe Trp Thr Glu Ile Leu Trp Asn Gly Thr Val Lys
 50                  55                  60

Gln Ser Glu Leu Asn Ala Ala Leu Glu Lys Ile Val Glu Leu Leu
 65                  70                  75

<210> SEQ ID NO 4
<211> LENGTH: 130
<212> TYPE: PRT
<213> ORGANISM: Fowl adenovirus serotype 4, strain FAdV-4 ON1

<400> SEQUENCE: 4

Val Pro Pro His Asp Lys Ala Leu Ile Ser Thr Gly Leu Ile Leu Ile
 1               5                  10                  15

Leu Pro Pro Gly Thr Tyr Gly Arg Ile Ala Pro Arg Ser Gly Leu Ala
             20                  25                  30

Ala Lys Phe Phe Ile Asp Val Gly Ala Gly Val Ile Asp Ala Asp Tyr
         35                  40                  45

Arg Gly Glu Val Lys Val Leu Leu Phe Asn Phe Ser Gln His Ala Phe
 50                  55                  60

Asn Val Arg Lys Gly Asp Arg Ile Ala Gln Leu Val Val Glu Arg Ile
 65                  70                  75                  80

Phe Thr Pro Glu Leu Glu Glu Val Ser Ser Val Asp Asp Thr Ile Arg
                 85                  90                  95

Gly Gly Asn Gly Phe Gly Ser Thr Gly Thr Gly Ser Glu Ala Met Ser
            100                 105                 110

Ser Gln Arg Thr Leu His Leu Trp Leu Lys Pro Asn Gly Thr Gly Ser
        115                 120                 125

Ser Ser
    130

<210> SEQ ID NO 5
<211> LENGTH: 107
<212> TYPE: PRT
<213> ORGANISM: Fowl adenovirus serotype 4, strain FAdV-4 ON1

<400> SEQUENCE: 5

Met Phe Leu Lys Ile Leu Val Leu Phe Cys Leu Ile Val Val Asp Cys
 1               5                  10                  15

Tyr Ile Phe His Thr Leu Gly Val His Trp Pro Thr Ala Met Leu Val
             20                  25                  30

Gly Thr Trp Met Leu Val Ala Glu Leu Leu Asn Ala Trp Asp Asp Phe
         35                  40                  45

Arg Gly Arg Pro Arg Leu Arg Phe Met Ser Met Pro Asp Phe Asp Ala
 50                  55                  60

Leu Ser Arg Ala Ala Asp Glu Leu Ala Ala Met Leu Asp Glu Asn Arg
 65                  70                  75                  80

Asn Ala Ala Pro Ile Gln Arg Gly Glu Glu Val Phe Glu Asp Ser
                 85                  90                  95

Asp Arg Asp Arg Asp Ser Gly Thr Asp Cys Asn
            100                 105

<210> SEQ ID NO 6
```

<211> LENGTH: 271
<212> TYPE: PRT
<213> ORGANISM: Fowl adenovirus serotype 4, strain FAdV-4 ON1

<400> SEQUENCE: 6

```
Met Ala Ser Asp Arg Tyr Trp Asp Leu Val Asn Ser Leu Ile Asn Arg
1               5                   10                  15

Gly Ile Val Thr Arg Glu Gln Trp Gln Ser Ala Asp Leu Ala Glu Tyr
            20                  25                  30

Arg Arg Tyr Ser Lys Gly Tyr Val Arg Gly Phe Ser Val Arg Lys Val
        35                  40                  45

Leu Arg Asp Val Ile Arg His Met Cys Trp Thr Lys Val Leu Gly Asp
    50                  55                  60

Tyr Leu Val Cys Pro Val Val Cys Gln Asp Asp Ile His Leu Asn Pro
65                  70                  75                  80

Phe Tyr Val Ile Leu Met Lys Asn Gly Tyr Asn Pro Arg Val Val Gly
                85                  90                  95

Thr Ile Leu His Lys Trp Ser Met Leu Thr Ser Asn Lys Asn Thr Val
            100                 105                 110

Trp Val Trp Gly Gly Ala Glu Thr Gly Gly Pro Tyr Leu Ala Glu Ala
        115                 120                 125

Ile Ala Tyr Thr Ser Pro Val Val Gly Cys Val Asp Trp Arg Asn Arg
    130                 135                 140

Ala Asn Pro Phe Ala Arg Asn Tyr Asn Cys Leu Val Tyr Trp Leu Asp
145                 150                 155                 160

Gly Gly Leu Phe Pro Glu Ser Ala Ile Gly Leu Cys Glu Gln Val Leu
                165                 170                 175

Arg Gly Glu Gly Thr Met Val Glu Glu Asp Thr Ser Gly Glu Arg
            180                 185                 190

Arg Trp Arg Glu Val Asn Arg Thr Pro Val Leu Ile Ser Thr Ser His
        195                 200                 205

Asp Val Thr Leu Thr Tyr Val Lys Tyr Gly Gln Thr Cys Lys Asp His
    210                 215                 220

Thr Asn Ser Leu Arg Ser Ala Met Tyr Val Ile Arg Leu Thr Glu Arg
225                 230                 235                 240

Met Glu Pro Gly Phe Val Ile Thr Cys Asn Asp Ala Arg Lys Phe Val
                245                 250                 255

Thr Trp Ala Ser Asn Asn Pro His Ile Asn Ala Glu Asp Met Leu
            260                 265                 270
```

<210> SEQ ID NO 7
<211> LENGTH: 178
<212> TYPE: PRT
<213> ORGANISM: Fowl adenovirus serotype 4, strain FAdV-4 ON1

<400> SEQUENCE: 7

```
Met Phe Pro Phe Cys Arg Arg Asp Tyr Val Ser Ala Asp Glu Leu Phe
1               5                   10                  15

Pro Lys Leu Glu Met Pro Pro Phe Lys Val Arg Leu Arg Leu Leu Asn
            20                  25                  30

Phe Tyr Pro Tyr Thr Ala Asp Glu Gly Thr Pro Ala Ile Arg Ser Glu
        35                  40                  45

Cys Ser Cys Arg Met Pro His Ser Leu Phe Cys Glu Ser Leu Gly Gln
    50                  55                  60

Leu Val Phe Thr Tyr Trp Phe Glu Thr Ile Gln Glu Phe Ile Glu Glu
65                  70                  75                  80
```

```
His Val Pro Ile Asp Pro Phe Pro His Cys Pro Ile Glu Asp Ile Ile
                85                  90                  95

Met Cys Arg Cys Ser Leu Arg Lys Glu Arg Asn Cys Asn Pro Leu Trp
            100                 105                 110

Gly Leu Gln Leu Leu Phe Cys Lys Arg Ser Ile Leu Gly Asn Leu Ser
        115                 120                 125

Ile Gly Leu Thr Pro Thr Gly Tyr Arg Ile Leu Ile Leu Pro Lys Tyr
    130                 135                 140

Phe Ser Pro Arg Val Lys Ala Ala Cys Glu Gln Ile Gln Arg Asn Leu
145                 150                 155                 160

Ser Gln Leu Lys Phe Thr Ile Lys Ile Glu Cys Phe Pro Phe Asp Lys
                165                 170                 175

Phe Glu

<210> SEQ ID NO 8
<211> LENGTH: 176
<212> TYPE: PRT
<213> ORGANISM: Fowl adenovirus serotype 4, strain FAdV-4 ON1

<400> SEQUENCE: 8

Met Pro Pro Ile His Ser Val Ser Phe Gln Val Leu Thr Ser Lys Glu
1               5                   10                  15

Phe Phe Ala Phe Phe Val Gly Lys Ser Gln Phe Phe Thr Pro Gly Thr
            20                  25                  30

Pro Asn Ser Phe Gln Glu Phe Val Phe Tyr Pro Arg Phe Lys Ser Phe
        35                  40                  45

Arg Val Glu Ile Arg Leu Arg Asp Ile Lys Ala Asp Glu Thr Lys Asn
    50                  55                  60

Cys Ala Thr Arg Trp Leu Leu Lys Tyr Arg Cys Thr Cys Pro Lys Pro
65                  70                  75                  80

His Ser Leu Phe Cys His Ser Leu Arg Met Lys Thr Tyr Ile Arg Trp
                85                  90                  95

Val Asp Glu Ile Arg Ala Thr Thr Arg Glu Ile Pro Leu Pro Val His
            100                 105                 110

Leu Gly Ile Leu Ala His Thr Tyr Leu Asp His Cys His Ala Cys Lys
        115                 120                 125

Asp Glu Thr Leu Leu Phe Ile Leu Ile Thr Ala Val Asn Pro Asn Asn
    130                 135                 140

Glu Pro Tyr Pro Glu Ile Ser Gln Asn Pro Phe Arg Val Ser Pro Lys
145                 150                 155                 160

Gly Gly Ala Asn Met His Pro Glu Asp Gln Glu Gly Arg Phe Ser Ile
                165                 170                 175

<210> SEQ ID NO 9
<211> LENGTH: 228
<212> TYPE: PRT
<213> ORGANISM: Fowl adenovirus serotype 4, strain FAdV-4 ON1

<400> SEQUENCE: 9

Met Ser Ile Ile Thr Asn Leu Leu Gln Thr Thr Arg Arg Pro Thr Ser
1               5                   10                  15

Ile Phe Arg Trp Thr Pro Glu Asp Asp Gln Val Arg His Ser Glu His
            20                  25                  30

Ser Phe Thr Ile Arg Thr Tyr Asp Leu Phe Asp Val Ile Asn Ile Gln
        35                  40                  45
```

```
Met Leu Phe Asp His Arg Phe Val Glu Phe Met Asn Gly Asp Ile Gln
    50                  55                  60

Phe Pro Phe Pro Gly Pro His Glu Tyr Ser Gln Thr Ser Leu Tyr Pro
65                  70                  75                  80

Arg Val Arg Pro Phe Arg Ala Asp Ile Ser Val Tyr Cys Ile Leu Arg
                85                  90                  95

Pro Ser Glu Asp Thr Glu Leu Gly Trp Ile Val Lys Leu Arg Cys Asn
            100                 105                 110

Cys Gly Asp Gly Asn Ser Leu Phe Cys Gln Ser Leu Arg Glu Leu Leu
            115                 120                 125

Phe His Ser Trp Lys Glu Ala Ile Gln Asn Gly Val Arg Ala Glu Pro
        130                 135                 140

Phe Pro Val Asp Leu Gly Pro Leu Thr Ser Asp Glu Leu Cys His Cys
145                 150                 155                 160

Ala Phe Cys Thr Gly Ala Thr Pro Leu Glu Leu Ile Ser Glu Ile Val
                165                 170                 175

Gln His Cys His Asn Asp Gly Val Ala Pro Leu Ser Ile Glu Asn Gly
            180                 185                 190

Glu Ile Ile Leu Arg Leu Ser Glu Ser Ala Ser Gln Ala Ile Ser Leu
        195                 200                 205

Pro Cys Phe Met His Tyr Met His Asn Ser Phe Pro Tyr Pro Thr Arg
    210                 215                 220

Ile His Thr Arg
225

<210> SEQ ID NO 10
<211> LENGTH: 209
<212> TYPE: PRT
<213> ORGANISM: Fowl adenovirus serotype 4, strain FAdV-4 ON1

<400> SEQUENCE: 10

Met Val Leu Leu Thr Gly Ser Arg Ala Ser Pro Pro His His Arg His
1               5                   10                  15

Asp Tyr Thr Ile Leu Cys Arg Pro Ala Leu Asp Ile Cys Asp Ala Ile
            20                  25                  30

His Phe Phe Asp Leu Arg Phe Leu Glu Phe Ile Asn Gly Arg Ala Leu
        35                  40                  45

Leu Pro Phe Pro Ser Ala Glu His Tyr Ser His Arg Glu Leu Asn Leu
    50                  55                  60

Cys Leu Pro Ala Phe Gln Ile Thr Ile Lys Leu Asp Leu Lys Arg Ser
65                  70                  75                  80

Ser Thr Tyr Trp Ile Leu Tyr Ser His Cys Arg Cys Lys Asp Pro Tyr
                85                  90                  95

Ser Leu Phe Cys Arg Ala Leu Asn Gln Tyr Val Ala Gln Gln Trp Arg
            100                 105                 110

Leu Asp Val Arg Glu His Leu Ala Ser Val Pro Ile Arg His Pro Ile
        115                 120                 125

Ser Ile Arg Ala Tyr Ala Lys Arg Thr Gly His Cys Ser His Cys
    130                 135                 140

Thr Phe His Thr Ile Tyr Glu Ile Leu Thr Glu Ile Val Lys Gln Thr
145                 150                 155                 160

Phe Gln Gly Arg Ser Ile Val Ile Phe Arg Arg Gln Glu Gly Arg Ile
                165                 170                 175

Arg Leu Gly Ile Pro Lys Phe Phe Arg Asp Tyr Val His Leu Ser Cys
            180                 185                 190
```

Phe Leu Lys Thr Leu Glu Ile Leu Pro His Ser Ile His Val Tyr Tyr
                195                 200                 205

Tyr

<210> SEQ ID NO 11
<211> LENGTH: 266
<212> TYPE: PRT
<213> ORGANISM: Fowl adenovirus serotype 4, strain FAdV-4 ON1

<400> SEQUENCE: 11

Met His Pro Leu Thr Val Leu Ile Glu Gln Leu Phe Glu Glu Gly Ile
1               5                   10                  15

Ala His Asp Leu Gln Trp Thr Phe Pro Thr Lys His Leu Leu Pro Ala
            20                  25                  30

His Glu Arg Glu Tyr Val Leu Ser Val Leu Arg Glu Arg Phe Gly Pro
        35                  40                  45

Ser Gln Ser Leu Phe Leu Gln Leu Pro Pro Glu Ala Ser Asp Pro Ile
    50                  55                  60

Ser Ser Ala Phe Tyr Asn Pro Arg Glu Asn Trp Phe Tyr Gln Leu Leu
65                  70                  75                  80

Glu Lys Glu Gly Tyr Asn Ala Arg Val Ala Ser Ala Thr Ile Gly Ala
                85                  90                  95

Trp Leu Lys Gly Glu Leu Asn Thr Leu Val Leu Cys Gly Asp Arg His
            100                 105                 110

Ser Asn Ala Lys Met Leu Phe Asn Val Ile Ser Ser Cys Phe Pro Met
        115                 120                 125

Ala Ile Thr Asp Ser Ala Ile Asn Ser Leu Asp Thr Leu Ala Glu Ile
    130                 135                 140

Ser Pro Ile Thr Pro Leu Tyr Cys Leu Pro Phe Val Gln Glu Arg Pro
145                 150                 155                 160

Asn Ala Ile Met Leu His Phe Met Glu Gly Asn Phe Leu Asn Thr Val
                165                 170                 175

Ile Lys Gly Lys Met Arg His Ile Pro His Thr Ser Val Leu Ile His
            180                 185                 190

Cys Ser Asp Leu Ser Ile Ala Asp Ser Phe Ser Ser Arg Asn Thr Ala
        195                 200                 205

Ile Leu Tyr Leu Val Gln Glu Asn Arg Ser Val Pro Ala Cys His Ser
    210                 215                 220

Pro Arg Lys Glu Leu Arg Asp Leu Val Leu Asn Ala Thr Gly Leu Pro
225                 230                 235                 240

Cys Leu Leu Ser Ile His Cys Lys Lys Asp His Glu Ile Cys Asp Asn
                245                 250                 255

Cys Ile Arg Ala Ser Pro Ser Asp Ala Leu
            260                 265

<210> SEQ ID NO 12
<211> LENGTH: 289
<212> TYPE: PRT
<213> ORGANISM: Fowl adenovirus serotype 4, strain FAdV-4 ON1

<400> SEQUENCE: 12

Met Ser Glu Leu Ala Phe His Leu Gln Leu Arg Ser Ile Phe Thr Pro
1               5                   10                  15

Ser Gln Trp Glu Glu Ile Asp Ala Glu Gln Tyr Lys Arg His Ala Asn
            20                  25                  30

```
Asn Ala Ala Glu Leu Leu Glu Ala Lys Arg Ile Tyr Cys Asn Tyr
            35                  40                  45
Gly Leu Tyr Gln Thr Leu Glu Leu Arg Ser Lys His Gly Arg Ser Pro
 50                  55                  60
Leu Ser Asn Ser Arg Gln Leu Ala Ser Ile Ala Ala Lys Glu Gly Met
 65                  70                  75                  80
His Leu Thr Ser Leu Val Asn Ala Ile Thr Ser Trp Leu Asp Ala Phe
                85                  90                  95
Pro Tyr Asn Pro Arg Lys Asp Tyr Val Asn Thr Met Tyr Val Val Gly
                100                 105                 110
Asp Ala Ser Ser Cys Ala Asp Pro Phe Ala Phe Ser Leu Val Arg Ala
                115                 120                 125
Phe Glu Cys Val Leu Met Gly Asp Ile Asn Gln Phe Asp Met Lys Glu
130                 135                 140
Tyr Ala Arg Val Gln Arg Glu Thr Lys Phe Leu Tyr Phe Pro Leu Ala
145                 150                 155                 160
Phe His Ser Leu Pro Phe Gln Ser Pro Thr Val Asn Asn Met Leu Gln
                165                 170                 175
Gly Arg Glu Thr Thr Ile Ala Ser Asp Gly Glu Leu Val Thr Ile Lys
                180                 185                 190
Pro Thr Lys Cys Leu Val Arg Leu Arg Ser Leu Pro His Pro Asp Arg
                195                 200                 205
Leu Pro Thr Asn Lys Asn Gln His Val Ile Ile Asn Phe Glu Ala Pro
                210                 215                 220
Thr Val Gly Leu Ala Phe Glu Ala Ala Glu Leu Val Gly Tyr Ile Arg
225                 230                 235                 240
Arg Leu Lys Thr His Ala Ala Thr Ser Asn Asp Val Leu Glu Cys Cys
                245                 250                 255
Asn Pro Tyr Gly Tyr Leu Cys Ser Lys Ser Ser Ala Gly Asp Met Cys
                260                 265                 270
Ser Thr Cys Ser Glu Tyr His Ala Asp Phe Leu Ser Leu Ser Asp Asp
                275                 280                 285
Tyr

<210> SEQ ID NO 13
<211> LENGTH: 394
<212> TYPE: PRT
<213> ORGANISM: Fowl adenovirus serotype 4, strain FAdV-4 ON1

<400> SEQUENCE: 13

Met Ser Ala Ile Pro Lys Lys Arg Lys Ala Trp Gln Tyr Arg Glu Glu
 1               5                   10                  15
Asp Tyr Leu Ser Gly Glu Gln Phe Tyr Asn Arg Val Thr Gly Trp Tyr
                20                  25                  30
Ala Gly Ala Thr Asp Leu Ala Pro Gln Leu Phe Lys Glu His Arg Phe
            35                  40                  45
Leu Pro Phe Asp Glu Phe Tyr Ser Leu Gly Gly Thr Asp Ala Lys Phe
 50                  55                  60
His Glu Leu Gln Gln Asn Val Glu Gln Glu His His Asp Arg Gln
 65                  70                  75                  80
Tyr Leu Arg Asn Gly Gln Leu Gln Ser Leu Asn Met Gly Arg Gln Pro
                85                  90                  95
Val Ile Gly Val Ile Tyr Gly Pro Thr Gly Ser Gly Lys Ser His Leu
                100                 105                 110
```

```
Leu Arg Ala Leu Ile Ser Cys Asn Met Leu Gln Pro Ile Pro Glu Thr
            115                 120                 125

Val Ile Phe Ile Thr Pro Glu Lys Asn Met Ile Pro Pro Ile Glu Gln
        130                 135                 140

Thr Ala Trp Asn Leu Gln Leu Leu Glu Ser Asn Tyr Asp Cys Arg Asp
145                 150                 155                 160

Asp Gly Thr Phe Ala Pro Arg Thr Cys Thr Phe Arg Pro Asp Phe Ile
                165                 170                 175

Glu Met Thr Tyr Glu Glu Ala Thr Pro Glu Asn Leu Asn Ile Glu
            180                 185                 190

Asn Pro Asn Asn Ile Tyr Val Thr Ala Ser Lys Lys Gly Pro Leu Ala
        195                 200                 205

Ile Val Met Asp Glu Cys Met Asp Lys Leu Cys Ser Gly Ser Ser Val
210                 215                 220

Ser Val Leu Phe His Ala Leu Pro Ser Lys Leu Phe Ala Arg Ser Ala
225                 230                 235                 240

Ala Cys Ser Ala Phe Tyr Ile Phe Val Val Leu His Asn Met Ala Pro
                245                 250                 255

Arg Thr Ala Ile Gly Asn Val Pro Thr Leu Lys Val Asn Ala Lys Ile
            260                 265                 270

His Ile Met Ser Cys His Ile Pro Gln Phe Gln Phe Ser Arg Phe Leu
        275                 280                 285

Tyr Ser Phe Ala His Asn Ile Ser Lys Asp Ile Met Val Leu Leu Lys
290                 295                 300

Ala Tyr Phe Ala Tyr Leu Gln Gln Asn Gln Lys Phe Ser Trp Ile Val
305                 310                 315                 320

Tyr Thr Pro Asp Pro Val Ser Asp Ser Phe Arg Trp Cys Thr Leu Asp
                325                 330                 335

Arg Asn Tyr Asp Ile Ile Pro Leu Asn Ile Asn Ile Gln Glu Asn Phe
            340                 345                 350

Leu Lys Ala Ala Lys Leu Ile Met Arg Phe Thr Asp Asn His Lys Pro
        355                 360                 365

His Trp Glu Lys Arg Arg Lys Leu Thr Val Leu Glu Thr Ile Ser Pro
370                 375                 380

Ser Asp Ser Pro Asp Glu Thr Lys Lys Ala
385                 390

<210> SEQ ID NO 14
<211> LENGTH: 1252
<212> TYPE: PRT
<213> ORGANISM: Fowl adenovirus serotype 4, strain FAdV-4 ON1

<400> SEQUENCE: 14

Met Glu His Val Ala Ala Gly Arg Leu Arg Arg Ser Ile Leu Gly Glu
1               5                   10                  15

His Ser His Leu Val Arg Thr Val Pro Arg Arg Gln Arg Asn Asp Pro
            20                  25                  30

Asp Ser Ala Pro Gly Arg Pro Pro Ser Thr Leu Phe Lys Thr Val Pro
        35                  40                  45

Gly Asp Val Leu Lys Asn Gly Ile Phe Tyr Ile Glu Gly Glu Pro Phe
    50                  55                  60

Lys Leu Gln Cys Val Pro Phe Ala Arg Gly Met Lys Lys Phe Leu Lys
65                  70                  75                  80

Leu His Lys Phe Leu Leu Thr Glu Arg Ser Arg Gln Tyr Asp Ile Ile
                85                  90                  95
```

```
Asp Tyr Gly Phe Tyr Glu Arg Asp Pro Thr Asn Ser Leu Arg Val Phe
            100                 105                 110

Arg Pro Lys Tyr Ile Gly Val Leu Lys Phe Leu Gly Arg Asn Ala Asp
            115                 120                 125

Ile Glu Arg Leu Phe Glu Asp Glu Ala Pro Leu Leu Pro Pro Ile Leu
        130                 135                 140

Leu Ala Arg Asp Ala Arg Arg Glu Pro Glu Arg Trp Leu Trp Val Leu
145                 150                 155                 160

Ser Arg Thr Ala Val Gln His Cys Pro Thr Cys Gly Arg His Trp Val
                165                 170                 175

Arg Asn His Ala Cys Asn Glu Arg Ser Ala Phe Tyr Tyr His Ala
            180                 185                 190

Val Gln Lys Thr Gly Ser Glu Met Trp Gln His Val His Phe Ser Cys
            195                 200                 205

Pro Ala Gln Ser Pro His Cys Lys Gln Leu Phe Leu Thr Tyr Asp Ile
        210                 215                 220

Glu Thr Tyr Thr Val Phe Glu Gln Lys Gly Lys Arg Met Gln Pro Phe
225                 230                 235                 240

Met Leu Cys Phe Met Leu Ser Gly Asp Pro Ala Leu Val Glu Val Ala
                245                 250                 255

Arg Lys Ile Ala Leu Glu Asp Thr Asp Val Arg Gln Leu Asp Glu Gly
            260                 265                 270

Phe Tyr Trp Ile Asp Pro Lys Pro Gly Glu Val Ala Arg Arg Phe Arg
        275                 280                 285

Thr Tyr Arg Thr Arg Leu Gln Gln His Phe Ala Glu His Leu Val Arg
            290                 295                 300

Arg Tyr Cys Arg Ala Asn Arg Glu Phe Cys Gly Glu Leu Met Ser Asp
305                 310                 315                 320

Gly Asn Tyr Thr Ser Ile Tyr His Ile Pro Tyr Glu Lys Phe Leu Gln
                325                 330                 335

Pro Ser Lys Pro Leu Thr Leu Pro Ser Asp Phe Tyr Ser Val Asp Val
            340                 345                 350

Ile Val Leu Gly His Asn Ile Thr Lys Phe Asp Glu Leu Leu Leu Ala
        355                 360                 365

Thr Glu Leu Val Glu Arg Arg Asp Leu Phe Pro Asp Ala Cys Arg Cys
370                 375                 380

Asp Arg Ser Phe Met Pro Arg Val Gly Arg Leu Leu Phe Asn Asp Ile
385                 390                 395                 400

Leu Phe His Met Pro Asn Pro Asn Phe Ser Lys Lys Asp Pro Thr Arg
                405                 410                 415

Leu His Arg Trp Val Lys Gly Val Val Asp Glu Arg Asp Met Arg Ser
            420                 425                 430

Val Phe Val Arg Phe Met Val Arg Asp Thr Leu Gln Leu Thr Ser Gly
        435                 440                 445

Ala Lys Leu Ala Lys Ala Ala Ser Ala Tyr Ala Leu Glu Leu Ser Lys
            450                 455                 460

Gly His Cys Pro Tyr Glu Ala Ile Asn Glu His Val Ser Arg Gly His
465                 470                 475                 480

Tyr Asp Arg Asp Ala Asp Gly Phe Pro Val Ala Arg Tyr Trp Glu Asp
                485                 490                 495

Ala Ser Val Leu Asp Glu Gln Lys Gln Leu Trp Asn Gln Asn His Pro
            500                 505                 510
```

-continued

Gly Gln Pro Tyr Asp Leu Val Arg Ala Cys Leu Glu Tyr Cys Met Gln
         515                 520                 525

Asp Val Arg Val Thr Gln Lys Leu Ala His Thr Leu Phe Glu Ser Tyr
530                 535                 540

Asp Arg Tyr Phe Lys Gln Glu Leu Gly Met His Gly Asn Tyr Asn Ile
545                 550                 555                 560

Phe Val Arg Pro Thr Ile Pro Ser Asn Thr His Ala Phe Trp Lys Gln
                565                 570                 575

Leu Thr Phe Ser Gln Tyr Val Gln Glu Gln Leu Asp Lys Arg Gln Ser
            580                 585                 590

Lys Pro Ala Lys Arg Asn Lys Lys Gly Asn Lys Thr Asn Lys Ser Ile
        595                 600                 605

Pro Thr Asp Tyr Val Ala Glu Val Tyr Ala Pro His Arg Pro Met Phe
    610                 615                 620

Lys Tyr Ile Arg Gln Ala Leu Arg Gly Gly Arg Cys Tyr Pro Ser Val
625                 630                 635                 640

Leu Gly Pro Phe Thr Gln Pro Val Tyr Val Phe Asp Ile Cys Gly Met
                645                 650                 655

Tyr Ala Ser Ala Leu Thr His Pro Met Pro His Gly Met Pro Leu Asp
            660                 665                 670

Pro Lys Phe Thr Ala Ala His Val Asp Glu Leu Asn Ala Ile Leu Leu
        675                 680                 685

Gln Pro Ala Pro Ile Ser Tyr Phe Asp Ala Arg Ile Lys Pro Ser Ile
    690                 695                 700

Leu Lys Ile Glu Ala Tyr Pro Pro Pro Glu Gln Leu Asp Thr Leu
705                 710                 715                 720

Pro Pro Leu Cys Asn Arg Arg Gly Gly Arg Leu Val Trp Ala Asn Glu
                725                 730                 735

Val Leu Tyr Asp Glu Val Val Thr Val Leu Asp Ile Ile Thr Leu His
            740                 745                 750

Asn Arg Gly Trp Lys Val Thr Ala Leu His Asp Asp Met Asn Ile Val
        755                 760                 765

Phe Pro Glu Trp Lys Thr Ile Cys Ala Asp Tyr Val Ser Lys Asn Ile
    770                 775                 780

Ala Ala Lys Glu Lys Ala Asp Gln Glu Lys Asn Glu Val Met Arg Ser
785                 790                 795                 800

Ile Ser Lys Met Leu Ser Asn Ala Leu Tyr Gly Ala Phe Ala Thr Asn
                805                 810                 815

Met Asp Thr Thr Arg Ile Val Phe Glu Gln Asp Leu Thr Asp Lys Asp
            820                 825                 830

Lys Lys Glu Ile Tyr Glu Gly Thr Gln Val Val Lys His Val Thr Leu
        835                 840                 845

Leu Asn Asp Arg Ser Phe Ser Gly Lys Thr Leu Tyr Glu Thr Gly Asp
    850                 855                 860

Pro Phe Ser Ala Pro Ser Leu Leu Ala His Phe Lys Pro Pro Glu Glu
865                 870                 875                 880

Ser Asp Asp Glu Glu Glu Glu Asp Ser Glu His Cys Glu Ser Thr Ser
                885                 890                 895

Lys Asp Glu Asn Val Val Leu Thr Ala Glu Glu Ala Asp Leu Ser
            900                 905                 910

Glu Val Asp Gln Glu Leu Glu Glu Ala Leu Thr Cys Gly Leu Tyr Ile
        915                 920                 925

Asp Asp Gly Arg Pro Pro Ala Glu Thr Asn Pro Ala His Ser Arg Ala 930                935               940

Asn Glu Thr Ala Phe Lys Pro Val Arg Phe Leu Asp Ala Pro Pro Glu
945                 950               955                 960

Ala Leu Thr Val Leu His Leu Glu Ser Leu Asp Lys Gln Val Glu Asn
                965                970                975

Lys Arg Tyr Ala Thr Gln Ile Ala Cys Phe Val Leu Gly Trp Ser Arg
                980                985                990

Ala Phe Phe Ser Glu Trp Cys Glu Ile Leu His Gly Pro Asp Arg Gly
            995                 1000               1005

Thr His Ile Leu His Arg Glu Leu Gln Thr Leu Tyr Gly Asp Thr
    1010                1015                1020

Asp Ser Leu Phe Leu Ser Glu Thr Gly Tyr Glu Arg Met Lys Thr
    1025                1030                1035

Arg Gly Ala His Arg Ile Lys Ser Lys Ser Thr Arg Leu Thr Phe
    1040                1045                1050

Asp Pro Glu Lys Pro Asp Leu Tyr Trp Ala Cys Asp Cys Asp Ile
    1055                1060                1065

Lys Cys Lys Gln Cys Gly Ser Asp Thr Tyr Ser Glu Ala Ile
    1070                1075                1080

Phe Leu Ala Pro Lys Leu Tyr Gly Leu Lys Asp Ala Val Cys Thr
    1085                1090                1095

Asn Pro Gln Cys Gly Tyr Val Gly Thr Gly Lys Ile Arg Ser Lys
    1100                1105                1110

Gly His Lys Gln Ala Glu Leu Ile Tyr Asp Thr Leu Leu Arg Cys
    1115                1120                1125

Trp Met Arg Tyr Glu Asp Gln Leu Phe Gly Ala Asp Ser Arg Ile
    1130                1135                1140

Pro Glu Leu His Thr Arg Arg Thr Ile Phe Lys Thr Thr Leu Leu
    1145                1150                1155

Asn Lys Val Ser Arg Tyr Glu Pro Phe Thr Ile His Asn Glu Gln
    1160                1165                1170

Leu Thr Arg Ile Leu Arg Pro Trp Lys Asp Pro Thr Gln Tyr Gln
    1175                1180                1185

Tyr Gly Asn Ala Leu Tyr Pro Tyr Asp Thr Glu His Pro Asn Pro
    1190                1195                1200

Arg Thr Val Glu Glu Val Arg His Val Ser Val Pro Gly Asp Glu
    1205                1210                1215

Glu Pro Leu Ala Pro Leu Arg Ile Asp Pro Tyr Ala Phe Leu Thr
    1220                1225                1230

Ala Glu Glu Cys Asp Glu Ile Leu Glu Leu Leu Gly Glu Thr Asp
    1235                1240                1245

Glu Arg Asp Pro
    1250

<210> SEQ ID NO 15
<211> LENGTH: 602
<212> TYPE: PRT
<213> ORGANISM: Fowl adenovirus serotype 4, strain FAdV-4 ON1

<400> SEQUENCE: 15

Met Val Arg Thr Gln Pro Ala Leu Val His Pro Arg Ser Val Phe Leu
1                5                  10                  15

Val Ser Arg Ile Tyr Asp Tyr Arg Leu Met Gln Leu Arg Asp Leu Thr
                20                  25                  30

```
Pro Gly Gly Ala Asn Val Ala Gln Asn Pro Tyr Asn Gly Leu Pro Pro
            35                  40                  45

Pro His Leu Leu Leu Gly Tyr Gln Tyr Met His Arg Thr Leu Asn Asn
 50                      55                  60

Tyr Phe Phe Asp Asn Arg Val Phe Met Gln Leu Gly Phe Glu Ser Pro
 65                  70                  75                  80

Pro Thr Gln Arg Pro Arg Arg Leu Phe Trp Thr Cys Leu Thr Asp Cys
                 85                  90                  95

Ser Tyr Ser Val Ser Val Gly Gln Tyr Met Arg Phe Leu Asp Leu Asp
            100                 105                 110

Asn Phe His Gly Thr Phe Thr Gln Met His Asn Ala Val Leu Met Asp
            115                 120                 125

Arg Ile Ala Ala Asp Met Gln Gly Ala Tyr Leu Arg Gly Arg Gly Val
            130                 135                 140

Val Val Gly Arg Asp Gly Arg Val Ile Pro Gln Pro Phe Asn Ala Asp
145                 150                 155                 160

Asp His Ser Tyr Leu Thr Gly Ser Gly Ala Ser Gly Leu Arg Asp Asp
                165                 170                 175

Val Val Leu Arg Thr Ala Ser His Arg Asp Ala Ala Ile Leu Ala Ala
            180                 185                 190

Ile Arg Tyr Leu Arg Val Ala Leu Cys His Tyr Leu Phe Cys Asn Ala
    195                 200                 205

Tyr Asp Leu Phe Thr Thr Glu Ser Thr Tyr Arg Phe Leu Pro Gly Ser
    210                 215                 220

Glu Val Phe Ala Glu Asp Asp Trp Leu Asn Leu Phe Val Glu Ala Phe
225                 230                 235                 240

Ser Glu Leu Asp Thr Gln Arg Leu Val Arg Ala Val Glu Asn Asp Pro
                245                 250                 255

Gln Ala Gly Trp Leu Gly Gln Asp Pro Ala Ser Ile Met Ala Arg Cys
                260                 265                 270

Leu Val Ser Thr Leu Ala Ser Asp Thr Ser Leu Ser Gly Gly Ala Ile
            275                 280                 285

Thr Leu Arg Asn Arg Arg Val Thr Asp Arg Ser Gly Leu Arg Pro Arg
            290                 295                 300

Asp Arg His Gly Arg Ala Ile Thr Ala Ser Gln Ile Arg Gln Ile Arg
305                 310                 315                 320

Arg Arg Ala Val Glu Arg Phe Val Asp Arg Leu Pro Arg Leu Thr Arg
                325                 330                 335

Arg Arg Arg Arg Pro Arg Pro Pro Ser Pro Gln Pro Pro Glu Glu Tyr
                340                 345                 350

Leu Pro Glu Leu Glu Pro Phe Pro Pro Glu Glu Glu Glu Glu Glu Glu
                355                 360                 365

Gln Leu Leu Asp Glu Val Val Arg Thr Ala Leu Glu Ala Ile Asp Ala
            370                 375                 380

Leu Gln Gln Glu Leu Ser Arg Thr Ala Gln Arg His Asp Leu Phe Gln
385                 390                 395                 400

Phe Ala Thr Ala Phe Tyr Arg Leu Leu Leu Gln Thr Gln Gln Ser Asp
                405                 410                 415

Val Ala Leu Val Thr Asp Ser Phe Leu Arg Lys Trp Val Leu Tyr Phe
            420                 425                 430

Phe Leu Ala Glu His Ile Ala Ser Thr Leu Tyr Tyr Leu Tyr Ser His
            435                 440                 445

Phe Ile Asn Tyr Arg Glu Phe Arg Arg Tyr Val Glu Ile Asp Thr Leu
```

```
            450                 455                 460
Gln Val Leu Ile Val Gly Trp Asp Val Asn Ala Gln Gln Val Phe Lys
465                 470                 475                 480

Arg Ile Trp Ser Glu Gln Ser Asn Ser Ser Arg Ile Phe Glu Thr Leu
                485                 490                 495

Trp Asn Arg Ile Leu Arg Asp Phe Leu Leu Met Val Glu Arg Thr Gly
                500                 505                 510

Gln Phe Glu Gly Met Asp Glu Thr Asp Gln Gln Leu Phe Leu Ser Asp
            515                 520                 525

Ile Gln Tyr Arg Asp Lys Ser Gly Asp Ile Asp Glu Val Leu Lys Gln
            530                 535                 540

Leu Asn Leu Ser Glu Glu Leu Ile Glu Ser Ile Asp Ile Ser Phe Arg
545                 550                 555                 560

Leu Lys Tyr Arg Gly Ile Val Ala Ile Ser Thr Asn Gly Arg Ile Thr
                565                 570                 575

Asp Asn Leu Arg Gln Val Leu Gln Asn Arg Arg Glu Glu Arg Asp Phe
                580                 585                 590

Gln Gln Arg Tyr His Pro Gln Gln Arg Arg
            595                 600

<210> SEQ ID NO 16
<211> LENGTH: 399
<212> TYPE: PRT
<213> ORGANISM: Fowl adenovirus serotype 4, strain FAdV-4 ON1

<400> SEQUENCE: 16

Met His Pro Val Leu Gln Asn Val Arg Asn Ala Ser Leu Gly Ser Gly
1               5                   10                  15

Gly Arg Ser Ser Gln Ser Gln Gln His Gln Gln Glu Leu Pro Pro
                20                  25                  30

Val Tyr Asp Gln Gln Arg Gln Ala Tyr Gln His Gln Gln Pro Tyr Gln
                35                  40                  45

Asp Arg Ser Ala Gly Gly Gly Gly Ala Arg Ala Pro Pro Asp Pro
            50                  55                  60

Pro Arg Tyr Pro Ala Gln His Ala Leu Pro Val Ala Thr Gly Pro Pro
65                  70                  75                  80

Glu Met Ala Ala Gly Gly Val Pro Glu Glu Pro Pro Ser Cys Gly Met
                85                  90                  95

Ala Val Gly Ala Thr Leu Asp Pro Thr Arg Met Tyr Glu Arg Asp Ala
                100                 105                 110

Ala Arg Lys Gly Ala Ile Pro Glu Val Asn Leu Phe Lys Ala Lys Pro
                115                 120                 125

Asp Thr Val Pro Gln Gly Asp Tyr Asp Arg Asp Met Met Tyr Arg Ser
            130                 135                 140

Gly Gln Val Val Gln Leu Asp Arg Asn Arg Val Leu Arg Pro Glu Asp
145                 150                 155                 160

Phe Ala Ala Asp Ala Gly Asp Pro Thr Phe Ser Pro Ala Val Asn His
                165                 170                 175

Met Lys Ala Ala Glu Leu Lys Arg Ala Ser Glu Gln Thr Ala Phe Gly
                180                 185                 190

Glu Glu Met Arg Asn Val Cys His Gln Thr Arg Ile Arg Thr Ala Leu
            195                 200                 205

Ser Arg Pro Glu Val Gly Ala Gly Ile Tyr Tyr Leu Tyr Asp Phe Val
            210                 215                 220
```

Gln Thr Tyr Met Glu His Pro Asp Gly Arg Val Lys Leu Asn Pro Gln
225                 230                 235                 240

Leu Val Leu Val Ala Gln His Ala Gly Asn Thr Ser Leu Ala Gln Arg
            245                 250                 255

Leu Trp Ala Ile Ala Glu Glu Lys Asn Ala Trp Leu Arg Asp Leu Ile
            260                 265                 270

Glu Met Ala Tyr Met Ile Val Thr Asp Pro Tyr Leu Ser Ile Glu Gln
            275                 280                 285

Gln Val Ser Ala Val Cys Thr Val Val Glu Leu Ser Met Lys Tyr
    290                 295                 300

Ala Lys Leu Ala Ala Lys Asn Gly Tyr Pro Ser Met Ala Gln Met Ala
305                 310                 315                 320

Lys Ala Gln Glu Phe Phe Tyr Arg Val Met Gln Ala Val Leu Asp Leu
            325                 330                 335

Gly Val Gln Leu Gly Val Tyr Asn Asn Arg Pro Val Thr Phe Arg Gln
            340                 345                 350

Lys Arg Met Ser Glu Ile Pro Gln Met Thr Asp Ala Glu Tyr Met Phe
            355                 360                 365

Gly Leu Thr Gln Ala Leu Glu Asn Arg Pro Pro Gln Gly Glu Phe Pro
370                 375                 380

Ala Asp Gly Glu Phe Ser Asp Ser Gly Glu Glu Asp Glu Phe Asp
385                 390                 395

<210> SEQ ID NO 17
<211> LENGTH: 590
<212> TYPE: PRT
<213> ORGANISM: Fowl adenovirus serotype 4, strain FAdV-4 ON1

<400> SEQUENCE: 17

Met Ser Ser Thr Glu Val Phe Gly Ala Leu Ala Pro Val Gly Arg Thr
1               5                   10                  15

Glu Val Ala Asp Ala Leu Ser Ser His Ala Asn Ser Lys Asp Ala Arg
            20                  25                  30

Ser Leu Arg Tyr Glu Pro Tyr Ala Asn Arg Leu Ile Lys Leu Gln Thr
        35                  40                  45

Ala Met Val Pro Pro Lys Val Asp Gly Thr Ser Glu Arg Val Ala Glu
    50                  55                  60

Val Val Lys Gly Leu Ala Glu Gln Gly Ala Ile Tyr Pro Asp Gln Met
65                  70                  75                  80

Gly Ala Ile His Ser Asp Leu Leu Asn Arg Val Tyr Thr Trp Asn Ser
                85                  90                  95

Met Gly Val Gln Glu Ser Ile Gln Ala Leu Val Asn Asp Val Ile His
            100                 105                 110

Gly Gln Asn Lys Val Leu Gln Asp Glu Leu Ala Arg Thr Arg Glu Ile
        115                 120                 125

Ala Asn Ala Ser Met Leu Thr Arg Phe Phe Asp Ser Leu Tyr Lys Thr
    130                 135                 140

Val Asp Arg Gly Gln Arg Asn Phe Glu Gly Phe Lys Lys Leu Leu Arg
145                 150                 155                 160

Leu Phe Val Asn Asn Val Pro Asn Ala Glu Val Tyr Ser Ser Gly Gly
                165                 170                 175

Ser Phe Ser Leu Gln Ile Asn Met Gly Gly Gln Ser Gln Asn Ile Asn
            180                 185                 190

Leu Thr Asn Ala Phe Asp Asn Leu Lys Asp Ile Trp Gly Ala Arg Trp
        195                 200                 205

Asp Ala Val Asn Asn Pro Arg Ile Gly Ala Leu Leu Thr Pro Asn Thr
    210                 215                 220

Arg Ala Leu Leu Phe Phe Val Ser Thr Phe Tyr Asp Tyr Gly Ser Met
225                 230                 235                 240

Glu Pro Gly Ser Tyr Leu Asp Asn Leu Met Arg Leu Tyr Lys Glu Ala
                245                 250                 255

Ile Arg Ala Asp Thr Asp Ala Glu Gly Asp Ala Ile Met Glu Leu Gly
            260                 265                 270

Asp Ala Gly Ala Asn Leu Asn Leu Lys Phe Asn Gln Tyr Lys Asp Thr
        275                 280                 285

Leu Asn Tyr Leu Leu Gln Asn Lys Pro Ser Val Pro Gln Thr Gly Pro
290                 295                 300

Leu Glu Met Ser Pro Glu Gln Glu Ser Leu Phe Lys Tyr Leu Met Arg
305                 310                 315                 320

Gln Leu Arg Arg Ala Leu Lys Asp Gly Val Asn Ser Asp Ile Ala Ile
                325                 330                 335

Ser Thr Met Ala Gln Tyr Val Asp Pro Arg Leu Tyr Thr Ser Asn Lys
            340                 345                 350

Val Phe Ile Asp Lys Leu Gln Asn Tyr Leu Leu Met Ala Ser Ala Arg
        355                 360                 365

Asn Pro Tyr Tyr Lys Thr Ile Val Leu Asp Pro His Trp Val Pro
370                 375                 380

Pro Ala Gly Leu Tyr Thr Asp Asn Phe Val Ile Pro Glu Met Met Pro
385                 390                 395                 400

Asn Phe Ser Asp Phe Ala Ser Glu Leu Glu Tyr Gly Gly Pro Ser Arg
                405                 410                 415

Asp Glu Tyr Phe Asp Asp Ser Pro Phe Arg Pro Pro Gln Lys Lys
            420                 425                 430

Phe Thr Glu Lys Glu Gln Ala Asp Tyr Asp Ser Leu Ile Asn Phe Phe
        435                 440                 445

Asp Ser Thr Leu Gly Val Gln Ser Glu Ala Gly Trp Ile Ala Asp His
450                 455                 460

Arg Leu Pro Gln Ala Phe Asp Gly Ala Leu Asn Val Ser Glu Arg Thr
465                 470                 475                 480

Pro Tyr Asn Thr Pro Leu Pro Asp Asp Ala Pro Met Arg Ser Arg Asn
                485                 490                 495

Ala Ser Val Ser Ser Ala Thr Asp Ala Leu Gly Gln Leu Lys Leu Ser
            500                 505                 510

Gly Thr Gly Gly Ala Gly Phe Phe Asp Ser Leu Lys Pro Ser Val Gly
        515                 520                 525

Thr Arg Arg Ser Thr Gly Leu Ala Lys Gly Leu Ala Gly Thr Gly Gln
530                 535                 540

Pro Pro Cys Pro Trp Pro Ala Ser Val Gly Tyr Ala Ser Ala Gly Tyr
545                 550                 555                 560

Gly Pro Ala Arg Gly Ile Arg Gly Ser Gly Leu Ala Arg Arg Ala Leu
                565                 570                 575

Ala Ala Arg Gly Leu Arg Gln Gly Lys Arg Leu Arg Phe Tyr
            580                 585                 590

<210> SEQ ID NO 18
<211> LENGTH: 525
<212> TYPE: PRT
<213> ORGANISM: Fowl adenovirus serotype 4, strain FAdV-4 ON1

<400> SEQUENCE: 18

```
Met Trp Gly Leu Gln Pro Pro Thr Ser Ile Pro Pro Pro Pro Pro
1               5                   10                  15

Thr Glu Leu Thr Pro Ser Thr Tyr Pro Ala Met Val Asn Gly Tyr Pro
                20                  25                  30

Pro Pro Ala Ala Ser Ala Gln Ser Cys Ser Ser Ser Gly Gly Gln Ser
            35                  40                  45

Glu Leu Tyr Met Pro Leu Gln Arg Val Met Ala Pro Thr Gly Gly Arg
    50                  55                  60

Asn Ser Ile Lys Tyr Arg Asp Tyr Thr Pro Cys Arg Asn Thr Thr Lys
65                  70                  75                  80

Leu Phe Tyr Val Asp Asn Lys Ala Ser Asp Ile Asp Thr Tyr Asn Lys
                85                  90                  95

Asp Ala Asn His Ser Asn Phe Arg Thr Thr Val Ile His Asn Gln Asp
            100                 105                 110

Leu Asp Ala Asp Thr Ala Ala Thr Glu Ser Ile Gln Leu Asp Asn Arg
    115                 120                 125

Ser Cys Trp Gly Gly Asp Leu Lys Thr Ala Val Arg Thr Asn Cys Pro
130                 135                 140

Asn Val Ser Ser Phe Phe Gln Ser Asn Ser Val Arg Val Arg Met Met
145                 150                 155                 160

Trp Lys Arg Asp Pro Pro Thr Ser Thr Ala Pro Pro Ser Ala Val Gly
                165                 170                 175

Ser Gly Tyr Ser Val Pro Gly Ala Gln Tyr Lys Trp Tyr Asp Leu Thr
            180                 185                 190

Val Pro Glu Gly Asn Tyr Ala Leu Cys Glu Leu Ile Asp Leu Leu Asn
    195                 200                 205

Glu Gly Ile Val Gln Leu Tyr Leu Ser Glu Gly Arg Gln Asn Asn Val
210                 215                 220

Gln Lys Ser Asp Ile Gly Val Lys Phe Asp Thr Arg Asn Phe Gly Leu
225                 230                 235                 240

Leu Arg Asp Pro Val Thr Gly Leu Val Thr Pro Gly Thr Tyr Val Tyr
                245                 250                 255

Lys Gly Tyr His Pro Asp Ile Val Leu Leu Pro Gly Cys Ala Ile Asp
            260                 265                 270

Phe Thr Tyr Ser Arg Leu Ser Leu Leu Gly Ile Gly Lys Arg Glu
    275                 280                 285

Pro Tyr Ser Lys Gly Phe Val Ile Thr Tyr Glu Asp Leu Gln Gly Gly
290                 295                 300

Asp Ile Pro Ala Leu Leu Asp Leu Asp Ser Val Asp Val Asn Asp Ala
305                 310                 315                 320

Asp Gly Glu Val Ile Glu Leu Asp Asn Ala Ala Pro Leu Leu His Asp
                325                 330                 335

Ser Ala Gly Val Ser Tyr Asn Val Ile Tyr Asp Gln Val Thr Gly Lys
            340                 345                 350

Pro Val Thr Ala Tyr Arg Ser Trp Met Leu Ala Tyr Asn Val Pro Asn
    355                 360                 365

Ser Gln Ala Asn Gln Thr Thr Leu Leu Thr Val Pro Asp Met Ala Gly
370                 375                 380

Gly Ile Gly Ala Met Tyr Thr Ser Leu Pro Asp Thr Phe Ile Ala Pro
385                 390                 395                 400

Thr Gly Phe Lys Glu Asp Asn Thr Asn Leu Cys Pro Val Val Gly
                405                 410                 415
```

```
Met Asn Leu Phe Pro Thr Tyr Asn Lys Ile Tyr Tyr Gln Ala Ala Ser
                420                 425                 430

Thr Tyr Val Gln Arg Leu Glu Asn Ser Cys Gln Ser Ala Thr Ala Ala
            435                 440                 445

Phe Asn Arg Phe Pro Glu Asn Glu Ile Leu Lys Gln Ala Pro Pro Met
        450                 455                 460

Asn Val Ser Ser Val Cys Asp Asn Gln Pro Ala Val Val Gln Gln Gly
465                 470                 475                 480

Val Leu Pro Val Lys Ser Ser Leu Pro Gly Leu Gln Arg Val Leu Ile
                485                 490                 495

Thr Asp Asp Gln Arg Arg Pro Ile Pro Tyr Val Tyr Lys Ser Ile Ala
                500                 505                 510

Thr Val Gln Pro Thr Val Leu Ser Ser Ala Thr Leu Gln
            515                 520                 525

<210> SEQ ID NO 19
<211> LENGTH: 77
<212> TYPE: PRT
<213> ORGANISM: Fowl adenovirus serotype 4, strain FAdV-4 ON1

<400> SEQUENCE: 19

Met Ser Ile Leu Ile Ser Pro Asn Asn Asn Thr Gly Trp Gly Met Arg
1               5                   10                  15

Arg Arg Ser Arg Ser Ser Ser Met Arg Gly Val Gly Met Arg Arg Arg
                20                  25                  30

Ala Arg Pro Leu Thr Leu Arg Ser Leu Leu Gly Leu Gly Thr Arg Arg
            35                  40                  45

Arg Arg Gly Ser Arg Arg Ser Arg Pro Arg Thr Thr Ser Arg Leu Val
        50                  55                  60

Val Val Arg Thr Arg Thr Ser Ser Met Arg Arg Arg Arg
65                  70                  75

<210> SEQ ID NO 20
<211> LENGTH: 179
<212> TYPE: PRT
<213> ORGANISM: Fowl adenovirus serotype 4, strain FAdV-4 ON1

<400> SEQUENCE: 20

Met Pro Ala Val Leu Leu Thr Gly Gly Arg Thr Ala Ser Lys Arg Lys
1               5                   10                  15

Phe Ser Thr Lys Gln Arg Arg Lys Lys Ala Val Ser Val Pro Lys Ile
                20                  25                  30

Arg Ser Arg Ser Gly Lys Arg Ser Gly Val Arg Lys Arg Ser Ser Ile
            35                  40                  45

Ser Val Pro Val Ser Gly Thr Ala Ser Ala Ser Glu Arg Ala Ala Leu
        50                  55                  60

Gln Asn Leu Ala Gln Arg Leu Gln Arg Gly Asn Tyr Thr Ala Trp Arg
65                  70                  75                  80

Ser Ala Asp Pro Ser Val Ala Ala Ser Glu Ala Ala Lys Ala Ala Ala
                85                  90                  95

Ala Ser Gly Ala Ala Ala Tyr Val Arg Asp Leu Thr Thr Gly Thr Ala
            100                 105                 110

Ala Glu Ala Val Pro Leu Thr Gly Thr Gly Arg Arg Arg Thr Gly
        115                 120                 125

Thr Arg Arg Ser Met Arg Gly Gly Phe Phe Pro Ala Leu Ile Pro Leu
    130                 135                 140
```

```
Ile Ala Ala Ala Ile Gly Ala Ile Pro Gly Ile Ala Gly Thr Ala Val
145                 150                 155                 160

Gly Ile Ala Ser Leu Lys Glu Gln Gln Arg Gln Phe Asn Lys Leu Tyr
                165                 170                 175

Gly Asn Lys

<210> SEQ ID NO 21
<211> LENGTH: 227
<212> TYPE: PRT
<213> ORGANISM: Fowl adenovirus serotype 4, strain FAdV-4 ON1

<400> SEQUENCE: 21

Met Asp Tyr Ala Ala Leu Ser Pro His Val Gly Ser Trp Ala Leu Arg
1               5                   10                  15

Glu His His Leu Gly Thr Ser Thr Leu Arg Gly Gly Ala Ile Asn Trp
                20                  25                  30

Ser Asn Val Gly Ser Arg Leu Ser Ser Ala Leu Ser Ser Thr Gly Arg
            35                  40                  45

Trp Leu Tyr Asn Thr Gly Asn Arg Phe Val His Ser Asn Ala Phe Asn
    50                  55                  60

Gln Ile Lys Gln Gly Leu Lys Asp Ser Gly Ile Val Arg Asn Val Ala
65                  70                  75                  80

Ser Leu Ala Gly Glu Thr Leu Gly Ala Leu Thr Asp Ile Gly Arg Leu
                85                  90                  95

Lys Leu Gln Gln Asp Leu Glu Lys Leu Arg Arg Lys Ala Leu Gly Glu
                100                 105                 110

Glu Gly Pro Ala Thr Gln Ala Glu Leu Gln Ser Leu Ile Gln Ala Leu
            115                 120                 125

Gln Ala Gln Leu Ala Ala Gly Ala Glu Val Ser Pro Gln Gly Ser Ala
130                 135                 140

His Val Pro Gln Thr Val Pro Ala Pro Pro Val Pro Thr Thr Arg Pro
145                 150                 155                 160

Ile Pro Glu Met Val Thr Glu Val Asn Pro Pro Ile Thr Ser Ser Ala
                165                 170                 175

Pro Ala Val Pro Val Val Asp Val Pro Thr Thr Leu Glu Met Pro Pro
            180                 185                 190

Pro Ala Lys Arg Arg Arg Lys Arg Ala Arg Ala Gly Ser Trp Arg Ala
        195                 200                 205

Arg Leu Asn Thr Leu Ser Gly Thr Gly Val Asn Val Ser Ser Arg Arg
210                 215                 220

Leu Cys Tyr
225

<210> SEQ ID NO 22
<211> LENGTH: 937
<212> TYPE: PRT
<213> ORGANISM: Fowl adenovirus serotype 4, strain FAdV-4 ON1

<400> SEQUENCE: 22

Met Ala Ala Leu Thr Pro Asp Leu Thr Thr Ala Thr Pro Arg Leu Gln
1               5                   10                  15

Tyr Phe His Ile Ala Gly Pro Gly Thr Arg Glu Tyr Leu Ser Glu Asp
                20                  25                  30

Leu Gln Gln Phe Ile Ser Ala Thr Gly Ser Tyr Phe Asp Leu Lys Asn
            35                  40                  45
```

-continued

```
Lys Phe Arg Gln Thr Val Val Ala Pro Thr Arg Asn Val Thr Thr Glu
 50              55                  60
Lys Ala Gln Arg Leu Gln Ile Arg Phe Tyr Pro Ile Gln Thr Asp Asp
 65              70                  75                  80
Thr Ser Thr Gly Tyr Arg Val Arg Tyr Asn Ile Asn Val Gly Asp Gly
                 85                  90                  95
Trp Val Leu Asp Met Gly Ser Thr Tyr Phe Asp Ile Lys Gly Ile Leu
                100                 105                 110
Asp Arg Gly Pro Ser Phe Lys Pro Tyr Cys Gly Thr Ala Tyr Asn Pro
            115                 120                 125
Leu Ala Pro Lys Glu Ser Met Phe Asn Asn Trp Ser Glu Thr Ala Pro
130                 135                 140
Gly Gln Asn Val Ser Ala Ser Gly Gln Leu Ser Asn Val Tyr Thr Asn
145                 150                 155                 160
Thr Ser Thr Thr Lys Asp Thr Thr Ala Ala Gln Val Thr Lys Ile Ser
                165                 170                 175
Gly Val Phe Pro Asn Pro Asn Gln Gly Pro Gly Ile Asn Pro Leu Arg
                180                 185                 190
Gln Val Glu Asn Ala Asn Thr Gly Val Leu Gly Arg Phe Ala Lys Ser
            195                 200                 205
Gln Tyr Asn Tyr Ala Tyr Gly Ala Tyr Val Lys Pro Val Ala Ala Asp
        210                 215                 220
Gly Ser Gln Ser Leu Thr Gln Thr Pro Tyr Trp Ile Met Asn Asn Ala
225                 230                 235                 240
Gly Thr Glu Tyr Leu Gly Ala Val Ala Val Glu Asp Tyr Thr Asn Ser
                245                 250                 255
Leu Ser Tyr Pro Asp Thr Met Ile Val Pro Pro Glu Asp Tyr Asp
                260                 265                 270
Asp Tyr Asn Ile Gly Thr Thr Arg Ala Leu Arg Pro Asn Tyr Ile Gly
            275                 280                 285
Phe Arg Asp Asn Phe Ile Asn Leu Leu Tyr His Asp Ser Gly Val Cys
        290                 295                 300
Ser Gly Thr Leu Asn Ser Glu Arg Ser Gly Met Asn Val Val Val Glu
305                 310                 315                 320
Leu Pro Asp Arg Asn Thr Glu Leu Ser Tyr Gln Tyr Met Leu Ala Asp
                325                 330                 335
Met Met Ser Arg His His Tyr Phe Ala Leu Trp Asn Gln Ala Val Asp
                340                 345                 350
Gln Tyr Asp Pro Glu Val Arg Val Phe Ser Asn Asp Gly Tyr Glu Glu
            355                 360                 365
Gly Ala Pro Ser Tyr Ala Phe Asn Pro Glu Ala Val Gly Ala Gly Glu
        370                 375                 380
Gly Tyr Gly Pro Asp Leu Ser Gln Ile Lys Leu Tyr Thr Asn Asn Thr
385                 390                 395                 400
Ala Ala Asn Asp Lys Asn Thr Ala Val Thr Asn Ala Thr Asn Phe
                405                 410                 415
Tyr Phe Gly Thr Val Pro Ser Tyr Glu Ile Asp Ile Ser Ala Thr Gln
                420                 425                 430
Arg Arg Asn Phe Ile Met Ala Asn Ile Ala Glu Tyr Leu Pro Asp Arg
            435                 440                 445
Tyr Lys Phe Ser Ile Ser Gly Phe Asp Ala Thr Ser Val Ala Pro Thr
        450                 455                 460
Thr Tyr Glu Tyr Met Asn Lys Arg Val Pro Leu Thr Asn Val Val Asp
```

```
              465                 470                 475                 480
        Met Phe Thr Asn Val Gly Ala Arg Trp Ser Ile Asp Gln Met Asp Asn
                            485                 490                 495

Val Asn Pro Phe Asn His His Arg Asn Trp Gly Leu Lys Tyr Arg Ser
                        500                 505                 510

Gln Leu Leu Gly Asn Ser Arg Tyr Val Asn Phe His Ile Gln Val Pro
                        515                 520                 525

Gln Lys Phe Phe Ala Ile Lys Asn Leu Leu Leu Ser Gly Ser Tyr
                    530                 535                 540

Thr Tyr Glu Trp Val Leu Arg Lys Asp Pro Asn Met Ile Leu Gln Ser
        545                 550                 555                 560

Ser Leu Gly Asn Asp Leu Arg Ala Asp Gly Ala Ser Ile Val Tyr Asn
                            565                 570                 575

Glu Val Asn Leu Met Ala Asn Phe Met Pro Met Asp His Asn Thr Ser
                        580                 585                 590

Asn Gln Leu Glu Leu Met Leu Arg Asn Ala Thr Asn Asp Gln Thr Phe
                        595                 600                 605

Val Asp Tyr Leu Gly Ala Lys Asn Ala Leu Tyr Ser Val Pro Ala Gly
                    610                 615                 620

Ser Thr Ala Leu Thr Ile Asn Ile Pro Ala Arg Thr Trp Glu Gly Met
        625                 630                 635                 640

Arg Gly Trp Ser Phe Thr Arg Ile Lys Ala Ala Glu Thr Pro Gln Leu
                            645                 650                 655

Gly Ala Gln Tyr Asp Val Asn Phe Lys Tyr Ser Gly Ser Ile Ala Tyr
                        660                 665                 670

Ser Asp Gly Gly Phe Tyr Leu Ser His Thr Phe Arg Asn Met Ser Ile
                    675                 680                 685

Leu Phe Asp Thr Ser Ile Asn Trp Pro Gly Asn Asp Arg Leu Leu Thr
                    690                 695                 700

Pro Asn Met Phe Glu Ile Lys Arg Ser Val Ala Leu Asp Thr Glu Gly
        705                 710                 715                 720

Phe Thr Met Ser Gln Cys Asp Ile Thr Lys Asp Trp Tyr Leu Ile Gln
                            725                 730                 735

Met Ala Thr Asn Tyr Asn Phe Val Tyr Asn Gly Tyr Arg Phe Trp Pro
                        740                 745                 750

Asp Arg Gln Tyr Phe His Tyr Asp Phe Leu Arg Asn Phe Asp Pro Met
                    755                 760                 765

Thr Arg Gln Gly Pro Asn Phe Ala Leu Pro Gly Leu Phe Asp Leu Val
        770                 775                 780

Ser Tyr Thr Pro Thr Thr Asp Asn Ser Gly Gln Gln Ala Ser Gln Glu
        785                 790                 795                 800

Ala Val Arg Asn Asn Ser Gly Phe Ile Ala Pro Arg Ser Trp Pro Val
                            805                 810                 815

Trp Ser Ala His Gln Gly Glu Ser Trp Pro Ala Asn Trp Pro Tyr Pro
                        820                 825                 830

Leu Cys Gly Gln Gln Ala Ile Gln Pro Gly Gln Val Leu Ser Tyr Lys
                    835                 840                 845

Lys Phe Leu Cys Asp Asn Tyr Leu Trp Thr Ile Pro Phe Ser Ser Asp
                    850                 855                 860

Phe Met Tyr Met Gly Glu Leu Thr Asp Leu Gly Gln Asn Pro Met Tyr
        865                 870                 875                 880

Thr Asn Asn Ser His Ser Met Val Ile Asn Phe Glu Leu Asp Pro Met
                            885                 890                 895
```

```
Asp Asp Pro Thr Tyr Val Tyr Met Leu Tyr Gly Val Phe Asp Thr Val
            900                 905                 910

Arg Val Asn Gln Pro Glu Arg Asn Val Leu Ala Met Ala Tyr Phe Arg
        915                 920                 925

Thr Pro Phe Ala Thr Gly Asn Ala Val
        930                 935

<210> SEQ ID NO 23
<211> LENGTH: 209
<212> TYPE: PRT
<213> ORGANISM: Fowl adenovirus serotype 4, strain FAdV-4 ON1

<400> SEQUENCE: 23

Met Thr Gly Thr Thr Glu Ser Gln Leu Arg Asp Leu Val Ala Ala Met
1               5                   10                  15

His Pro Arg His Arg Phe Leu Gly Val Phe Asp Arg Thr Phe Pro Gly
            20                  25                  30

Phe Leu Asp Pro Glu Arg Pro Ala Ser Ala Ile Val Asn Thr Gly Ser
        35                  40                  45

Arg Ser Ser Gly Gly Met His Trp Ile Gly Phe Ala Tyr Asp Pro Gln
    50                  55                  60

Tyr Arg Arg Cys Tyr Met Phe Asp Pro Phe Gly Trp Ser Asp Lys Lys
65                  70                  75                  80

Leu Leu Glu Leu Tyr Lys Val Lys Tyr Asp Ala Met Leu Lys Ala Thr
                85                  90                  95

Gly Leu Ser Gln Gln Asp Arg Cys Ile Glu Leu Val Arg Ser Val Gln
            100                 105                 110

Ala Val Gln Cys Pro Cys Ser Gly Ala Cys Gly Leu Phe Ser Ala Leu
        115                 120                 125

Phe Ile Ala Ser Phe Asp Arg Tyr Arg Arg Ser Pro Met Asn Gly Asn
    130                 135                 140

Pro Ile Ile Asp Thr Val Val Gly Val Asn His Glu Asn Met Tyr Lys
145                 150                 155                 160

Pro Ala Phe Arg Glu Ile Leu His Arg Asn Gln Glu Arg Met Asn Ala
                165                 170                 175

Trp Phe Ala Arg Asn Asn Pro Tyr Phe Gln Arg His Ala Glu Leu Leu
            180                 185                 190

Lys Arg Glu Thr Ala Ile Asn Thr Leu Pro Gln Asn His Val Gln Gln
        195                 200                 205

Ala

<210> SEQ ID NO 24
<211> LENGTH: 493
<212> TYPE: PRT
<213> ORGANISM: Fowl adenovirus serotype 4, strain FAdV-4 ON1

<400> SEQUENCE: 24

Met Gly Gly Ala Asn Gly Phe Gly Arg Val Arg Phe Pro Ile Gly Arg
1               5                   10                  15

Lys Thr Asp Leu Lys Arg Ser Ile Ala Asn Asp Pro Gly Phe Ser Ser
            20                  25                  30

Ser Glu Asp Asp Ala Val Glu Arg Pro Ser Thr Ser His Arg Ser Arg
        35                  40                  45

Ser Arg Ser Leu Glu Met Pro Gly Glu Lys Arg Lys His Gln Ala Ala
    50                  55                  60
```

```
Cys Leu Asn Asp Ser Asp Ser Glu Leu Glu Leu Met Ala Glu Leu Lys
 65                  70                  75                  80

Pro Pro Ala Lys Pro Gln Arg Gly Lys Arg Pro Pro Lys Lys Lys
             85                  90                  95

Thr Thr Ser Thr Ala Glu Leu Ala Asp Ser Asp Val Leu Glu Ala Glu
            100                 105                 110

Gln Glu Leu Lys Ser Asp Thr Glu Glu Phe Gln Ser Thr Gly Gly Pro
            115                 120                 125

Met Ala Gly Ala Leu Ala Glu Asp Pro Val Thr Phe Ser Ala Gln Lys
            130                 135                 140

Ala Met Ala Tyr Leu Thr Thr Val Cys Glu Ser Leu Asp Met Arg Trp
145                 150                 155                 160

Gln Gly Gly Thr Ile Glu Pro Leu Asp Ala Ile Trp Thr Lys Val Ala
                165                 170                 175

Gly Leu Phe Met Arg Arg His Pro Glu Phe Arg Leu Thr Phe Ser
            180                 185                 190

Ser Phe Asp Ser Phe Tyr Gly Gln Leu Gly Arg Phe Leu Ala Ala Met
            195                 200                 205

Ile Tyr Asn Leu Ala Gly Leu Glu Pro Lys Phe Val Pro Gly Gly Ala
210                 215                 220

His Val Trp Arg His Gly Trp Lys Gly Ala Thr Met Pro Lys Cys Phe
225                 230                 235                 240

His Gly Ile Pro Met Ser Leu Lys Pro Arg Thr Val Glu Leu Asn Pro
                245                 250                 255

Thr Ser Glu Ala Gly Lys Arg Ala Ile Ala Glu Gln Gly Gly Arg Val
            260                 265                 270

Glu Lys Asn Arg Phe Gly Arg Gln Val Val Val Leu Arg Phe Asp Asn
            275                 280                 285

Asn Ala Val Cys Ala Lys Asp Lys Glu His Asn Gly Phe Pro Tyr Pro
            290                 295                 300

His Ala Thr Gly Ser Cys Ala Met Val Phe Ser Asp Ala Gln Lys Ala
305                 310                 315                 320

Leu Ser Ala Met Lys His Asp Leu Ser Trp Thr Met Ala Leu Tyr Pro
                325                 330                 335

Asn Ala Asp Arg Ser Arg Ile Glu Gln Cys Val Leu Ile Ser Thr Asn
            340                 345                 350

Cys Asn Cys Asn Tyr Gly Cys Glu Ala Pro Ile Ser Gly Arg Gln Ile
            355                 360                 365

Cys Arg Met Thr Pro Tyr Lys Leu Ser Gly Thr Asp Ile Thr Lys
            370                 375                 380

Asp Met Leu Glu Ser Arg Ala Asp Met Lys Ala His His Lys His Pro
385                 390                 395                 400

His Thr Met Val Tyr Thr Cys Cys Asn Pro Gln Ala Pro Gly Gly Ser
                405                 410                 415

Asn Pro Ala Gly Ser Ser Arg Ala Gln Arg Thr Glu Lys Ser Cys
            420                 425                 430

Ser Trp Arg Ile Ser Tyr Met Asp Leu Arg Tyr Ala Tyr Val Phe Ala
            435                 440                 445

Asn Glu Leu Ile Thr Thr Ala Leu Gly Thr Glu Ala Thr Gln Val
            450                 455                 460

Arg Glu Phe Arg Trp Asn Asp Lys Tyr Ala Tyr Lys Thr Glu Val Ile
465                 470                 475                 480

Ala Pro Val Cys Pro Val Ser His Ser Asp Pro Phe Ala
```

```
                    485                 490

<210> SEQ ID NO 25
<211> LENGTH: 100
<212> TYPE: PRT
<213> ORGANISM: Fowl adenovirus serotype 4, strain FAdV-4 ON1

<400> SEQUENCE: 25

Met Glu Val Glu Ile Asp Ser Ser Arg Ser Glu His Ser Asp Tyr Glu
1               5                   10                  15

Asp Pro Met Pro Ser Asp Ala Glu Glu Gln Arg Glu Arg Ser Ala Arg
            20                  25                  30

Leu Ser Thr Ser Arg Ser Tyr Gly Ser Pro Thr Lys Arg Lys Lys Lys
        35                  40                  45

Leu Gln Arg Asp Ala Ala Tyr Arg Glu Pro Leu Thr Lys Thr Phe Ser
    50                  55                  60

Ser Glu Asp Glu Arg Glu Ala Glu Ser Asp Val Arg Thr Tyr Arg Ser
65                  70                  75                  80

Pro Gln Lys Arg Lys Met Ser Thr Ile Arg Gly Pro Arg Gly Arg Arg
                85                  90                  95

Arg Leu Ser Ala
            100

<210> SEQ ID NO 26
<211> LENGTH: 91
<212> TYPE: PRT
<213> ORGANISM: Fowl adenovirus serotype 4, strain FAdV-4 ON1

<400> SEQUENCE: 26

Met Met Ser Asn Pro Ser Gly Tyr Gly Gln Leu Lys Ser Leu Ala Thr
1               5                   10                  15

Val Gly Leu Val Leu Arg Ser Ala Leu Glu Arg Phe Pro Trp Thr Asp
            20                  25                  30

Tyr Val Ser His Leu Arg Asp His Val Ser Thr Thr Tyr Arg Lys Glu
        35                  40                  45

Leu Pro Ser Ser Ala Glu Leu Val Glu Ile Glu Leu Asp Thr Leu Ala
    50                  55                  60

Glu Ile Leu Ile Asp Arg Leu Gly Gln Glu Thr Ala Val Leu Ser Ala
65                  70                  75                  80

Tyr Lys Ser Leu Gly Arg Pro Tyr Arg Thr Arg
                85                  90

<210> SEQ ID NO 27
<211> LENGTH: 94
<212> TYPE: PRT
<213> ORGANISM: Fowl adenovirus serotype 4, strain FAdV-4 ON1

<400> SEQUENCE: 27

Met Leu Val Phe Arg Cys Gly Glu Leu Ala Val Gly Ala Gly Gly Val
1               5                   10                  15

Ala Gly Leu Ala Phe Ser Tyr Gly Leu Leu Ala Thr Gly Phe Ile Pro
            20                  25                  30

Val Gly Gly Ala Phe His Leu Ala His Val Phe Ser Asp Val Ser Leu
        35                  40                  45

Gly Ala Phe Val Leu Leu Gly Asn Asn Gly Gly Lys Val Arg Arg Glu
    50                  55                  60

Phe Arg Tyr Phe Pro Thr Arg Arg Leu Arg Phe Leu Phe Trp Arg Phe
65                  70                  75                  80
```

```
Leu Ile Ala Phe Asp Lys Val Phe Gln Asp Phe Cys Arg Arg
                85                  90

<210> SEQ ID NO 28
<211> LENGTH: 920
<212> TYPE: PRT
<213> ORGANISM: Fowl adenovirus serotype 4, strain FAdV-4 ON1

<400> SEQUENCE: 28

Met Glu Ser Thr Ala Asp Gly Asp Lys Ala Arg Gly Glu Pro Val
1               5                   10                  15

Ala Glu Arg Glu Ala Ser Asp Thr Ala Gly Ala Asp Gly Phe Pro
            20                  25                  30

Ala Pro Glu Asp Glu His Pro Asp Asp Gly Glu Pro Asp Glu Pro Ala
            35                  40                  45

Asp Arg Asp Asp Arg Ser Gly Glu Ser Asp Ala Asp Ser Gly Tyr Tyr
        50                  55                  60

Ser Ala Asp Gly Gly Arg Asp Ala Glu Cys Asp Gly Glu Gly Ala Arg
65                  70                  75                  80

Pro Asp Thr Pro Thr Asp Glu Ser Ser Ala Pro Thr Thr Pro Ser Thr
                85                  90                  95

Ala Val Arg Arg Ser Ser Gly Glu Ser Ser Pro Asp Arg Gly Gly Cys
            100                 105                 110

Phe Ser His Ser Ser Asp Ser Glu Leu Gly Cys Ala Thr Glu Thr Arg
            115                 120                 125

Asp Pro Phe Ala Ala Gly Leu Arg Lys Cys Ile Glu Arg Gln Ala Met
    130                 135                 140

Ile Leu Thr Gly Ala Leu Lys Asp Ala Gln Leu Asp Pro Pro Leu Asp
145                 150                 155                 160

Ser Met Pro Leu Thr Val Asp Ala Val Gln Arg Gln Leu Glu Arg Phe
                165                 170                 175

Leu Phe Asn Pro Asp Pro Lys Val Pro Arg Glu His Val Glu Ala Arg
            180                 185                 190

Tyr Asn Phe Tyr Pro Pro Phe Met Thr Pro Lys Ala Ile Ala Asn Tyr
            195                 200                 205

His Ile Phe Ala Val Thr Ala Pro Ile Pro Pro Ser Cys Lys Ala Asn
    210                 215                 220

Arg Ser Gly Ser Glu Val Leu Arg Ala Ala Glu Asn Ala Arg Phe Phe
225                 230                 235                 240

Lys Arg Leu Pro Arg Trp Lys Gln Gly Val Thr Val Asp Asp Gly Leu
                245                 250                 255

Gly Asp Glu Val Ser Pro Ile Thr Glu Leu Lys Asp Ala Lys Leu Val
            260                 265                 270

Pro Leu Arg Asp Asp Thr Ser Arg Leu Glu Trp Ala Lys Met Arg Gly
            275                 280                 285

Glu His Val Arg Tyr Phe Cys Tyr Pro Ser Leu His Met Pro Pro Lys
    290                 295                 300

Ile Ser Arg Met Leu Met Glu Val Leu Leu Gln Pro Phe Ala Gln Glu
305                 310                 315                 320

Val Ala Ser Gly Pro Glu Gln Glu Asp Pro Glu Pro Val Val Ser Asp
                325                 330                 335

Ala Glu Leu Ala Cys Ile Val Asp Pro Glu Gly Val Met Gln Pro His
            340                 345                 350

Ala Leu Ala Arg Ala Ile Glu Val Arg Arg Arg Met Val Ala Gln Ala
```

```
                355                 360                 365
Val Arg Tyr Thr Ala Gln Leu Glu Leu Met Glu Arg Val Phe Arg Glu
370                 375                 380
Pro Ser Ser Ile Lys Lys Ala Gln Glu Val Leu His His Thr Phe His
385                 390                 395                 400
His Gly Phe Val Ala Leu Ile Arg Glu Thr Ala Lys Val Asn Leu Ser
                405                 410                 415
Asn Tyr Ala Thr Phe His Gly Ile Thr Tyr Asn Asp Pro Leu Asn Asn
                420                 425                 430
Cys Met Leu Ala Lys Leu Met Glu Gly Ser Asp Lys Arg Asp Tyr Val
                435                 440                 445
Val Asp Ser Ile Tyr Leu Phe Leu Val Leu Thr Trp Gln Thr Ala Met
450                 455                 460
Gly Met Trp Gln Gln Ala Ile Gln Glu Glu Thr Ile Glu Ala Tyr Arg
465                 470                 475                 480
Glu Ala Phe Thr Arg Leu Arg Arg Ala Ile Tyr Ala Leu Glu Thr Pro
                485                 490                 495
Thr Glu Ile Ser Lys Ala Ile Val Asp Val Leu Met Asp Gly Asp Arg
                500                 505                 510
Leu Cys Ala Glu Met Arg Lys Ala Leu Pro Asn Phe Thr Asn Gly Ser
                515                 520                 525
Gln Ile Ser Ala Phe Arg Gln Phe Ile Met Glu Arg Ser Asn Ile Pro
                530                 535                 540
Thr Thr Ala Ala Pro Phe Leu Pro Ser Asp Phe Val Pro Leu Ser Phe
545                 550                 555                 560
Arg Gln Ala Gln Pro Leu Leu Trp Asp Gln Val Tyr Leu Leu Gln Thr
                565                 570                 575
Ala Phe Phe Leu Cys Asn His Gly Gly Tyr Leu Trp Glu Pro Glu Glu
                580                 585                 590
Thr Glu Asn Pro Asn Pro Arg Asp Arg Thr Tyr Cys Pro Cys Asn Leu
                595                 600                 605
Cys Ser Pro His Arg Met Pro Gln His Asn Val Pro Leu His Asn Glu
                610                 615                 620
Leu Leu Ala Ile Asn Thr Phe Glu Ile Arg Thr Asp Asp Gly Lys Thr
625                 630                 635                 640
Phe Lys Leu Thr Pro Glu Leu Trp Ala Asn Ala Tyr Leu Asp Lys Phe
                645                 650                 655
Glu Pro Lys Asp Tyr His Pro Phe Glu Val Val His Phe Pro Gln His
                660                 665                 670
Glu Glu Ala Phe Ser Arg Asp Leu Thr Ala Cys Val Thr Lys Ser Pro
                675                 680                 685
Glu Ile Leu Ser Leu Ile Arg Gln Ile Gln Ala Ser Arg Glu Glu Phe
                690                 695                 700
Leu Leu Thr Arg Gly Lys Gly Val Tyr Lys Asp Pro Asp Thr Gly Glu
705                 710                 715                 720
Val Leu Thr Pro Gln Pro Asp Leu Gln Ala Gly Ala Ala Arg Arg Gln
                725                 730                 735
Ala Leu Pro Thr Ala Tyr Ala Asp His Ala Arg Gly Ala Ala Thr Ser
                740                 745                 750
Ala Glu Pro Ser Arg Ala Leu Arg Pro Thr Ser Val Ala Thr Ala Ala
                755                 760                 765
Gly Glu Thr Glu His Gly Gly Ala Leu Gln Arg Ala Ile Gly Ser Val
                770                 775                 780
```

```
Gln Pro Ser Val Ala Gly Ala Thr Pro His Gly Pro Glu Asn Gly Arg
785                 790                 795                 800

Pro Glu Gly Gln Gly Phe Gly Thr Ser Gly Ala Arg Asn Leu Gln Ser
            805                 810                 815

Arg Gly Gly Asp Arg Val Arg Arg Asn Ser Arg Gln Arg Gly Tyr
        820                 825                 830

Arg Tyr Gly Arg Gly Pro Asp Glu His Asp Leu Arg Arg Gly Gly Gly
            835                 840                 845

Gly Arg Arg Gly Val Phe Arg Gly Ser Gly Trp Gly Arg Gln Gly Glu
        850                 855                 860

Gln Pro Pro Ser Pro Tyr Asp Ser Pro Gln Thr Gln Pro Lys Ser Ile
865                 870                 875                 880

Leu Arg Arg Pro Val Pro Gly Pro Asp Glu Thr Ser Pro Ala Tyr Gln
                885                 890                 895

Gln His Arg Gln His Asp Arg His Arg Gln Glu Asp Pro Ser Ala Ala
                900                 905                 910

Pro Thr Arg Pro Ser Thr Pro Arg
        915                 920

<210> SEQ ID NO 29
<211> LENGTH: 195
<212> TYPE: PRT
<213> ORGANISM: Fowl adenovirus serotype 4, strain FAdV-4 ON1

<400> SEQUENCE: 29

Met Ala Gln Arg Met Val Asp Leu Lys Ala Arg Ala Ser Glu Pro Pro
1               5                   10                  15

Glu Pro Glu Ile Tyr Asn Pro Glu Ala Thr Glu Ser Asp Gly Glu
            20                  25                  30

Thr Leu Gly Ser Glu Asp Thr Asp Thr Glu Glu Asp Gln Met Ser Thr
        35                  40                  45

Ile Ser Glu Glu Glu Glu Glu Asp Glu Ala Tyr Ser Ala Asp Leu
    50                  55                  60

Ala Gly Glu Asp Lys Glu Asn Ser Pro Pro Pro Thr Ile Pro Pro
65              70                  75                  80

Lys Arg Ser Arg Lys Ala Ser Ser Val Ala Pro Ser Gln Ala Leu Thr
                85                  90                  95

Arg Pro Pro Leu Arg Thr Asn Asn Thr Ala Asn Thr Thr Gly Thr Ala
            100                 105                 110

Arg Arg Ile Arg Pro Gln Arg Leu Pro Asp Arg Ala Pro Arg Gly Asn
        115                 120                 125

Tyr Arg Ser Trp Ala Arg Tyr Arg Val Ala Ile Cys Gln Ala Leu Arg
    130                 135                 140

Asp Thr Val Phe Asp Arg Val Gln Ala Ala Gln Val Leu Lys Asn Thr
145                 150                 155                 160

Arg Gln Leu Tyr Val Pro Ala Ser Val Leu Ala Tyr Tyr Ala Arg Lys
                165                 170                 175

Leu Leu Ala Met Thr Asp Asp Ser Ala Phe Thr His Ser Cys Glu Gly
            180                 185                 190

Ser Gln Arg
        195

<210> SEQ ID NO 30
<211> LENGTH: 247
<212> TYPE: PRT
```

<213> ORGANISM: Fowl adenovirus serotype 4, strain FAdV-4 ON1

<400> SEQUENCE: 30

| Met | Asn | Leu | Leu | Asn | Ala | Ala | Pro | Thr | Pro | Tyr | Val | Trp | Lys | Tyr | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Pro Val Thr Gly Lys Cys Ala Gly Ala Gln Gln Asn Tyr Gly Ala Thr
              20                  25                  30

Ile Asp Trp Val Leu Pro Gly Gly Asn Ser Phe Ala Tyr Ala Ala Asp
            35                  40                  45

Glu Ile Arg Arg Arg Phe Pro Glu Pro Ala Val Thr Arg Ala Ile Thr
        50                  55                  60

Ala Arg Phe Glu Ala Glu Ser Asp Gln Gln Pro Tyr Ala Gly Pro His
65                  70                  75                  80

Glu Thr Asn Ile Ile Thr Ala Asp Val Val Arg Ser Gly Ala Pro Pro
                85                  90                  95

Ser Ala Val Tyr Pro Phe Asp Pro Ser Gly Val Gln Arg Val Gln Leu
            100                 105                 110

Ser Gly Gly Met Met Gly Gly Arg Thr Glu Gly Arg Val Gln Leu Ser
        115                 120                 125

Gly Gly Leu Thr Glu Gly Arg Met Gln Leu Ala Gly Gly Ala Ala Gly
130                 135                 140

Lys Leu Pro Thr Arg Ala Arg Pro Thr Leu Arg Pro Pro Arg Trp Cys
145                 150                 155                 160

Gly Thr Thr Leu Thr Gly Asn Gly Leu Pro Ala Asp Tyr Pro Glu Met
                165                 170                 175

Thr Pro Asp Ala Phe Lys Tyr Tyr Leu Arg Val Gln Gly Pro Ser Gln
            180                 185                 190

Glu Val Asp Glu Pro Gly Val Met Ser Gln Arg Arg Phe Met Thr Thr
        195                 200                 205

Phe Leu Pro Ala Met Val Pro His Pro Phe Asp Ser Glu Ser Pro Asp
210                 215                 220

Ala Phe Pro Ala Tyr Phe Ser Ser Val Tyr Lys Gly Thr Asn Ala Phe
225                 230                 235                 240

Glu Pro Val Phe Trp Gln Gly
                245

<210> SEQ ID NO 31
<211> LENGTH: 78
<212> TYPE: PRT
<213> ORGANISM: Fowl adenovirus serotype 4, strain FAdV-4 ON1

<400> SEQUENCE: 31

Met Ala Glu Pro Arg Arg Tyr Trp Leu Lys Ile Asn Asp Gln Ala Met
1               5                   10                  15

Leu Arg Phe Asp Glu Pro Leu Asn Pro Gly Phe Val Phe Trp Leu Arg
            20                  25                  30

Arg Lys Phe Arg Ala Arg Val His Ser Glu Gly Gly Glu Arg Val Val
        35                  40                  45

Met Thr Arg Lys Glu Pro Phe Ser Ala Ser Glu Met Gln Glu Leu Tyr
    50                  55                  60

Ser Glu Thr Asp Tyr Arg Gln Gln Arg Val Ser Thr Ala Pro
65                  70                  75

<210> SEQ ID NO 32
<211> LENGTH: 432
<212> TYPE: PRT

<213> ORGANISM: Fowl adenovirus serotype 4, strain FAdV-4 ON1

<400> SEQUENCE: 32

```
Met Ser Ala Leu Ile Ala Ser Ala Ala Asp Thr Val Ser Val Ser Gly
1               5                   10                  15

Lys Lys Arg Pro Arg Arg Ala Leu Ser Glu Pro Ile Arg Tyr Leu Ser
            20                  25                  30

Glu Gly Asp Glu Arg Arg Lys Pro Lys Arg Ala Pro Pro Ala Thr Arg
        35                  40                  45

Ala Asn Gly Pro Leu Leu Asp Leu Val Tyr Pro Phe Asp Phe Asn Ala
    50                  55                  60

Gly Gly Gly Gly Ser Gly Gly Gly Gly Gly Gly Gly Gly Gly Gly Gln
65                  70                  75                  80

Gln Ile Ala Val Asp Pro Asp Gly Pro Leu Glu Leu Thr Gly Asp Leu
                85                  90                  95

Leu Thr Leu Asn Thr Lys Thr Pro Ile Tyr Val Ser Asp Arg Ala Val
            100                 105                 110

Ser Leu Leu Ile Asp Asp Asp Thr Leu Ala Thr Lys Gln Val Asn Gly
        115                 120                 125

Ala Leu Met Val Lys Thr Ala Ala Pro Leu Asn Ser Gly Thr Gly Gly
    130                 135                 140

Gly Val Thr Leu Gly Phe Asp Pro His Thr Met Ala Leu Asp Ser Val
145                 150                 155                 160

Thr Gly Val Leu Lys Val Leu Val Asp Ser Gln Gly Pro Leu Gln Ala
                165                 170                 175

Asp Thr Gly Gly Ile Thr Leu Gln Phe Asn Thr Gln Asp Phe Val Val
            180                 185                 190

Asn Asn Gly Thr Leu Ala Leu Ala Ser Ser Val Gly Pro Thr Tyr Leu
        195                 200                 205

Ser Pro Phe Ala Thr Tyr Glu Val Thr Pro Val Leu Gly Ile Ser Gln
    210                 215                 220

Arg Asn Gly Asn Val Lys Ser Lys Gly Leu Gln Asn Trp Ser Ile Gly
225                 230                 235                 240

Tyr Tyr Ile Tyr Met Val Ser Ser Ala Gly Ile Val Asn Gly Leu Ile
                245                 250                 255

Thr Leu Glu Leu Ala Gln Glu Leu Thr Gly Ala Ser Gly Glu Asn Ser
            260                 265                 270

Leu Thr Ser Gly Leu Asn Phe Thr Phe Val Leu Ser Pro Met Tyr Pro
        275                 280                 285

Ile Glu Thr Glu Val Asn Leu Ser Leu Ile Val Pro Pro Thr Val Ser
    290                 295                 300

Pro Thr Asn Gln Asn Arg Val Phe Val Pro Asn Ser Asn Gln Ser Asp
305                 310                 315                 320

Val Gly Tyr Leu Gly Leu Pro Pro Gln Thr Lys Asp Asn Trp Tyr Val
                325                 330                 335

Pro Ile Asp Ser Pro Gly Leu Arg Leu Val Ser Phe Met Pro Thr Ala
            340                 345                 350

Thr Gly Asn Glu Lys Phe Gly Gln Gly Thr Leu Gly Tyr Cys Ala Ala
        355                 360                 365

Thr Ile Gln Asn Thr Pro Ser Gly Thr Thr Pro Ser Asp Ala Leu Ala
    370                 375                 380

Phe Thr Val Ser Leu Pro Gln Thr Ser Gly Ser Asn Trp Phe Asp Gln
385                 390                 395                 400
```

Tyr Ala Pro Asp Thr Val Val Thr Thr Gly Pro Ile Pro Phe Ser Tyr
                405                 410                 415

Gln Gly Tyr Val Tyr Ser Pro Asn Gly Asn Asn His Ala Pro Ser Pro
            420                 425                 430

<210> SEQ ID NO 33
<211> LENGTH: 474
<212> TYPE: PRT
<213> ORGANISM: Fowl adenovirus serotype 4, strain FAdV-4 ON1

<400> SEQUENCE: 33

Met Leu Arg Ala Pro Lys Arg Arg His Ser Glu Thr Glu Ala Gly Pro
1               5                   10                  15

Ser Pro Ala Pro Ile Lys Arg Pro Lys Arg Met Val Arg Ala Ser Gln
            20                  25                  30

Leu Asp Leu Val Tyr Pro Phe Asp Tyr Val Ala Asp Pro Val Gly Gly
        35                  40                  45

Leu Asn Pro Pro Phe Leu Gly Gly Ser Gly Pro Leu Val Asp Gln Gly
    50                  55                  60

Gly Gln Leu Thr Leu Asn Val Thr Asp Pro Ile Ile Lys Asn Arg
65                  70                  75                  80

Ser Val Asp Leu Ala His Asp Pro Ser Leu Asp Val Asn Ala Gln Gly
                85                  90                  95

Gln Leu Ala Val Ala Val Asp Pro Glu Gly Ala Leu Asp Ile Thr Pro
            100                 105                 110

Asp Gly Leu Asp Val Lys Val Asp Gly Val Thr Val Met Val Asn Asp
        115                 120                 125

Asp Trp Glu Leu Ala Val Lys Val Asp Pro Ser Gly Gly Leu Asp Ser
    130                 135                 140

Thr Ala Gly Gly Leu Gly Val Ser Val Asp Asp Thr Leu Leu Val Asp
145                 150                 155                 160

Gln Gly Glu Leu Gly Val His Leu Asn Gln Gln Gly Pro Ile Thr Ala
                165                 170                 175

Asp Ser Ser Gly Ile Asp Leu Glu Ile Asn Pro Asn Met Phe Thr Val
            180                 185                 190

Asn Thr Ser Thr Gly Ser Gly Val Leu Glu Leu Asn Leu Lys Ala Gln
        195                 200                 205

Gly Gly Ile Gln Ala Gly Ser Ser Gly Val Gly Val Ser Val Asp Glu
    210                 215                 220

Ser Leu Glu Ile Val Asn Asn Thr Leu Glu Val Lys Pro Asp Pro Ser
225                 230                 235                 240

Gly Pro Leu Thr Val Ser Ala Asn Gly Leu Gly Leu Lys Tyr Asp Ser
                245                 250                 255

Asn Thr Leu Ala Val Thr Ala Gly Ala Leu Thr Val Val Gly Gly Gly
            260                 265                 270

Ser Val Ser Thr Pro Ile Ala Thr Phe Val Ser Gly Ser Pro Ser Leu
        275                 280                 285

Asn Thr Tyr Asn Ala Thr Ile Val Asn Ser Ser His Pro Phe Ser
    290                 295                 300

Cys Ala Tyr Tyr Leu Gln Gln Trp Asn Val Gln Gly Leu Leu Phe Thr
305                 310                 315                 320

Ser Leu Tyr Val Lys Leu Asp Ser Thr Thr Met Gly Thr Arg Pro Gly
                325                 330                 335

Asp Asn Ser Ser Ala Asn Ala Lys Trp Phe Thr Phe Trp Val Ser Ala
            340                 345                 350

```
Tyr Leu Gln Gln Cys Asn Pro Ser Gly Ile Gln Ala Gly Thr Val Ser
            355                 360                 365

Pro Ser Thr Ala Ala Leu Ala Asp Phe Glu Pro Met Ala Asn Arg Ser
370                 375                 380

Val Ser Ser Pro Trp Thr Tyr Ser Ala Asn Ala Tyr Tyr Gln Pro Pro
385                 390                 395                 400

Ser Gly Glu Phe Gln Val Phe Thr Pro Val Val Thr Gly Ala Trp Asn
            405                 410                 415

Pro Gly Asn Ile Gly Ile Arg Val Leu Pro Val Pro Val Thr Ala Ser
            420                 425                 430

Gly Asp Arg Tyr Thr Leu Leu Cys Tyr Ser Leu Gln Cys Thr Asn Ser
            435                 440                 445

Ser Ile Phe Asn Pro Ala Asn Ser Gly Thr Met Ile Val Gly Pro Val
            450                 455                 460

Leu Tyr Ser Cys Pro Ala Ala Ser Val Pro
465                 470

<210> SEQ ID NO 34
<211> LENGTH: 195
<212> TYPE: PRT
<213> ORGANISM: Fowl adenovirus serotype 4, strain FAdV-4 ON1

<400> SEQUENCE: 34

Met Glu Glu Arg Asp Ala Ala Pro Glu Pro Met Glu Glu Ala Pro Leu
1               5                   10                  15

Ala Glu Glu Glu Leu Ala Ala Ala Glu Ala Ala Asn Pro Asn
            20                  25                  30

Glu Asn Met Val Leu Ala Cys Met Glu Arg Met Arg Val Val Val Lys
            35                  40                  45

Asn Cys Val Cys His Asn Tyr Gly Leu Arg Asn Leu Gly Leu Ser Val
        50                  55                  60

Gly Thr Gly Val Tyr Cys Arg Tyr Gly Asp Lys Leu Cys Glu Gly Leu
65                  70                  75                  80

Ser Glu Asp Tyr Gly Val Ala Gly Asn Tyr Phe Val Cys Ala Trp Ala
                85                  90                  95

Cys Ala Met Phe Ser Ser Phe Gly Pro Met Val Val His His Leu Gln
            100                 105                 110

Gly Val Val Gly Met Met Ile His Val Pro Leu Tyr Pro Ile Asp Arg
        115                 120                 125

Arg Ala Glu Phe Leu Met Val Val Ser Gln Leu Gly Ala Leu Gly Ala
130                 135                 140

Leu Pro Cys His Tyr Leu Arg Lys Met Glu Ile Ser Val Glu His Asn
145                 150                 155                 160

Ile Thr Arg Phe Tyr Ala Pro Asp Trp Phe Leu Glu Ser Val Asn Leu
                165                 170                 175

Leu Tyr Asp Trp Thr Arg Glu Gln Arg Glu Ala Phe Gly Gln Met
            180                 185                 190

Asp Asp Gln
        195

<210> SEQ ID NO 35
<211> LENGTH: 88
<212> TYPE: PRT
<213> ORGANISM: Fowl adenovirus serotype 4, strain FAdV-4 ON1

<400> SEQUENCE: 35
```

```
Met Val Leu Ile Val Leu Tyr Phe Ile Ile Arg Glu Trp Thr Gly Glu
1               5                   10                  15

Val Pro Lys Ala Arg Cys Thr Pro Glu Val Arg Ser Leu Arg Arg
            20                  25                  30

Arg Gly Ser Gly Arg Trp Val Leu Ser Ala Asn Pro Leu Tyr Ser Ser
        35                  40                  45

Leu Arg Ile Gly Leu Gly Ala Ser Arg Pro Leu Pro Val Pro Val
    50                  55                  60

Asn Pro Tyr Ser Glu Leu Glu Asp Pro Tyr Asp His Val Tyr Thr Ser
65                  70                  75                  80

Ile Ala Pro Thr Glu Thr Gln Val
                85
```

<210> SEQ ID NO 36
<211> LENGTH: 178
<212> TYPE: PRT
<213> ORGANISM: Fowl adenovirus serotype 4, strain FAdV-4 ON1

<400> SEQUENCE: 36

```
Met Val Arg Trp Met Glu Arg Lys Arg Thr Asp Phe Ile Phe Val
1               5                   10                  15

Pro Ser Gly Leu Val Leu Gly Ser Met Val Cys Cys Lys Met Ala Leu
            20                  25                  30

Arg Thr Met Cys Phe Glu Ile Ser Thr Ser Lys Val Pro Arg Cys Val
        35                  40                  45

Pro Phe Met Glu Val Pro Ile Asn Tyr Leu Cys Cys Lys Thr Asn
    50                  55                  60

Val Arg Met Thr Leu Val Cys Pro Arg Gly Asn Gly Ser Cys Ile Thr
65                  70                  75                  80

Gln Ser Val Cys Thr Lys Ser Met Leu Val Asp Phe Val Pro Leu Pro
                85                  90                  95

Tyr Arg Glu Ile Val Phe Arg Gly Val Cys Tyr Leu Pro Ala His Arg
                100                 105                 110

Arg Ala Thr Tyr Ser Asp Met Glu Glu Trp Phe Met His Val His Gly
            115                 120                 125

Pro Phe Cys Asp Cys Glu Asn Gly Cys Asp Arg Cys Glu Val Lys Ser
        130                 135                 140

Pro Met Asn Leu Phe Tyr Leu Ala Gln Met Ala Cys Leu Lys Leu Ala
145                 150                 155                 160

Phe Asp Arg Arg Arg Ala Arg Val Thr His Asn Arg Lys Ser Pro Phe
                165                 170                 175

Phe Lys
```

<210> SEQ ID NO 37
<211> LENGTH: 113
<212> TYPE: PRT
<213> ORGANISM: Fowl adenovirus serotype 4, strain FAdV-4 ON1

<400> SEQUENCE: 37

```
Met Glu Cys Gly Cys Cys Ser Phe Ser Val Leu Val Pro Pro Arg
1               5                   10                  15

Glu Pro Ile Val Leu His Gln Glu Glu Ile Glu Arg Met Ile Glu Tyr
            20                  25                  30

His Leu Thr Leu Ala Ile Leu Asp Leu Asn Thr Phe Asn Gly Asp Glu
            35                  40                  45
```

```
Phe Leu Arg Tyr Ile His Ser Ser Ile Tyr Val Ala Val Gly Cys Arg
 50                  55                  60

Cys Ser Arg Tyr Leu Arg Leu Arg Ser Gly Val His Leu Val Val Asn
 65                  70                  75                  80

Cys Asp Ile Arg Phe Gln Ala Ala Ile Pro Leu Thr Ala Ser Asp Lys
                 85                  90                  95

Arg Glu Phe Leu Gln Phe Ile Ser Arg Arg Leu Leu Thr Phe Arg Pro
                100                 105                 110

Arg

<210> SEQ ID NO 38
<211> LENGTH: 560
<212> TYPE: PRT
<213> ORGANISM: Fowl adenovirus serotype 4, strain FAdV-4 ON1

<400> SEQUENCE: 38

Met Phe Ala Pro Asn Leu Phe Asp His Leu Leu Arg Tyr His Gln Lys
  1               5                  10                  15

Met Thr Pro His Thr Gly Val Val Thr Leu Leu Trp Arg Gln Glu Gly
                 20                  25                  30

Val Leu Arg Met Ser Asp Leu Ile Gln Glu Val Met Ile Val Asn Val
             35                  40                  45

Thr Glu Phe Leu Gly Arg Phe Pro Lys Asn Lys Arg Met His Cys Ile
 50                  55                  60

Gly His Asp Leu Gly Ala His Val Cys Ala Ala Val Cys Arg Gln Phe
 65                  70                  75                  80

Tyr Gln Val His Gly Arg Lys Cys His Arg Ile Val Ala Leu Ser Pro
                 85                  90                  95

Ser Pro Ala Phe Val Ser Thr Ser Leu Trp Arg Tyr Asn Arg Glu Arg
                100                 105                 110

Ala Leu Ser Ser Lys Asp Ala Lys Tyr Val Val Val Leu Ala Ser Asn
            115                 120                 125

Arg Asn Arg Phe Ser Asn Pro Arg Leu Phe Gly His Glu Tyr Ile Thr
130                 135                 140

Thr Asp Trp Asp Gly Leu Gln Ser Asp Met Cys Asp Tyr Arg Lys Ser
145                 150                 155                 160

Leu Thr Ile Tyr Lys Thr Ile Cys Gly Thr Asn Tyr Tyr Leu Lys Thr
                165                 170                 175

Val Cys Glu His Ile Glu Val Lys Leu Ser Ser Pro Leu Thr Tyr Ser
            180                 185                 190

Gln Val Cys Ser His Leu Ser Ser Ile Phe Val Phe Met Arg Ser Leu
        195                 200                 205

Asp Val Leu Gly Ala Met Thr Met Phe Arg Ser Val Ser Arg Pro Pro
210                 215                 220

Ile Gly Tyr Tyr Gly His Phe His Thr Ala Trp Asn Gly Tyr Ser Ile
225                 230                 235                 240

Ser Lys Asp Tyr Arg Tyr Pro Leu Tyr Phe Asp Ser Glu Thr Ala Trp
                245                 250                 255

Tyr Ala Thr His Val Gly Asp Gly Val Thr Pro Tyr Gly Ala Val Val
            260                 265                 270

Ile Leu Ser Tyr Ser Gly Ser Ser Thr Arg Ile Thr Ala Gly Ser Arg
        275                 280                 285

Arg Val Phe Arg Glu Met Ile Thr Tyr Gly Thr Gln Tyr Glu Leu Glu
    290                 295                 300
```

Thr Ala Leu Ile Pro Lys Glu Ser Leu Ser Arg Phe Val Val Asn His
305                 310                 315                 320

Thr Asp Arg Ala Ile Leu Leu Ser Ala His Val Met Trp Ser His Gly
            325                 330                 335

Cys Glu Asp Asp Asn Cys Ala Val Pro Met Ser Ser Phe Phe Val Gln
            340                 345                 350

Gly Val Glu Cys Lys Trp Phe Thr Ala Tyr Ser Ser Val Cys Gly Leu
        355                 360                 365

Val Gly Glu Ala Arg Met Met Pro Ala Tyr Arg Asp Met Leu Asp Val
    370                 375                 380

Lys Gly Ala Gly Met Thr Met Gln Val Pro Pro Lys Pro Gly Arg Cys
385                 390                 395                 400

Leu Arg Asn Arg Ala Gly Met Ser Gly Lys Leu Thr Ser Lys Leu Ser
            405                 410                 415

Glu Met Asn Val Thr Val Gly Ala Lys Val Asp Leu Glu Leu Ser Pro
            420                 425                 430

Lys His Trp Phe Phe Glu Leu Phe Gly Ile Asp Met Val Lys Asp Gly
        435                 440                 445

Gly Leu Lys Arg Ala Val Phe Ser Tyr Trp Asp Ile Cys Arg Glu Ala
    450                 455                 460

Arg Pro Phe Val Thr Val Arg Ala Asp Arg Arg Gly Asn Phe Gln
465                 470                 475                 480

Phe Ser Phe Lys Gln Glu Gly Ser Tyr Thr Leu Phe Phe Asp Tyr Ala
            485                 490                 495

Phe Glu Val Val Glu Trp Thr Cys His Val Ser Lys Ala Pro Pro Thr
        500                 505                 510

Arg Ala Pro Ser Thr Ala Ala Pro Asp Thr Ala Ala Val Val Glu Trp
            515                 520                 525

Arg Asp Ile Arg Asn Ala Ser Ser Asp Ser Val Ala Pro Ser Val Val
530                 535                 540

Ser Asp Gly Ile Ser Ile Gln Ala Thr Pro Glu Ser Tyr Val Ile Pro
545                 550                 555                 560

<210> SEQ ID NO 39
<211> LENGTH: 93
<212> TYPE: PRT
<213> ORGANISM: Fowl adenovirus serotype 4, strain FAdV-4 ON1

<400> SEQUENCE: 39

Met Pro Gly Thr Lys Lys Met Met Ser Phe Glu Trp Leu Asn Pro Ser
1               5                   10                  15

Leu Ile Ser Ser Lys Val Ser Pro Met His Gly Ala Leu Ser Asn Ser
            20                  25                  30

Pro Arg Ser Tyr His Leu Arg Thr Ala Asn Ser Ser Leu Asn Ser Ser
        35                  40                  45

Val Phe Leu Gly Gly Pro Ser Ser Leu His Ser Ala Thr Glu Gln Gly
    50                  55                  60

Ser Glu Pro Leu Lys Val His Phe Gln Arg Glu Pro Ser Ser Lys Val
65                  70                  75                  80

Asp Pro Glu Gly Arg Pro His Lys Ala Ile Lys Thr Asn
            85                  90

<210> SEQ ID NO 40
<211> LENGTH: 221
<212> TYPE: PRT
<213> ORGANISM: Fowl adenovirus serotype 4, strain FAdV-4 ON1

<400> SEQUENCE: 40

Met Ala Glu Glu Trp Leu Asp Leu Phe His Pro Ser Thr Ser Pro Asn
1               5                   10                  15

Pro Glu Gly Glu Gly Glu Asp Met Ser Leu Glu Thr Glu Cys His Ala
            20                  25                  30

Pro Leu Gln Tyr Ile Ser Met Leu Ser Phe Asp Asp Leu Leu Ala Ala
        35                  40                  45

Ala Gly Pro Pro Glu Tyr Ser Pro Glu Glu Asn Gln Glu Thr Pro Pro
    50                  55                  60

Leu Glu Thr Ile Glu Val Gly Asp Ile Met Ala Glu Leu Gly Ile Pro
65                  70                  75                  80

Ile Glu Gly Pro Pro Thr Ser Pro Ser Asp Ser Ser Ser Leu Asp
                85                  90                  95

Ser Val Leu Phe Ser Gly Val Asp Leu Tyr Asp Leu Asp Tyr Thr Ile
                100                 105                 110

Val Phe Ser Arg Leu Arg Glu Phe Trp Gln Ser His Gly Ala Tyr Leu
            115                 120                 125

Lys Thr Val Ala Ser Leu Glu Cys Met Gln Asn Asp Arg Lys Phe Gln
130                 135                 140

Glu Ala Tyr Cys Ser Leu Val Arg Met His Ala Val Ser Glu Asp Ala
145                 150                 155                 160

Lys Glu His Leu Asn Glu Leu Leu Asp Glu Ser Asn Tyr Gln His
                165                 170                 175

Cys Glu Pro Leu Asn Asp Met Leu Asp Leu Gly Phe Arg Trp Leu Asn
            180                 185                 190

Asp Leu Lys Gly Gly Met Glu Trp Cys Met Thr Ala Leu Asp Arg
            195                 200                 205

Ala Ser Lys Val Met Pro Leu Thr Asp Tyr Gln Pro Gln
    210                 215                 220

<210> SEQ ID NO 41
<211> LENGTH: 97
<212> TYPE: PRT
<213> ORGANISM: Fowl adenovirus serotype 4, strain FAdV-4 ON1

<400> SEQUENCE: 41

Met Val Met Leu Asn Ile Lys Leu Leu Thr Pro Val Glu Phe Ser Met
1               5                   10                  15

Leu Thr Ile Asn Met Asp Leu Val Leu Phe Val Tyr Ser Pro Trp Gln
            20                  25                  30

His Thr Ile Tyr Gly His Pro Thr Pro Pro Pro Leu Tyr Ile Asn
        35                  40                  45

Asp Gly Val Ile Gly Gly Ala Leu Ser His Trp Leu Ser Met Met Ser
    50                  55                  60

Cys Ser Tyr Thr Leu Ala Arg Ser Thr Tyr Ile Gly Arg Pro Gly Arg
65                  70                  75                  80

Gln Val Gln Thr Asp Arg Pro Gly Thr Ser Arg Leu Asn Gly Ala Leu
            85                  90                  95

His

<210> SEQ ID NO 42
<211> LENGTH: 52
<212> TYPE: PRT
<213> ORGANISM: Fowl adenovirus serotype 4, strain FAdV-4 ON1

-continued

<400> SEQUENCE: 42

Met Val Ile Phe Phe Asn Gln Thr Pro Thr Pro Leu Gly Thr Pro Leu
1               5                   10                  15

Tyr Thr Pro Leu Tyr Arg Arg Pro Pro Pro Met Ile Thr Pro Leu Tyr
            20                  25                  30

Ser Arg Pro Pro Pro Met Thr Thr Pro Leu Tyr His Tyr Ser Gln Trp
        35                  40                  45

Asp Pro Ile His
    50

<210> SEQ ID NO 43
<211> LENGTH: 271
<212> TYPE: PRT
<213> ORGANISM: Fowl adenovirus serotype 4, strain FAdV-4 ON1

<400> SEQUENCE: 43

Met Gly Ser His Pro Leu Thr Ser His Asp Pro Arg Trp Pro Tyr Glu
1               5                   10                  15

Val Ala Thr Ile Ser Phe Thr Leu Leu Asp Pro Met Pro Arg Gly Gly
            20                  25                  30

Glu Asp Gly Arg Arg Pro Tyr Leu Asp Asn Gln Leu Ala Glu Ala Leu
        35                  40                  45

Gln Phe Ser Pro Ala Leu Thr Pro Asp Gln Ser Asn Ala Leu Glu Phe
    50                  55                  60

Thr Thr Trp Leu Val Lys Gly Arg Arg Leu Leu His Lys Gly Lys Gln
65                  70                  75                  80

Tyr Arg Leu Tyr Asn Met Ala Ala Arg Ile Cys Ser Ile His Gln Trp
                85                  90                  95

Glu Arg Ser Glu Ala Gln Leu Thr Met Glu Ala Val Ala Asn Gly Leu
            100                 105                 110

Trp Asp Leu Pro Asp Glu Ile Leu Gly Ser Pro Leu Leu His Asn Thr
        115                 120                 125

Gly Ile His Thr Trp Gly Trp Gly Val Pro Val Thr Thr Glu Ile Ser
    130                 135                 140

Leu Lys Met Val Leu Lys Thr Leu Arg Val Asn Thr Pro Phe Asn Arg
145                 150                 155                 160

Gln Gly Glu Met Pro Ile Pro Val Ser Lys Glu Val His Val Glu Ala
                165                 170                 175

Pro Gln His Phe Glu Asp Met Leu Gln Gly Val Leu Thr Thr Thr Asp
            180                 185                 190

Leu Lys Lys His Ile Pro Arg Pro Ile Phe Ser Arg Phe Phe Asn Glu
        195                 200                 205

Lys Pro Ser Val Trp Ala Tyr Lys Thr Phe Lys Tyr Ser Ala Gly Glu
    210                 215                 220

Glu Lys Trp Arg Val Val Pro Thr Glu Gly Pro Tyr Gly Gly Pro
225                 230                 235                 240

Lys Asn Pro Val Ser Leu Gln Asn Leu Ala Lys Met Gly Val Leu Glu
                245                 250                 255

Asn Cys Leu Lys Met Lys Arg Ala Gly Leu Arg Phe Met Pro Tyr
            260                 265                 270

<210> SEQ ID NO 44
<211> LENGTH: 79
<212> TYPE: PRT
<213> ORGANISM: Fowl adenovirus serotype 4, strain FAdV-4 ON1

```
<400> SEQUENCE: 44

Met Asp Phe Glu Pro His Val Ser Asp Gly Glu Glu Leu Thr Leu Ile
1               5                   10                  15

Phe Asn Ser Asp Phe Ala Arg Arg Arg Ser Phe Gly Leu Arg Lys Phe
            20                  25                  30

Ser Thr Leu Ser Ile Ile Asn Trp Ala Thr Asp Phe Gly Thr Asp Val
        35                  40                  45

Arg Lys Glu Glu Val Leu Lys Leu Asn Phe Asn Ser Asn Phe Glu Arg
    50                  55                  60

Arg Arg Ser Ser Gly Leu Arg Lys Ile Phe His Cys Tyr Asn His
65                  70                  75

<210> SEQ ID NO 45
<211> LENGTH: 158
<212> TYPE: PRT
<213> ORGANISM: Fowl adenovirus serotype 4, strain FAdV-4 ON1

<400> SEQUENCE: 45

Met Asn Lys Trp Phe Lys Phe Gln Met Thr Met Tyr Leu Val Phe Gly
1               5                   10                  15

Ala Ala Val Pro Glu Trp Cys Gln Arg Pro Glu Val Phe Arg Cys Val
            20                  25                  30

His Arg Gly Leu Lys Phe Ile Trp Thr Lys Leu Val Glu Lys Tyr Ser
        35                  40                  45

Pro Glu Cys Cys Pro Leu Lys Tyr Met Phe Gly Leu Gln Glu Phe Ser
    50                  55                  60

Val Cys Glu Cys His Ala Thr Leu Leu Ile Cys Ile His Cys Ser Asp
65                  70                  75                  80

Gln Thr Lys Gly Lys Leu Glu Lys Cys Arg Ser Asp Met Arg Arg Phe
                85                  90                  95

Leu His Leu Val Phe Tyr Arg Asp Thr Gly Ser Pro Cys Gln Val Trp
            100                 105                 110

Leu Lys Leu Tyr Asp Asn Gln Trp Cys Pro Glu Glu Tyr Arg Met Gly
        115                 120                 125

Arg Trp Gly Val Lys Glu Ala Phe Gln Cys Leu Gly Ala Trp Arg
    130                 135                 140

Val Cys Thr Gly Leu Arg Thr Ala Asp Asp Val Ile Val Asp
145                 150                 155

<210> SEQ ID NO 46
<211> LENGTH: 135
<212> TYPE: PRT
<213> ORGANISM: Fowl adenovirus serotype 4, strain FAdV-4 ON1

<400> SEQUENCE: 46

Met Leu Gly Tyr Leu Met Leu Arg Val Pro Leu Trp Glu Leu Asn Leu
1               5                   10                  15

Ala Met Phe His Asp Phe Arg Arg Asp Val Ile Asn Ala Trp Glu Lys
            20                  25                  30

Leu Asp Leu Gly Lys Val Phe Pro Gly Ala Val Thr Gly Phe Phe Tyr
        35                  40                  45

Leu Tyr Pro Phe Gln Asp Gly Phe Cys Ile Glu Cys Phe Leu Pro Cys
    50                  55                  60

Thr Asp Phe Gly Ser Ala Tyr Ala Glu Gly Val Gly Leu Ala Val Lys
65                  70                  75                  80

Cys Leu Phe Phe Gly Lys Tyr Pro His Glu Ser Glu Lys Trp Leu Lys
```

```
                85                  90                  95
Gly Val Cys Leu Leu Arg Asn Gly Gly Tyr Ala Glu Glu Phe Arg Leu
            100                 105                 110

Gly Glu Tyr Cys Val Thr Ala Glu Ala Val Gly Ser Arg Glu Gly Cys
            115                 120                 125

Ile Tyr Glu Cys Met Tyr Glu
            130                 135

<210> SEQ ID NO 47
<211> LENGTH: 820
<212> TYPE: PRT
<213> ORGANISM: Fowl adenovirus serotype 4, strain FAdV-4 ON1

<400> SEQUENCE: 47

Met Ala Asn Phe Ser Pro Val Arg His Glu Gly His Ile Asn Tyr Phe
1               5                   10                  15

Trp Tyr Gly Gln His Gly Met Ala Pro Pro Arg Ile His Gly Pro Leu
            20                  25                  30

His Asp Asn Asp Met Ile Tyr Trp Arg Leu Arg Asp Arg Gly Phe Leu
        35                  40                  45

Arg Gly Gly Arg Glu Lys Asn Leu Ile Leu Val His Gly Trp His
    50                  55                  60

Gly Leu His Arg Thr Phe Asp Ile Phe Phe Lys Phe Leu Arg Phe His
65                  70                  75                  80

Gln Lys Met Thr Pro Asp Val Gly Val Leu Leu Val Asp Trp Gly Val
                85                  90                  95

Gln Gly Ala Asp Asn Leu Ile Leu Gly Asp Ala Ala Tyr His Ala Val
            100                 105                 110

Thr Ile Asn Ile Asp Gly Leu Leu Lys Asn Ile Asn Arg Thr Asp Leu
            115                 120                 125

His Cys Ile Gly His Ser Leu Gly Ala His Ala Cys Gly Ala Ile Cys
            130                 135                 140

Arg Arg Phe Asn Gln Leu Gln Asn Arg Lys Cys Thr Arg Ile Val Gly
145                 150                 155                 160

Leu Asp Pro Ala Gly Pro Leu Phe Lys Thr Asn Ser Pro Tyr Pro Tyr
                165                 170                 175

Leu Thr Lys Ala Arg Leu Ser Lys Lys Asp Ala Asp Tyr Val Ala Leu
            180                 185                 190

Phe Met Thr Asn Arg Arg Met Met Gly Leu His Glu Leu Glu Gly Asp
            195                 200                 205

Glu Tyr Ile Thr Pro Tyr Ile Asp Gly Thr Tyr Leu Asn His Cys Pro
    210                 215                 220

Phe Ile Gly Lys Trp Thr Gly Thr Ile Thr Ala Glu Asn Tyr Gln Gly
225                 230                 235                 240

Arg Lys Val Thr Glu Tyr Ile Asp Leu Gly Thr Val Ala Lys Ser Gly
                245                 250                 255

Val Ile Pro His Thr Met Asp Ala Cys Ser His Leu Met Ala Pro Val
            260                 265                 270

Leu Phe Met Val Ser Leu Asp Thr Arg Gln Gly Leu Pro Ala Phe Arg
            275                 280                 285

Tyr Ala Glu Asn Pro Pro Gln Asp Gln Gly Ala Met His Thr Val Trp
        290                 295                 300

Asn Gly Tyr Thr Ile Gly Lys Asp Tyr Gln Tyr Pro Ala Tyr Phe Lys
305                 310                 315                 320
```

```
His Glu Thr Ile Trp Leu Ser Thr Leu Thr Thr Asp Ala Asn Gln Leu
                325                 330                 335

Ser Pro Phe Glu Phe Gln His Glu Asp Ser Ile Asp Pro Ser Phe Met
            340                 345                 350

Ala Met Ala Ile Ser Asp Lys Gly Cys Ile Ser Ala Gly Ser His Leu
        355                 360                 365

Ser Tyr His Tyr Ser Val Ile Pro Tyr Gly Asn Lys Tyr Asp Leu Val
    370                 375                 380

Thr Ser Phe Ser Ala Leu Ser Pro Gly Met Ala Asp Thr His Phe Leu
385                 390                 395                 400

Glu Val Tyr Met Asn Tyr Lys His Cys Pro Val Tyr Leu Ala Arg Phe
                405                 410                 415

Leu Ile Pro Lys Pro Tyr Gln Gln Leu Pro Arg Pro Thr Thr Ala
            420                 425                 430

Gly Leu Ser Ser Glu Met Leu Ser Cys Arg Lys Gln Thr Thr Tyr Thr
        435                 440                 445

Trp Ser Cys Tyr Arg Thr Trp Lys Gln Ala Val Leu Pro Val Tyr Arg
    450                 455                 460

Gln Gln Leu Asp Leu Thr Gly Asp Gly Arg His Asn Ile Gln Val Pro
465                 470                 475                 480

Pro Lys His Gly Cys Leu Lys Glu Gln Ser Asn Phe Thr Asp Met Phe
                485                 490                 495

Arg Thr Tyr Met Gly Ala Tyr Glu Val Leu Thr Asp Gln Thr Val Thr
            500                 505                 510

Val Thr Ser Leu Pro Ser Pro Phe Glu Leu Ile Arg Ile Ala Leu Arg
        515                 520                 525

Asp Pro Ala Ser His Thr Ile Gln Asn Ile Met Thr Tyr Trp Asp Met
    530                 535                 540

Cys Asp Pro Val Ala Ser Thr Cys Ser Phe Thr Val Asn Arg Ala Thr
545                 550                 555                 560

Arg Thr Leu Asn Ile Thr Cys Pro Asp Pro Lys Thr Tyr Trp Ile Ser
                565                 570                 575

Phe Phe Tyr Gln Trp Glu Glu Val Leu Leu Lys Ile Thr Val His Pro
            580                 585                 590

Lys Pro Thr Thr Thr Thr Thr Thr Thr Thr Thr Thr Thr Thr Thr
            595                 600                 605

Thr Pro Thr Thr Thr Thr Thr Thr Pro Thr Thr Thr Thr Thr Thr
        610                 615                 620

Thr Thr Thr Thr Pro Thr Thr Thr Thr Thr Thr Pro Thr Thr Thr
625                 630                 635                 640

Thr Thr Thr Thr Pro Thr Thr Thr Thr Thr Thr Pro Thr Thr Thr
                645                 650                 655

Ser Thr Glu Ser Ile Thr Glu Pro Ser Ser Ala Cys Asp Glu Glu
            660                 665                 670

Asp Glu Asp Cys Trp Phe Glu Lys Tyr Arg Asp Gln Ile Glu Val Pro
        675                 680                 685

Gln Lys Val Gln Leu Pro Phe Lys Val Ala Asn Asn Glu Met Ser Glu
    690                 695                 700

Pro Thr Thr Ala Ala Thr Pro Ser Ser Pro Ala Ala Ile Glu Glu
705                 710                 715                 720

Glu Ser Asn Ser Arg Ala Ser Thr Pro Pro Leu Gln Leu Thr Val
                725                 730                 735

Ala Pro Gly Thr Asn Pro Pro Leu Gln Glu Phe Leu Trp Ala Glu Pro
```

```
                    740                 745                 750
Ser Ser Lys Asp Ser Leu Arg Lys Asp Gln Asp Ser Thr Val Thr Ile
            755                 760                 765

Pro Val Thr Ile Gly Leu Leu Ala Leu Val Cys Leu Ser Val Ile Ile
        770                 775                 780

Ala Val Phe Ile Ala Leu Arg Arg Arg Gly Arg Gly Pro Arg Pro Thr
785                 790                 795                 800

Phe Ile Ile Val Pro Gly Thr Gly Asn Asn Thr Val Tyr Gln Glu Thr
                805                 810                 815

Thr Glu Met Leu
            820

<210> SEQ ID NO 48
<211> LENGTH: 178
<212> TYPE: PRT
<213> ORGANISM: Fowl adenovirus serotype 4, strain FAdV-4 ON1

<400> SEQUENCE: 48

Met Asn Arg Phe Gln Thr Glu His Asp Met Gly Gly Glu Lys Ser Ser
1               5                   10                  15

Val Lys Leu Asp Arg Phe Pro Tyr Trp Gly Thr Leu Glu Glu Ile Asp
            20                  25                  30

Arg Tyr Ala Lys Ala Asn Arg Gly Thr Val Thr Pro Ile Gly Ser Gly
        35                  40                  45

Lys His Phe Leu Val Ile Gly Asp Leu Glu Gly Thr Leu His Ala Gly
    50                  55                  60

Gln His Leu Lys Glu Tyr Cys Glu Val Leu Tyr Leu Pro Ser Pro Lys
65                  70                  75                  80

Arg Met Thr Ile Ile Gly Ile Val Asp Asn Val Ile Ser Phe Ala Asp
                85                  90                  95

Gly Leu Gln Val Val Ile Leu Val Ala Glu Asp Lys Thr Val Tyr Gly
            100                 105                 110

Tyr Glu Glu Asp Thr Leu His Lys Leu Ala Ser Thr Ile Pro Glu Phe
        115                 120                 125

Phe Arg Ile Gly Met Gln Asn Phe Gly Thr Glu Val Phe His Cys Gly
    130                 135                 140

Ser His Ile Pro Pro Leu Val Ser Ala Asp Pro Thr Pro Ser His Tyr
145                 150                 155                 160

Leu Pro Asp Arg Tyr Leu Thr His Tyr Ile Pro Val Arg Gly Gly Ala
                165                 170                 175

Ser Ala

<210> SEQ ID NO 49
<211> LENGTH: 209
<212> TYPE: PRT
<213> ORGANISM: Fowl adenovirus 1

<400> SEQUENCE: 49

Val Ala Thr Tyr His Cys Gly Asp Asn Leu Leu Glu Ser Tyr Asp Ile
1               5                   10                  15

Phe Ala Ser Leu Pro Asn Thr Asn Ala Ala Lys Val Ala Ala Tyr Cys
            20                  25                  30

Arg Leu Ala Ala Ala Gly Gly Val Val Ser Gly Thr Ile Gln Val Thr
        35                  40                  45

Ser Tyr Ala Gly Arg Trp Pro Lys Val Gly Asn Ser Val Thr Asp Gly
    50                  55                  60
```

```
Ile Lys Phe Ala Ile Val Ser Pro Pro Met Asp Lys Asp Pro Arg
 65                  70                  75                  80

Ser Asn Leu Ser Gln Trp Leu Gly Ala Thr Val Phe Pro Ala Gly Ala
                 85                  90                  95

Thr Thr Ala Leu Phe Ser Pro Asn Pro Tyr Gly Ser Leu Asn Thr Ile
            100                 105                 110

Thr Thr Leu Pro Ser Ile Ala Ser Asp Trp Tyr Val Pro Glu Ser Asn
            115                 120                 125

Leu Val Thr Tyr Thr Lys Ile His Phe Lys Pro Thr Gly Ser Gln Gln
            130                 135                 140

Leu Gln Leu Ala Ser Gly Glu Leu Val Ala Ala Lys Ser Pro
145                 150                 155                 160

Val Gln Thr Thr Lys Tyr Glu Leu Ile Tyr Leu Gly Phe Thr Leu Lys
                165                 170                 175

Gln Asn Ser Ser Gly Thr Asn Phe Phe Asp Pro Asn Ala Ser Ser Asp
            180                 185                 190

Leu Ser Phe Leu Thr Pro Pro Ile Pro Phe Thr Tyr Leu Gly Tyr Tyr
            195                 200                 205

Gln

<210> SEQ ID NO 50
<211> LENGTH: 202
<212> TYPE: PRT
<213> ORGANISM: Fowl adenovirus 1

<400> SEQUENCE: 50

Val Ala Ala Phe Thr Ser Gly Thr Ile Gly Leu Ser Ser Pro Thr Gly
 1               5                  10                  15

Asn Phe Val Ser Ser Asn Asn Pro Phe Asn Gly Ser Tyr Phe Leu
                 20                  25                  30

Gln Gln Ile Asn Thr Met Gly Met Leu Thr Thr Ser Leu Tyr Val Lys
             35                  40                  45

Val Asp Thr Thr Thr Met Gly Thr Arg Pro Thr Gly Ala Val Asn Glu
 50                  55                  60

Asn Ala Arg Tyr Phe Thr Val Trp Val Ser Ser Phe Leu Thr Gln Cys
 65                  70                  75                  80

Asn Pro Ser Asn Ile Gly Gln Gly Thr Leu Glu Pro Ser Asn Ile Ser
                 85                  90                  95

Met Thr Ser Phe Glu Pro Ala Arg Asn Pro Ile Ser Pro Val Phe
            100                 105                 110

Asn Met Asn Gln Asn Ile Pro Tyr Tyr Ala Ser Arg Phe Gly Val Leu
            115                 120                 125

Glu Ser Tyr Arg Pro Ile Phe Thr Gly Ser Leu Asn Thr Gly Ser Ile
            130                 135                 140

Asp Val Arg Met Gln Val Thr Pro Val Leu Ala Thr Asn Asn Thr
145                 150                 155                 160

Tyr Asn Leu Ile Ala Phe Thr Phe Gln Cys Ala Ser Ala Gly Leu Phe
                165                 170                 175

Asn Pro Thr Val Asn Gly Thr Val Ala Ile Gly Pro Val His Thr
            180                 185                 190

Cys Pro Ala Ala Arg Ala Pro Val Thr Val
            195                 200

<210> SEQ ID NO 51
```

```
<211> LENGTH: 210
<212> TYPE: PRT
<213> ORGANISM: Fowl adenovirus 9

<400> SEQUENCE: 51

Asp Ala Tyr Leu Glu Ser Gly Thr Asn Tyr Leu Asn Asn Phe Thr Ala
1               5                   10                  15

Gln Ala Glu Asn Ser Ser Val Phe Lys Phe Asn Cys Ala Tyr Phe Leu
            20                  25                  30

Gln Ser Trp Tyr Ser Asn Gly Leu Val Thr Ser Ser Leu Tyr Leu Lys
        35                  40                  45

Ile Asp Arg Ala Gln Phe Ser Asn Met Pro Thr Gly Gln Ser Ala Glu
50                  55                  60

Asn Ala Arg Tyr Phe Thr Phe Trp Val Pro Thr Tyr Glu Ser Leu Asn
65                  70                  75                  80

Leu Ser Arg Val Ser Thr Pro Thr Ile Thr Pro Asn Thr Val Gln Trp
                85                  90                  95

Gly Ala Phe Ser Pro Ala Gln Asn Cys Ser Gly Asn Pro Ala Phe Gln
            100                 105                 110

Tyr Asn Leu Thr Gln Pro Pro Ser Ile Tyr Phe Glu Pro Lys Ser Gly
        115                 120                 125

Ser Val Gln Thr Phe Gln Pro Val Leu Thr Gly Ala Trp Asn Thr Asp
130                 135                 140

Thr Tyr Asn Pro Gly Thr Val Gln Val Cys Ile Leu Pro Gln Thr Val
145                 150                 155                 160

Val Gly Gly Gln Ser Thr Phe Val Asn Met Thr Cys Tyr Asn Phe Arg
                165                 170                 175

Cys Gln Asn Pro Gly Ile Phe Lys Val Ala Ala Ser Asn Gly Thr Phe
            180                 185                 190

Thr Ile Gly Pro Ile Phe Tyr Ser Cys Pro Thr Asn Glu Leu Thr Arg
        195                 200                 205

Pro Thr
    210

<210> SEQ ID NO 52
<211> LENGTH: 221
<212> TYPE: PRT
<213> ORGANISM: Fowl aviadenovirus C

<400> SEQUENCE: 52

Ala Thr Tyr Glu Val Thr Pro Val Leu Gly Ile Ser Gln Arg Asn Gly
1               5                   10                  15

Asn Val Lys Ser Lys Gly Leu Gln Asn Trp Ser Ile Gly Tyr Tyr Ile
            20                  25                  30

Tyr Met Val Ser Ser Ala Gly Ile Val Asn Gly Leu Ile Thr Leu Glu
        35                  40                  45

Leu Ala Gln Glu Leu Thr Gly Ala Ser Gly Glu Asn Ser Leu Thr Ser
    50                  55                  60

Gly Leu Asn Phe Thr Phe Val Leu Ser Pro Met Tyr Pro Ile Glu Thr
65                  70                  75                  80

Glu Val Asn Leu Ser Leu Ile Val Pro Pro Thr Val Ser Pro Thr Asn
                85                  90                  95

Gln Asn Arg Val Phe Val Pro Asn Ser Asn Gln Ser Asp Val Gly Tyr
            100                 105                 110

Leu Gly Leu Pro Pro Gln Thr Lys Asp Asn Trp Tyr Val Pro Ile Asp
        115                 120                 125
```

```
Ser Pro Gly Leu Arg Leu Val Ser Phe Met Pro Thr Ala Thr Gly Asn
    130                 135                 140

Glu Lys Phe Gly Gln Gly Thr Leu Gly Tyr Cys Ala Ala Thr Ile Gln
145                 150                 155                 160

Asn Thr Pro Ser Gly Thr Thr Pro Ser Asp Ala Leu Ala Phe Thr Val
                165                 170                 175

Ser Leu Pro Gln Thr Ser Gly Ser Asn Trp Phe Asp Gln Tyr Ala Pro
            180                 185                 190

Asp Thr Val Val Thr Thr Gly Pro Ile Pro Phe Ser Tyr Gln Gly Tyr
        195                 200                 205

Val Tyr Ser Pro Asn Gly Asn Asn His Ala Pro Ser Pro
    210                 215                 220

<210> SEQ ID NO 53
<211> LENGTH: 197
<212> TYPE: PRT
<213> ORGANISM: Fowl aviadenovirus C

<400> SEQUENCE: 53

Ile Ala Thr Phe Val Ser Gly Ser Pro Ser Leu Asn Thr Tyr Asn Ala
1               5                   10                  15

Thr Ile Val Asn Ser Ser His Pro Phe Ser Cys Ala Tyr Tyr Leu
            20                  25                  30

Gln Gln Trp Asn Val Gln Gly Leu Leu Phe Thr Ser Leu Tyr Val Lys
            35                  40                  45

Leu Asp Ser Thr Thr Met Gly Thr Arg Pro Gly Asp Asn Ser Ser Ala
50                  55                  60

Asn Ala Lys Trp Phe Thr Phe Trp Val Ser Ala Tyr Leu Gln Gln Cys
65                  70                  75                  80

Asn Pro Ser Gly Ile Gln Ala Gly Thr Val Ser Pro Ser Thr Ala Ala
                85                  90                  95

Leu Ala Asp Phe Glu Pro Met Ala Asn Arg Ser Val Ser Ser Pro Trp
            100                 105                 110

Thr Tyr Ser Ala Asn Ala Tyr Tyr Gln Pro Pro Ser Gly Glu Phe Gln
            115                 120                 125

Val Phe Thr Pro Val Val Thr Gly Ala Trp Asn Pro Gly Asn Ile Gly
        130                 135                 140

Ile Arg Val Leu Pro Val Pro Val Thr Ala Ser Gly Asp Arg Tyr Thr
145                 150                 155                 160

Leu Leu Cys Tyr Ser Leu Gln Cys Thr Asn Ser Ser Ile Phe Asn Pro
                165                 170                 175

Ala Asn Ser Gly Thr Met Ile Val Gly Pro Val Leu Tyr Ser Cys Pro
            180                 185                 190

Ala Ala Ser Val Pro
        195

<210> SEQ ID NO 54
<211> LENGTH: 18
<212> TYPE: DNA
<213> ORGANISM: Artificial Sequence
<220> FEATURE:
<223> OTHER INFORMATION: Primer

<400> SEQUENCE: 54
tcggagcatg gttgttcc                                              18
```

```
<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55
tcctgatcga cttcggaga                                                  19

<210> SEQ ID NO 56
<211> LENGTH: 21
<212> TYPE: DNA
<213> ORGANISM: Artificial Sequence
<220> FEATURE:
<223> OTHER INFORMATION: Primer

<400> SEQUENCE: 56
taggaaaaag ggataggacc g                                               21

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
tagagcacgg gtcccacaat                                                 20

<210> SEQ ID NO 58
<211> LENGTH: 19
<212> TYPE: DNA
<213> ORGANISM: Artificial Sequence
<220> FEATURE:
<223> OTHER INFORMATION: Primer

<400> SEQUENCE: 58
tcctgatcga cttcggaga                                                  19

<210> SEQ ID NO 59
<211> LENGTH: 19
<212> TYPE: DNA
<213> ORGANISM: Artificial Sequence
<220> FEATURE:
<223> OTHER INFORMATION: Primer

<400> SEQUENCE: 59
ttccgctgtt ggctggatt                                                  19

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
aatatggcat gaaccgtagc                                                 20

<210> SEQ ID NO 61
<211> LENGTH: 21
<212> TYPE: DNA
<213> ORGANISM: Artificial Sequence
<220> FEATURE:
<223> OTHER INFORMATION: Primer
```

```
<400> SEQUENCE: 61
ggtgattttc ttcaatcaaa c                                              21

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
gatgggtcta ggaatatgct t                                              21

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
tgatcgtcca tttgtccgaa                                                20

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
ctcaatcggt atgcacgaaa                                                20

<210> SEQ ID NO 65
<211> LENGTH: 18
<212> TYPE: DNA
<213> ORGANISM: Artificial Sequence
<220> FEATURE:
<223> OTHER INFORMATION: Primer

<400> SEQUENCE: 65
tttgttcccg cgtccaat                                                  18
```

NON-PATHOGENIC SEROTYPE 4 FOWL ADENOVIRUS (FADV-4) AND VIRAL VECTOR THEREOF

CROSS REFERENCE TO RELATED APPLICATIONS

This is a national stage application of PCT/CA2012/000238, filed Mar. 16, 2012, which claims priority from U.S. Provisional patent application Ser. No. 61/453,297 filed Mar. 16, 2011, all of which are incorporated herein by reference in their entirety.

INCORPORATION OF SEQUENCE LISTING

A computer readable form of the Sequence Listing "6580-P39141US01_SequenceListing.txt" (196,608 bytes), submitted via EFS-WEB and amended on Apr. 9, 2015, is herein incorporated by reference.

FIELD OF THE INVENTION

The present invention relates to the techniques used in the prevention of diseases, preferably of the avian type, and more particularly, it relates to a novel non-pathogenic serotype 4 fowl adenovirus, which can be used as a viral vector.

BACKGROUND OF INVENTION

Adenoviruses (AdVs) of the genus *Mastadenovirus* have been examined as anticancer agents (Huebner, R. J., Rower W. P., Schatten, W. E., Smith, R. R, & Thomas, L. B. (1956). Studies on the use of viruses in the treatment of carcinoma of the cervix. Cancer 9(6), 1211-1218; Cody, J. J. & Douglas, J. T. (2009). Armed replicating adenoviruses for cancer virotherapy. Cancer Gene Ther 16, 473-488; Yamamoto, M. & Curiel, D. T. (2010). Current issues and future directions of oncolytic adenoviruses. Mol Ther 18, 243-250.) and vaccine vectors (Lasaro, M. O. & Ertl, H. C. J. (2009). New Insights on Adenovirus as Vaccine Vectors. Molecular Therapy 17, 1333-1339.). The problem of preexisting immunity against HAdV-5, exemplified in the STEP HIV trial that employed recombinant HAdV-5 (Buchbinder, S. P., Mehrotra, D. V., Duerr, A., Fitzgerald, D. W., Mogg, R., Li, D., Gilbert, P. B., Lama, J. R., Marmor, M. & other authors. (2008). Efficacy assessment of a cell-mediated immunity HIV-1 vaccine (the Step Study): a double-blind, randomised, placebo-controlled, test-of-concept trial. Lancet 372, 1881-1893; McElrath, M. J., De Rosa, S. C., Moodie, Z., Dubey, S., Kierstead, L., Janes, H., Defawe, O. D., Carter, D. K., Hural, J. & other authors. (2008). HIV-1 vaccine-induced immunity in the test-of-concept Step Study: a case-cohort analysis. Lancet 372, 1894-1905), has generated interest in the development of less common AdV serotypes and nonhuman AdVs as both oncolytic (Cody & Douglas, 2009; Gallo, P., Dharmapuri, S., Cipriani, B. & Monaci, P. (2005). Adenovirus as vehicle for anticancer genetic immunotherapy. Gene Ther 12, S84-S91; Shashkova, E. V., Cherenova, L. V., Kazansky, D. B. & Doronin, K. (2005). Avian adenovirus vector CELO-TK displays anticancer activity in human cancer cells and suppresses established murine melanoma tumors. Cancer Gene Ther 12, 617-626) and vaccine vectors (Barouch, D. H. (2008). Challenges in the development of an HIV-1 vaccine. Nature 455, 613-619; Lasaro & Ertl, 2009; Sharma, A., Tandon, M., Ahi, Y. S., Bangari, D. S., Vemulapalli, R. & Mittal, S. K. (2009). Evaluation of Cross-Reactive Humoral and Cell-Mediated Immune Responses among Human, Bovine and Porcine Adenoviruses. Molecular Therapy 17, 113). Fowl adenoviruses (FAdVs) of the genus *Aviadenovirus*, including species FAdV-A to FAdV-E (Adair, B. & Fitzgerald, S. (2008). Group I Adenovirus Infections. In Diseases of Poultry, 12th ed, pp. 252-266. Edited by Y. Saif, A. Fadly, J. Glisson, L. McDougald, L. Nolan & D. Swayne. Hoboken, N. J.: Wiley-Blackwell; Benkö, M., Harrach, B., Both, G., Russell, W., Adair, B., Ádam, É., de Jong, J., Hess, M., Johnson, M. & other authors. (2005). Family Adenoviridae. In Virus taxonomy Eighth report of the International Committee on the Taxonomy of Viruses, pp. 213-228. Edited by C. Fauquet, M. Mayo, J. Maniloff, U. Desselberger & L. Ball. San Diego, Calif.: Elsevier Academic Press.), are being developed as vaccine vectors. The first generation of FAdV-based vaccine vectors have proven effective at eliciting an antibody response against a delivered transgene (Corredor, J. C. & Nagy, E. (2010b). The non-essential left end region of the fowl adenovirus 9 genome is suitable for foreign gene insertion/replacement. Virus Res 149, 167-174; Ojkic, D. & Nagy, E. (2003). Antibody response and virus tissue distribution in chickens inoculated with wild-type and recombinant fowl adenoviruses. Vaccine 22, 42-48.), and in chickens have conferred protective immunity against infectious bursal disease virus (IBDV) (Francois, A., Chevalier, C., Delmas, B., Eterradossi, N., Toquin, D., Rivallan, G. H. & Langlois, P. (2004). Avian adenovirus CELO recombinants expressing VP2 of infectious bursal disease virus induce protection against bursal disease in chickens. Vaccine 22, 2351-2360; Sheppard, M., Werner, W., Tsatas, E., McCoy, R., Prowse, S. & Johnson, M. (1998). Fowl adenovirus recombinant expressing VP2 of infectious bursal disease virus induces protective immunity against bursal disease. Arch Virol 143, 915-930) and infectious bronchitis virus (Johnson, M. A., Pooley, C., Ignjatovic, J. & Tyack, S. G. (2003). A recombinant fowl adenovirus expressing the S1 gene of infectious bronchitis virus protects against challenge with infectious bronchitis virus. Vaccine 21, 2730-2736.). Analysis of the complete genomes of FAdV-1, the chicken embryo lethal orphan (CELO) virus Chiocca, S., Kurzbauer, R., Schaffner, G., Baker, A., Mautner, V. & Cotten, M. (1996). The complete DNA sequence and genomic organization of the avian adenovirus CELO. J Virol 70, 2939-2949.), and FAdV-9 (Ojkic, D. & Nagy, E. (2000). The complete nucleotide sequence of fowl adenovirus type 8. J Gen Virol 81, 1833-1837.) (species FAdV-A and FAdV-D, respectively), and the terminal genomic regions of FAdV-2, -4, -10, and -8 Corredor, J. C., Garceac, A., Krell, P. J. & Nagy, E. (2008). Sequence comparison of the right end of fowl adenovirus genomes. Virus genes 36, 331-344; Corredor, J. C., Krell, P. J. & Nagy, E. (2006). Sequence analysis of the left end of fowl adenovirus genomes. Virus genes 33, 95-106.) has shown that the FAdVs share a common genome organization.

Adenovirus-based veterinary vaccine vectors have proven to be promising tools for controlling veterinary pathogens (Bangari, D. S. & Mittal, S. K. (2006). Development of nonhuman adenoviruses as vaccine vectors. Vaccine 24, 849-862; Ferreira, T. B., Alves, P. M., Aunins, J. G. & Carrondo, M. J. T. (2005). Use of adenoviral vectors as veterinary vaccines. Gene Ther 12, S73-S83). The first generation of fowl adenovirus (FAdV) based vaccine vectors have been effectively used to induce an antibody response against an inserted foreign gene (transgene) (Corredor, J. C. & Nagy, E. (2010a). A region at the left end of the fowl adenovirus 9 genome that is non-essential in vitro has no consequences in vivo. J Gen Virol 91(1), 51-58; Ojkic & Nagy, 2003), and in chickens have conferred protective immunity against infectious bursal disease virus (Francois et al., 2004; Sheppard et al., 1998) and infectious bronchitis virus (Johnson et al., 2003).

The use of adenovirus as vectors is described in International Publication No. WO 2003/039593, which discloses an attenuated serotype 4 fowl adenovirus (FAV 4) having a deletion of about 2-3 kb and which is able to produce a cytopathic effect in cells of a QT 35 cell line and to induce protective immunity in birds, in contrast to an inactivated FAV 4 and a live natural a-pathogenic FAV 4, which show a poor immunogenicity. This virus can be used as well as a vector to heterologous nucleic acid fragments encoding for a polypeptide, allowing the immunisation of animals against FAV and other avian pathogens.

In U.S. Pat. No. 6,296,852 there is described a recombinant vector comprising a recombinant avian adenovirus which incorporates at least one heterologous nucleotide sequence, which is inserted into a non-essential region at the right hand end of the genome of the avian adenovirus between map units 60 and 100, the avian adenovirus being selected from serotypes 4, 8, 9 and 10.

Additionally, US Patent Application No. 2010/0150958 describes a coccidiosis vaccine comprising a recombinant avian adenovirus vector having a promoter operably linked to a hydrophobic signal sequence comprising a nucleic acid that encodes a membrane anchoring domain, a multiple cloning site for insertion of an ORF to allow insertion of an ORF in frame with said hydrophobic signal sequence, a polyadenylation signal; and an avian adenovirus genome. The avian adenovirus genome is selected from serotypes 1 to 12.

US Patent Application No. US 2010/0158939 discloses adenovirus vectors, human and non-human, containing polynucleotide sequences that encode one or more influenza antigens. Among the adenovirus suitable for being used as vectors, there are included several serotypes (1 to 10) of avain adenovirus, which are available in the ATCC.

Accordingly, it can be seen from the above that, even when there are several serotypes of avian adenoviruses used as viral vectors, there is a need for new adenoviruses having better characteristics, such as a high replication, that can be used to prepare viral vectors useful for immunogenic applications.

OBJECTS OF THE INVENTION

Considering the defects of the prior art, it is an object of the present invention to provide a novel isolated strain of adenovirus able to produce a high viral titer in the host.

It is a further object of the present invention to provide a viral vector of a non-pathogenic FAdV-4 having inserted an exogenous nucleotide sequence coding for at least one antigenic site of a disease of concern.

SUMMARY OF THE INVENTION

In one aspect, there is provided a novel high level replication fowl adenovirus isolate capable of reaching a viral titer of at least 3 $\log_{10}$ in chickens, which is a non-pathogenic strain of fowl adenovirus serotype 4 identified as FAdV-4 ON1. In one embodiment, the fowl adenovirus comprises a nucleotide sequence with at least 80%, at least 90%, at least 95%, at least 98% or at least 99% sequence identity to SEQ ID NO: 2. In one embodiment, the fowl adenovirus comprises or consists of the sequence of SEQ ID NO: 2.

Another aspect of the invention considers a viral vector comprising said fowl adenovirus having inserted an exogenous nucleotide sequence coding for at least one antigenic site of a disease of concern. Also provided are host cells transformed with one or more viral vectors as described herein.

A further aspect of the invention considers a method for producing said viral vector. In one embodiment, the method comprises inserting an exogenous nucleotide sequence into a nucleotide sequence from said fowl adenovirus.

In one aspect of the disclosure, there is provided an immunogenic composition comprising at least the viral vector obtained from the fowl adenovirus of the present invention having an exogenous nucleotide sequence coding for at least one antigenic site of a disease of concern inserted therein. In one embodiment, the immunogenic composition further comprises a pharmaceutically acceptable carrier.

BRIEF DESCRIPTION OF THE FIGURES

The novel features of the present invention are established particularly in the appended claims. However, the invention itself together with other objects and advantages thereof will be better understood in the following detailed description of a specific embodiment, when read along with the appended figures, in which:

Bioinformatics 23, 2947-2948.). The secondary structure of FAdV-4 fiber 1 and fiber 2 was predicted using Jpred (Cuff, J. A. & Barton, G. J. (2000). Application of multiple sequence alignment profiles to improve protein secondary structure prediction. Proteins 40, 502-511.), and the β-strands are denoted by the letter Es. The β-strands reported for the crystal structures of FAdV-1 fiber 1 (PBD ID 2IUN) (Guardado-Calvo, P., Llamas-Saiz, A. L., Fox, G. C., Langlois, P. & van Raaij, M. J. (2007). Structure of the C-terminal head domain of the fowl adenovirus type 1 long fiber. J Gen Virol 88, 2407-2416) and fiber 2 (PDB ID 2VTW) (El Bakkouri, M., Seiradake, E., Cusack, S., Ruigrok, R. W. H. & Schoehn, G. (2008). Structure of the C-terminal head domain of the fowl adenovirus type 1 short fibre. Virology 378, 169-176) are denoted with grey arrows, and the β-strand letter designations are indicated.

Figure 6:
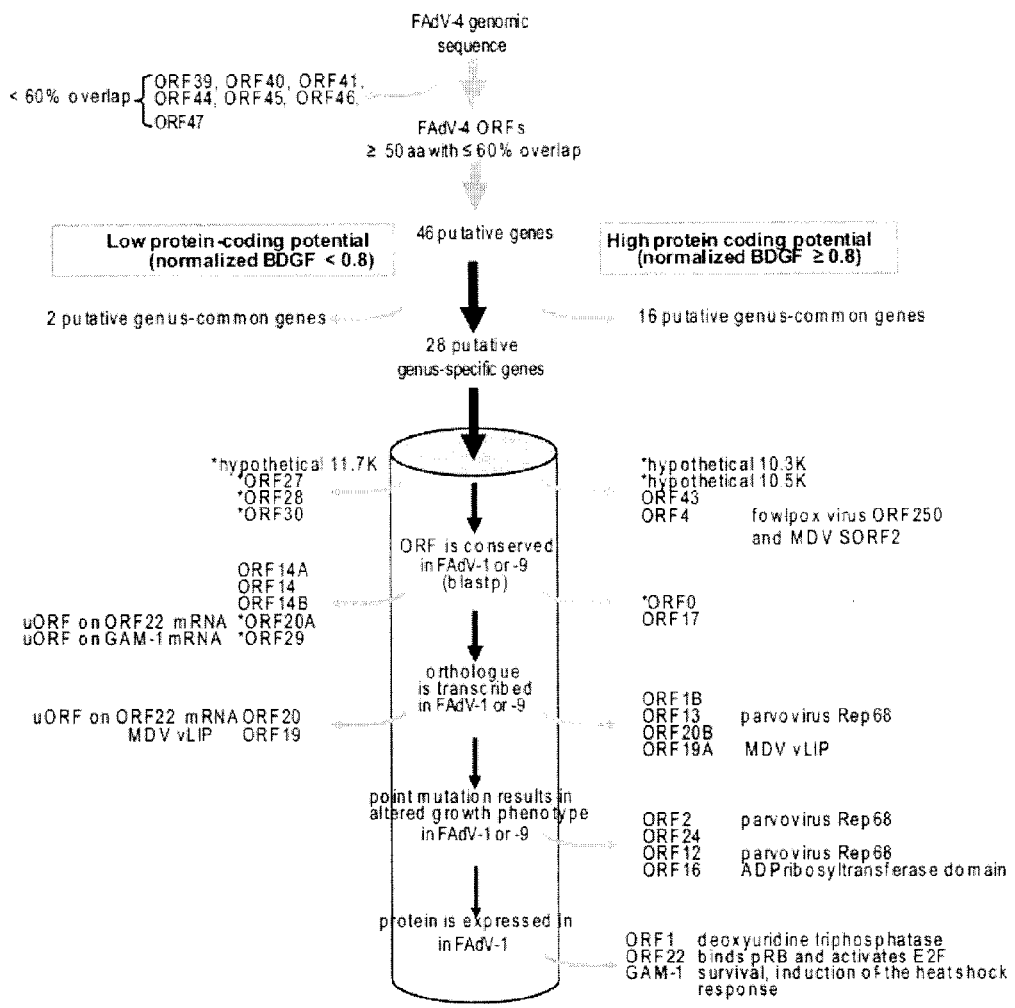

FIG. 6 is a flowchart of the analysis of the non-pathogenic FAdV-4 genomic sequence.

Figure 7:
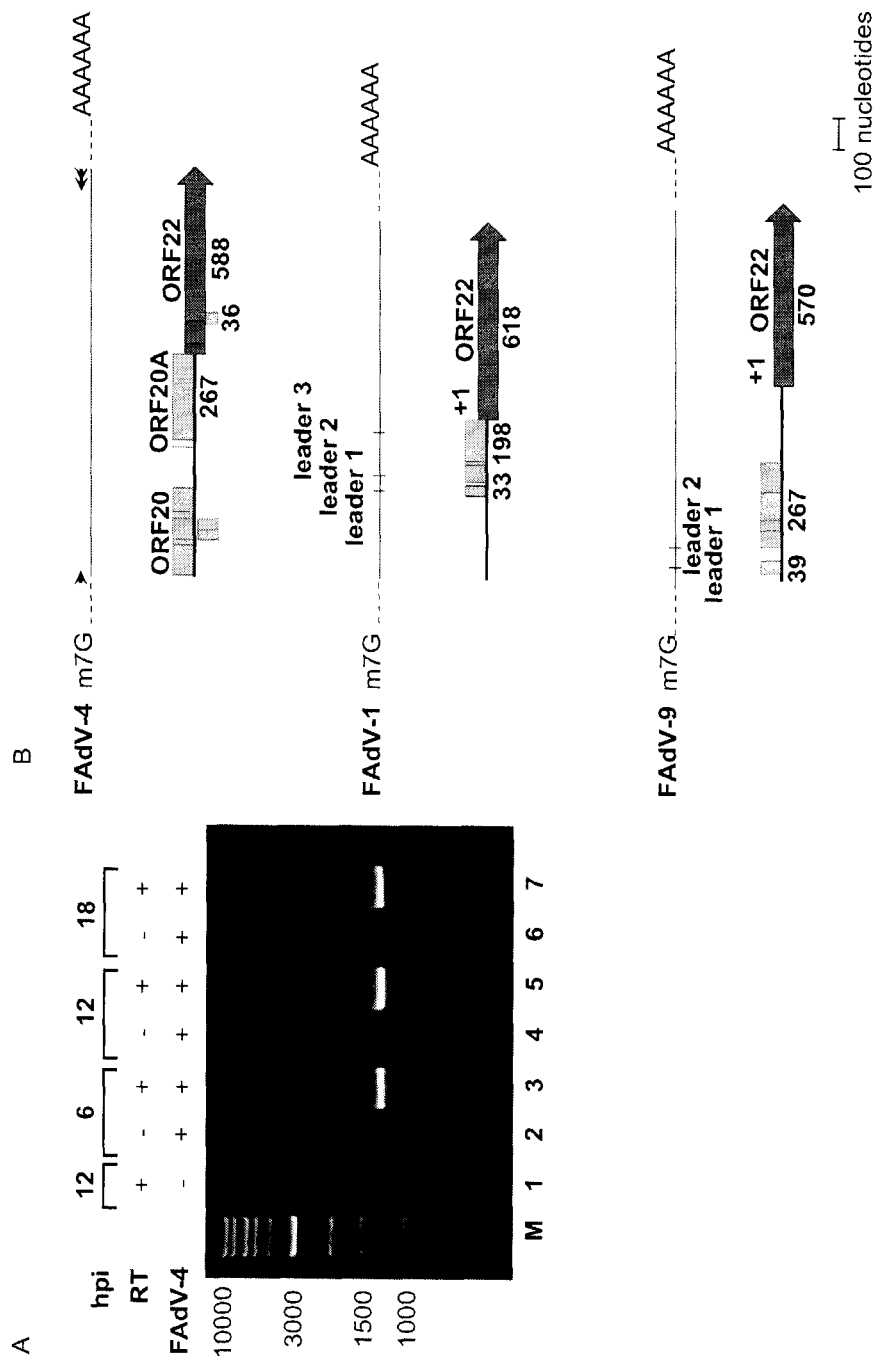

FIGS. 7A and B represent the uORFs in the 5'-UTR of the ORF22 mRNAs as detected by RT-PCR analysis of FAdV-4-infected CH-SAH cells. FIG. 7A shows the RT-PCR analysis of ORF22 using a forward primer derived from the ORF22 5'-UTR and a reverse primer derived from the ORF22 coding region. Total RNA was harvested from FAdV-4-infected or mock-infected CH-SAH cells at 6, 12, and 18 hpi, and 2 μg aliquots of RNA were treated with DNase and examined by PCR following RT (lanes 1, 3, 5, and 7), or without prior RT (lanes 2, 4, and 6). M indicates the 1-kb DNA ladder. FIG. 7B depicts the experimentally determined uAUG and uORF arrangements in the ORF22 transcripts are shown to-scale. The main ORF, ORF22, is designated by a dark grey arrow, whereas, the uORFs are indicated with medium grey boxes and the start codons with vertical lines. The primers used for the FAdV-4 RT-PCR are denoted with small black arrows. The number shown below each ORF represents the length in nucleotides. The scale is shown.

FIG. 8 shows the list of primer sequences used to detect the ORFs in FIGS. 7A and 7B.

FIG. 9 shows the viral genome copy numbers in different tissues of chickens (bursa, cecal tonsils and liver) infected either orally or intramuscularly with a strain of FAdV-4 ON1.

Figure 10:
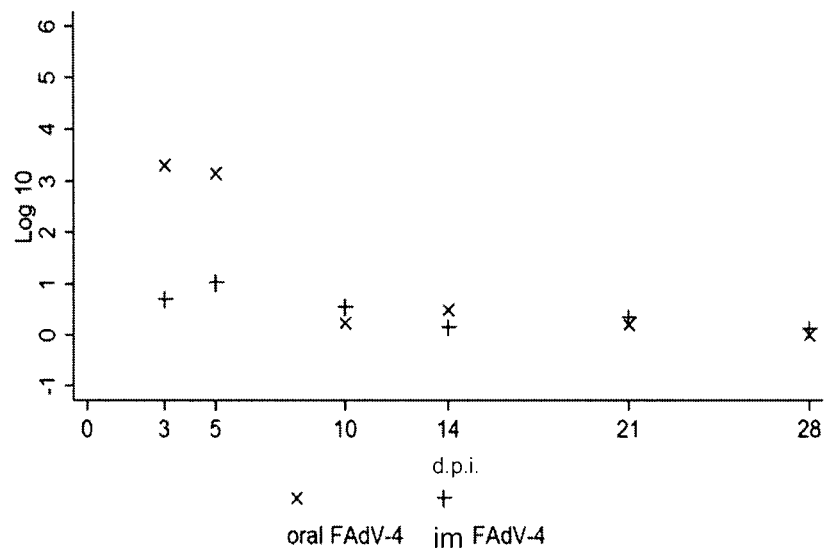

FIG. 10 shows virus titres in the feces of chickens inoculated orally or intramuscularly with a strain of FAdV-4 ON1.

Figure 11:
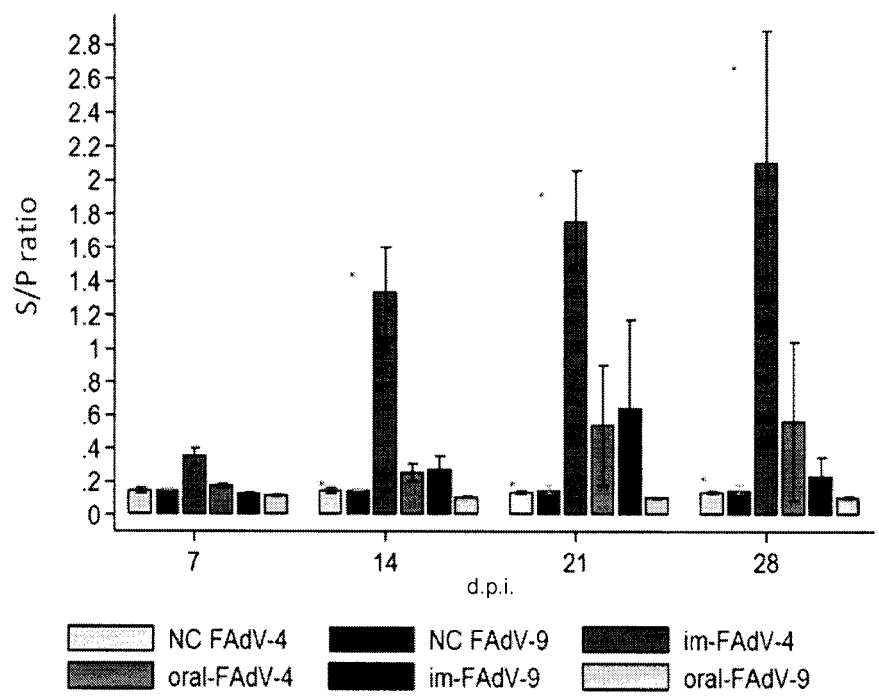

FIG. 11 shows the antibody response to viral proteins in chickens inoculated with FAdV-4 ON1 orally, intramuscularly, and mock infected.

DETAILED DESCRIPTION OF THE INVENTION

While developing the present invention, it was unexpectedly found a novel high level replication fowl adenovirus isolate, which is capable of reaching a viral titer of at least 3 $\log_{10}$, 3 days after inoculation in chicken. Viral titer can be measured by determining plaque forming units per ml (pfu/ml) as outlined in Romanova et al. *Detection and quantitation of fowl adenovirus genome by a real-time PCR assay*. Journal of Virological Methods Vol. 159, Issue 1 Jul. 2009, pages 58-6. Optionally, viral titer can be measured by determining the viral genome copy numbers in 100 ng of tissue DNA as determined by real-time PCR which has been shown to correspond to viral titer as measured by pfu/ml.

In a preferred embodiment, the novel fowl adenovirus (FAdV) isolate is a non-pathogenic strain of FAdV serotype 4, identified as FAdV-4 ON1. In one embodiment, the fowl adenovirus described herein consists of, comprises or has sequence identity to the DNA sequence of SEQ ID NO: 2 (deposited with GenBank/EMBL/DDBJ under accession number GU188428). For the purposes of the present invention, FAdV-4 ON1 is a plaque purified virus from a 04-50388 isolate.

Given the fact that the novel fowl adenovirus has a high level of replication, reaching a viral titer of at least 3 $\log_{10}$ 3 days after inoculation, which makes it suitable for obtaining viral vectors, another aspect of the invention is a viral vector of a fowl adenovirus (FAdV) which has inserted an exogenous nucleotide sequence coding for at least one antigenic site of a disease of concern. In a preferred embodiment, the viral vector is a non-pathogenic strain of FAdV serotype 4, identified as FAdV-4 ON1, and it consists of, comprises or has sequence identity to the nucleotide sequence of SEQ ID NO: 2

In an embodiment of the invention, the exogenous nucleotide sequence is selected from antigenic site sequences against influenza, infectious laryngotracheitis, infectious bronchitis, bursa of Fabricius' infection (Gumboro), hepatitis, viral rhinotracheitis, infectious coryza, *Mycoplasma hyopneumonieae*, pasteurellosis, Porcine Respiratory and Reproductive Syndrome (PRRS), circovirus, bordetellosis, parainfluenza, or any other antigen which size allows its insertion into the corresponding viral vector.

The viral vector of the present invention can be prepared by a PCR amplification of the nucleotide sequence of interest, by identifying the antigenic sites from an isolation of the origin-pathogen, to be further inserted, amplified in the viral vector. The insertion is made using standard molecular biology techniques, such as restriction enzymes and DNA ligases, amongst others. The infectious clone thus produced is introduced into a suitable cell line for the production of the recombinant virus. For example, the development of FAdV-4 ON1 as a vector may proceed by the creation of an infectious clone of FAdV-4 ON1, a plasmid construct containing the entire genomic sequence of FAdV-4 ON1 in a plasmid backbone conferring replication in bacteria under ampicillin selection. The construct may also contain unique restriction sites that will allow the vector to be linearized prior to transfection. In one embodiment, the methodologies required for the construction of the FAdV-4 ON1 infectious clone are the same as those used for the construction of the FAdV-9 infectious clone (FAdmid) (Ojkic, D. & Nagy, E. (2001)). The long repeat region is dispensable for fowl adenovirus replication in vitro. Virology 283, 197-206). This procedure utilizes homologous recombination between the viral genomic DNA and the linearized plasmid containing both ends of the genome flanking a backbone vector (pWE-Amp with PacI sites introduced). Next, a foreign gene of interest with a promoter to drive its expression is inserted in suitable genomic regions of the infectious clone that are dispensable or non-essential (Corredor and Nagy, 2010a and 2010b), and introduced into a suitable cell line.

The viral vector of the present invention can be used, for example, for the preparation and administration of immunogenic compositions comprising at least the viral vector obtained from the fowl adenovirus of the present invention with an exogenous nucleotide sequence coding for at least one antigenic site of a disease of concern inserted therein.

In one embodiment, the fowl adenovirus described herein comprises a nucleotide sequence with sequence identity to SEQ ID NO: 2. In one embodiment, the fowl adenovirus described herein comprises or consists of a nucleotide sequence with at least 80%, 85%, 90%, 95%, 96%, 97%, 98%, 99%, or 100% sequence identity to SEQ ID NO: 2.

Sequence identity is typically assessed by the BLAST version 2.1 program advanced search (standard default parameters; Altschul, S. F., Gish, W., Miller, W., Myers, E. W. &

Lipman, D. J. (1990) "Basic local alignment search tool." J. Mol. Biol. 215:403_410). BLAST is a series of programs that are available online through the U.S. National Center for Biotechnology Information (National Library of Medicine Building 38A Bethesda, Md. 20894) The advanced Blast search is set to default parameters. References for the Blast Programs include: Altschul, S. F., Gish, W., Miller, W., Myers, E. W. & Lipman, D. J. (1990) "Basic local alignment search tool." J. Mol. Biol. 215:403-410; Gish, W. & States, D. J. (1993) "Identification of protein coding regions by database similarity search." Nature Genet. 3:266-272; Madden, T. L., Tatusov, R. L. & Zhang, J. (1996) "Applications of network BLAST server" Meth. Enzymol. 266:131-141; Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402); Zhang, J. & Madden, T. L. (1997) "PowerBLAST: A new network BLAST application for interactive or automated sequence analysis and annotation." Genome Res. 7:649-656).

In embodiment, there is provided a viral vector obtained from the fowl adenovirus as described herein. As used herein, "viral vector" refers to a recombinant adenovirus that is capable of delivering an exogenous nucleotide sequence into a host cell. For example, in one embodiment, the viral vector comprises restriction sites that are suitable for inserting an exogenous nucleotide sequence into the vector. In one embodiment, one or more nucleotide sequences which are not required for the replication or transmission of fowl adenovirus serotype 4 described herein are deleted in the nucleotide sequence of the viral vector. As set out above, a person skilled in the art will appreciate obtaining a viral vector from the fowl adenovirus described herein.

In one embodiment, the viral vector comprises an exogenous nucleotide coding for a polypeptide of interest. In one embodiment, the polypeptide of interest is an antigen from a disease of concern. For example, in one embodiment, the viral vector comprises an exogenous nucleotide sequence coding for at least one antigenic site of a disease of concern. Exogenous nucleotide sequences coding for a polypeptide of interest can readily be obtained by methods known in the art such as by chemical synthesis, screening appropriate libraries or by recovering a gene sequence by polymerase chain reaction (PCR).

In one embodiment, the viral vector is adapted to express an exogenous nucleotide sequence in a host cell. For example, in one embodiment the viral vector comprises control sequences capable of affecting the expression of an exogenous nucleotide sequence in a host. For example, the viral vectors described herein may include one or more control sequences such as a transcriptional promoter, an enhancer, an optional operator sequence to control transcription, a sequence encoding suitable mRNA ribosomal binding sites, alternative splicing sites, translational sequences, or sequences which control the termination of transcription and translation.

In one embodiment, the viral vector comprises an exogenous nucleotide sequence is operably linked to a control sequence. In one embodiment, the viral vector comprises an insertion site adjacent to one or more control sequences such that when an exogenous nucleotide sequence is inserted into the vector, the exogenous nucleotide sequence is operably linked to the control sequences. As used herein, nucleotide sequences are "operably linked" when they are functionally related to each other. For example, a promoter is operably linked to a coding sequence if it controls the transcription of the sequence; a ribosome binding site is operably linked to a coding sequence if it is positioned so as to permit translation. Optionally, sequences that are operably linked are contiguous sequences in the viral vector.

In one embodiment, the viral vector described herein includes a sequence suitable for the biological selection of hosts containing the viral vector such as a positive or negative selection gene.

Other methods known in the art, such as recombinant technologies including but not limited to those disclose in disclosed by Sambrook et al (Sambrook J et al. 2000. Molecular Cloning: A Laboratory Manual (Third Edition), Cold Spring Harbor Laboratory Press), are also suitable for preparing the nucleotide sequences and viral vectors as described herein.

Another aspect of the present disclosure includes an immunogenic composition comprising a viral vector as described herein. In one embodiment, the immunogenic compositions can be prepared by known methods for the preparation of compositions for the administration to animals including, but not limited to, humans, livestock, poultry and/or fish. In one embodiment, an effective quantity of the viral vector described herein is combined in a mixture with a pharmaceutically acceptable carrier. Suitable carriers are described, for example in Remington's Pharmaceutical Sciences (Remington's Pharmaceutical Sciences, Mack Publishing Company, Easton, Pa., USA) or Handbook of Pharmaceutical Additives (compiled by Michael and Irene Ash, Gower Publishing Limited, Aldershot, England (1995). On this basis, the compositions include, albeit not exclusively, solutions of the viral vectors describes herein in association with one or more pharmaceutically acceptable carriers or diluents, and may be contained in buffered solutions with a suitable pH and/or be iso-osmotic with physiological fluids.

The novel fowl adenovirus of the present invention, and the vector obtained thereof, will be more clearly illustrated by means of the following description of specific examples, which are provided only with illustrative purposes, and not to limit the invention.

Example 1

Coding Potential and Transcript Analysis of FAdV-4

First-generation recombinant FAdV vectors have been successfully developed as veterinary vaccines; however, the limited understanding of the protein-coding regions and virus-host interactions restrict their progression into next-generation vectors.

Figure 1:
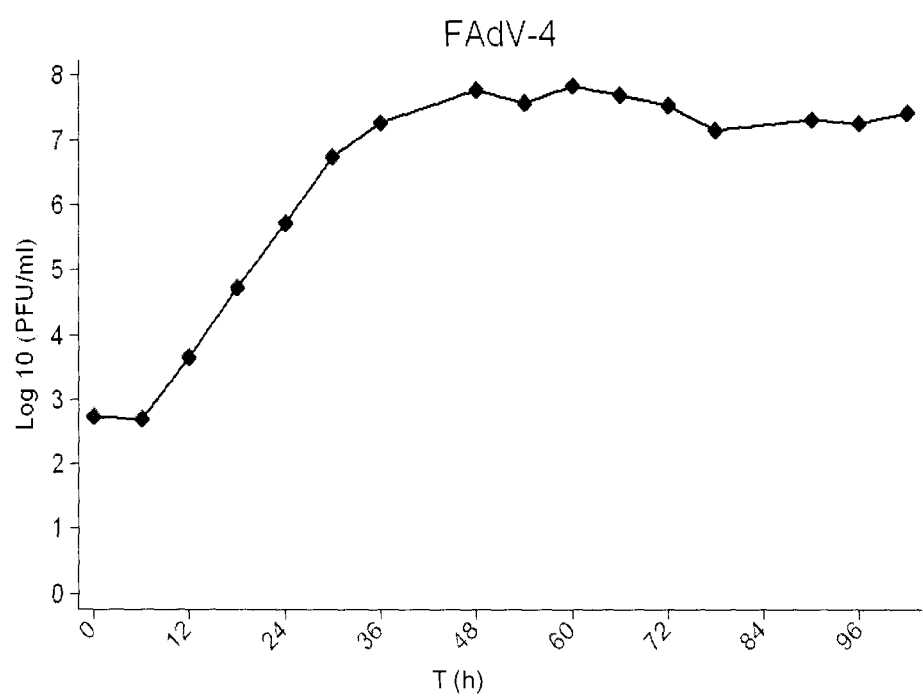
FIG. 1 shows a time course analysis of FAdV-4 replication in CH-SAH cells.

The FAdV-4 virus 04-50388 isolate was isolated from tissues collected from chickens of a Canadian broiler-breeder flock showing no clinical signs of IBH or HPS-IBH. Virus isolation was done at the Animal Health Laboratory (AHL), University of Guelph, Ontario, Canada. The virus was plaque purified and designated as FAdV-4 ON1. The virus was propagated in the chicken hepatoma cell line, CH-SAH, as described in Alexander, H., Huber, P., Cao, J., Krell, P. & Nagy, E. (1998). Growth characteristics of fowl adenovirus type 8 in a chicken hepatoma cell line. J Virol Methods 74, 9-14. As the time course analysis indicates (FIG. 1) FAdV-4 ON1 yields high titers in CH-SAH cells. The virus was concentrated and purified, and intact genomic DNA was extracted as previously described (Ojkic & Nagy 2001). The complete 45,667 base pair (bp) genome sequence of a non-pathogenic FAdV-4 ON1, was determined and 46 putative genes were identified. The FAdV-4 ON1 sequence (SEQ ID NO:2) was deposited with GenBank/EMBL/DDBJ under accession number GU188428.

Additional nucleotide sequences can be found in Genbank: FAdV-1 (AC_000014); FAdV-9 (AC_000013); HAdV-2 (AC_000007); HAdV-40 (NC_001454); TAdV-3 (HEV) (AF074946); DAdV-1 (EDS) (Y09598); FAdV-10 hexon (U26221); FAdV-4 PK-01 hexon (IBH/HPS) (EU931693); FaAdV hexon (AY683541).

a) Determination of the Complete Genome Sequence of a Non-Pathogenic Isolate of FAdV-4 ON1

Various methods were used in determining the genome sequence and properties of the FAdV-4 ON1.

For sequencing, a partial FAdV-4 DNA library was constructed by cloning BamHI-digested genome fragments into pBluescript SK(−) (Stratagene). A total of eight BamHI clones, ranging in size from 1905 bp to 8851 bp were sequenced by primer walking. PCR products generated by standard methodologies were purified with the QIAquick PCR Purification Kit (QIAGEN) and sequenced to fill in the gaps and to attain sufficient depth of coverage in the regions between the contigs. The terminal BamHI genome fragments were cloned and sequenced following alkaline removal (pH~10) of the terminal protein as previously described (Sira, S., Abouhaidar, M. G., Liu, Y. C. & Campbell, J. B. (1987). Multiple reiteration of a 40-bp nucleotide-sequence in the inverted terminal repeat of the genome of a canine adenovirus. Virology 159, 76-83). Automated DNA sequencer data was assembled into the full-length genome consensus contig using the classic assembler of SeqMan Pro (Lasergene v8.0; DNASTAR, Inc.).

Figure 2:
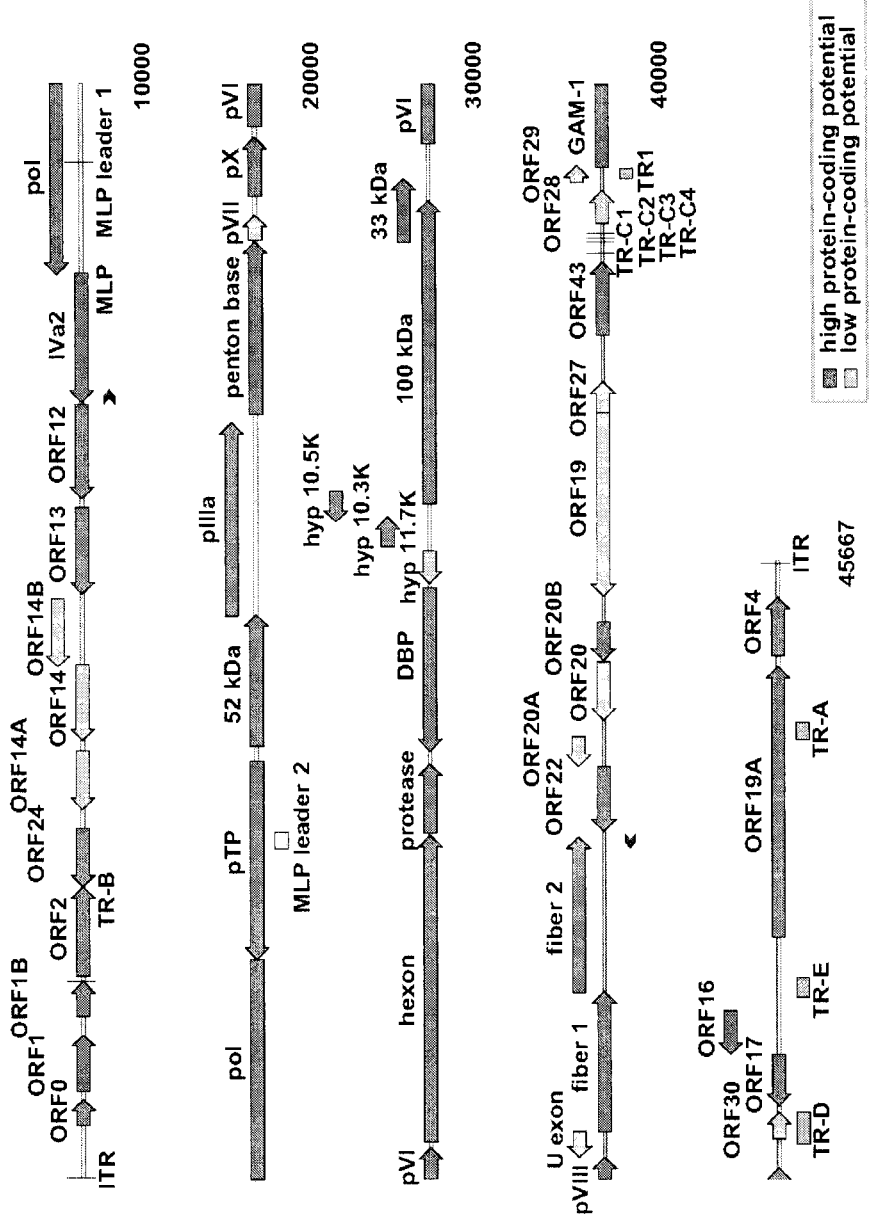
FIG. 2 depicts the genome organization of FAdV-4. The position and direction of transcription for the predicted ORFs is indicated by the arrows. Repeat regions are indicated with vertical dashes for small repeats and grey boxes for larger repeats, and repeat names are shown below the corresponding box. The major late promoter is represented by an arrow and the leader sequences are indicated. Chevrons depict the boundaries of the central genomic region. Each mark on the line below the map represents 1000 bp and all genome elements are depicted to-scale.

CH-SAH cells ($5.5 \times 10^6$) were infected with FAdV-4 (m.o.i. of 5) for one hour at room temperature. Total RNA was extracted with TRIzol (Invitrogen) according to the instructions of the manufacturer. Two μg of total RNA was treated with DNase I (Fermentas) and subjected to reverse transcription using Superscript III (Invitrogen) and gene-specific primers (FIG. 8). RT-PCR products were cloned into the pGEM-T Easy vector (Promega) and sequenced. To ensure residual viral genomic DNA was not amplified during the PCR, all the reactions included an RT negative control i) General Properties of the FAdV-4 ON1 Genome The genome of the non-pathogenic FAdV-4 ON1 is 45,667 bp in length with an overall base composition of 23.3% A, 27.7% C, 26.9% G, and 22.1% T and a G+C content of 54.6%. The FAdV-4 genome was larger than that of FAdV-9 (45,063 bp) (Ojkic & Nagy, 2000) and FAdV-1 (43,804 bp) (Chiocca et al., 1996), making it the largest AdV genome reported. Employing the inclusion criteria that an ORF must contain a methionine start codon, correspond in size to a peptide ≥50 amino acids, and not be overlapped by greater than 60% of its length by a larger ORF, a total of 46 potentially protein-coding ORFs distributed on both strands (57% on the sense strand and 43% on the antisense strand) were identified (FIG. 2). As with other avian adenoviruses, the FAdV-4 genome was organized into a central genomic region (nucleotides (nt) 7100 to 33,000) that consisted primarily of ORFs that were homologous to the genus-common genes and left and right terminal genomic regions (nt 1 to 7100 and nt 33,000 to 45,667, respectively) that consisted of ORFs homologous to the genus-specific genes. Of the 46 ORFs that were identified in the FAdV-4 genome, 18 represented genus-common genes and 28 represented genus-specific genes. The annotation of the predicted protein-coding regions is listed in Table 1.

The protein-coding potential of the predicted ORFs was evaluated using the Bio-Dictionary-based Gene Finder (BDGF) (Shibuya, T. & Rigoutsos, I. (2002). Dictionary-driven prokaryotic gene finding. Nucleic Acids Res 30, 2710-2725). The BDGF scores were normalized as previously reported (Murphy, E., Rigoutsos, I., Shibuya, T. & Shenk, T. E. (2003). Reevaluation of human cytomegalovirus coding potential. Proc Natl Acad Sci USA 100, 13585-13590). For each ORF, a BDGF score threshold of 0.8 was used to differentiate between predicted coding and non-coding ORFs. Orthologous proteins were identified by searching FAdV-4 ORFs against the non-redundant NCBI protein database using BLASTP (Altschul, S. F., Madden, T. L., Schäffer, A. A., Zhang, J., Zhang, Z., Miller, W. & Lipman, D. J. (1997). Gapped BLAST and PSI-BLAST: a new generation of protein database search programs. Nucleic Acids Res 25, 3389-3402.). A Kozak motif was reported for an ORF if it contained an AUG and matched at least three out of six nucleotides at positions, −1, −2, −3, −4, −5, and +4, in the Kozak consensus sequence, "CCA/GCCATG(G)" (Kozak, M. (1984). Compilation and analysis of sequences upstream from the translational start site in eukaryotic mRNAs. Nucleic Acids Res 12, 857-872.). Repeat regions within the genome were identified using the Tandem Repeats Finder version 4.04 (Benson, G. (1999). Tandem repeats finder: a program to analyze DNA sequences. Nucleic Acids Res 27, 573-580.). Codon usage was determined with DAMBE (Xia, X. & Xie, Z. (2001). DAMBE: software package for data analysis in molecular biology and evolution. J Hered 92, 371-373.). Multiple global pairwise alignments were done with mVISTA LAGAN (Brudno, M., Do, C. B., Cooper, G. M., Kim, M. F., Davydov, E., Program, N. C. S., Green, E. D., Sidow, A. & Batzoglou, S. (2003). LAGAN and Multi-LAGAN: efficient tools for large-scale multiple alignment of genomic DNA. Genome Res 13, 721-731.). Multiple sequence alignments were performed using ClustalX 2.0 (Larkin et al., 2007). The secondary structure of the fiber 1 and fiber 2 proteins was predicted with the Jpred 3 web server (Cuff, J. A., Clamp, M. E., Siddiqui, A. S., Finlay, M. & Barton, G. J. (1998). JPred: a consensus secondary structure prediction server. Bioinformatics 14, 892-893.). The bootstrap neighbor-joining tree was generated using MEGA 4.0.2 (Tamura et al., 2007).

TABLE 1

The protein-coding potential analysis of FAdV-4 ON1 ORFs.

| FAdV-4 ORF | ORF Position ATG | ORF Position Stop | Strand | Length (amino acids) | Kozak-AUG | BDGF Score (normalized) | Orthologues FAdV-1 mVista lagan | Orthologues FAdV-1 blastp | Orthologues FAdV-1 Transcription | Orthologues FAdV-1 Expression | Orthologues FAdV-9 mVista lagan | Orthologues FAdV-9 blastp | Orthologues FAdV-9 Transcript | Orthologues FAdV-9 Expression | non AdV blastp | Σ abs codon freq (chicken ORF) | protein superfamily, function of homologue, putative function |
|---|---|---|---|---|---|---|---|---|---|---|---|---|---|---|---|---|---|
| ORF0 | 478 | 717 | + | 79 | - | 11.1 | + | + | NR | NR | + | + | NR | NR |  | 738 | uORF on ORF1 mRNA (FAdV-1, -9) |
| ORF1 | 790 | 1314 | + | 174 | + | 2.3 | + | + | + | + | + | + | + | NR | + | 601 | dUTPase superfamily |
| ORF1B | 1485 | 1808 | + | 107 | - | 12.8 | + | + | + | + | + | + | + | NR |  | 845 |  |
| ORF2 | 1850 | 2665 | + | 271 | - | 1.3 | + | - | + | + | + | + | + | NR | + | 519 | Parvo_NS1 superfamily |
| ORF24 | 3203 | 2667 | - | 178 | - | 0.8 | - | + | NR | + | + | + | NR | NR | + | 669 | related to ORF14 |
| ORF14A | 3903 | 3373 | - | 176 | - | 0.2 | - | + | NR | + | + | + | NR | NR |  | 578 | related to ORF24 |
| ORF14 | 4683 | 3997 | - | 228 | - | 0.7 | - | + | NR | - | + | + | + | NR | + | 622 | " |
| ORF14B | 5296 | 4667 | - | 209 | + | 0.3 | - | + | NR | + | + | + | + | NR | + | 674 | " |
| ORF13 | 6130 | 5330 | - | 266 | + | 1.8 | + | + | + | + | + | + | + | NR | + | 549 | Parvo_NS1 superfamily |
| ORF12 | 7076 | 6207 | - | 289 | - | 2.2 | + | + | + | + | + | + | + | NR | + | 554 | Parvo_NS1 superfamily |
| IVa2 (SEQ ID NO: 13) | 8274 | 7090 | - | 394 | - | 3.3 | + | + | + | NR | + | + | + | NR |  | 500 |  |
| DNA polymerase (SEQ ID NO: 14) | 12016 | 8258 | - | 1252 | + | 4.7 | + | + | + | + | + | + | + | NR |  | 535 |  |
| pTP (SEQ ID NO: 15) | 13829 | 12021 | - | 602 | + | 5.3 | + | + | + | + | + | + | + | NR |  | 664 |  |
| 52 kDa (SEQ ID NO: 16) | 13959 | 15158 | + | 399 | - | 2.6 | + | + | + | + | + | + | + | NR |  | 664 |  |
| pIIIa (SEQ ID NO: 17) | 15145 | 16917 | + | 590 | - | 4.6 | + | + | + | + | + | + | + | NR |  | 552 |  |

TABLE 1-continued

| Name | | | | | | | | | | | | | | | | | | |
|---|---|---|---|---|---|---|---|---|---|---|---|---|---|---|---|---|---|---|
| penton base (SEQ ID NO: 18) | 16989 | 18566 | + | 525 | - | 3.0ᵇ | + | + | + | + | + | NR | + | + | + | + | + | 573 |
| pVII (SEQ ID NO: 19) | 18575 | 18808 | + | 77 | - | - |  |  |  |  |  | NR |  |  |  |  | + | 1144 |
| pX (SEQ ID NO: 20) | 18980 | 19519 | + | 179 | + | 11.1 | + | + | + | + | + | NR | + | + | + | + | + | 826 |
| pVI (SEQ ID NO: 21) | 19611 | 20294 | + | 227 | + | 11.5 | + | + | + | + | + | NR | + | + | + | + | + | 635 |
| Hexon (SEQ ID NO: 22) | 20340 | 23153 | + | 937 | + | 0.8 | + | + | + | + | + | NR | + | + | + | + | + | 661 |
| Protease (SEQ ID NO: 23) | 23171 | 23800 | + | 209 | + | 1.8 | + | + | + | + | + | NR | + | + | + | + | + | 580 |
| DBP (SEQ ID NO: 24) | 25402 | 23921 | - | 493 | + | 2.3ᵇ | + | + | + | + | + | NR | + | + | + | + | + | 560 |
| Hypothetical 11.7 kDa (SEQ ID NO: 25) | 25743 | 25441 | - | 100 | + | 0.6 | - | - | - | - | + | NR | - | - | - | - | - | 991 |
| Hypothetical 10.3 kDa (SEQ ID NO: 26) | 25775 | 26050 | + | 91 | - | 17.1 | - | - | - | - | - | - | - | - | - | - | - | 717 |
| Hypothetical 10.5 kDa (SEQ ID NO: 27) | 26291 | 26007 | - | 94 | - | 16.1 | - | - | - | - | - | - | - | + | - | - | - | 990 |
| 100 kDa (SEQ ID NO: 28) | 26178 | 28940 | + | 920 | + | 2.6 | - | + | + | + | + | NR | - | + | + | + | + | 496 |
| 33 kDa (SEQ ID NO: 29) | 28558 | 29145 | + | 195 | + | 2.3 | + | + | + | + | + | NR | - | + | + | + | + | 616 |

TABLE 1-continued

| Name | Start | End | Strand | aa | a | b | c | d | e | f | Size | Comment |
|---|---|---|---|---|---|---|---|---|---|---|---|---|
| pVIII (SEQ ID NO: 30) | 29460 | 30203 | + | 247 | | + | + | + | NR | | 685 | |
| U exon (SEQ ID NO: 31) | 30436 | 30200 | - | 78 | 0.2 | + | + | NR | NR | NR | 772 | |
| fiber-1 (SEQ ID NO: 32) | 30435 | 31733 | + | 432 | 2.5 | + | + | + | + | | 631 | |
| fiber-2 (SEQ ID NO: 33) | 31717 | 33141 | + | 474 | 3.3 | + | + | + | NR | | 609 | |
| ORF22 | 33781 | 33194 | - | 195 | 11.7 | + | + | + | + | NR | 576 | binds pRB, activates E2F (FAdV-1) |
| ORF20A | 34050 | 33784 | - | 88 | 0 | * | + | NR | NR | NR | 693 | uORF on ORF22 mRNA |
| ORF20 | 34737 | 34201 | - | 178 | 0.4 | + | + | + | + | NR | 644 | uORF on ORF22 mRNA |
| ORF20B | 35087 | 34746 | - | 113 | 1.3 | + | + | + | NR | NR | 638 | N-terminus of ORF20 (FAdV-1 and -9) |
| ORF19 | 37012 | 35330 | - | 560 | 0.4$^d$ | + | + | + | + | NR | 444 | Lipase superfamily |
| ORF27 | 37011 | 37292 | + | 93 | | | + | | | | 796 | |
| ORF43 | 37716 | 38381 | + | 221 | 8.0$^e$ | + | + | + | | | 574 | |
| ORF28 | 38737 | 39030 | + | 97 | 0 | + | + | + | | | 744 | |
| ORF29 | 39105 | 39263 | + | 52 | 0.1 | + | + | + | + | NR | 1233 | putative GAM-1 promoter |
| GAM-1 | 39245 | 40060 | + | 271 | 2.9 | + | + | + | + | NR | 470 | uORF on GAM-1 mRNA survival, heat shock response (FAdV-1) |
| ORF30 | 40377 | 40616 | + | 79 | 0.7 | | | | | | 845 | |
| ORF17 | 41156 | 40680 | - | 158 | 0.9 | + | + | NR | NR | NR | 551 | |
| ORF16 | 41556 | 41149 | - | 135 | 1.6 | + | + | + | + | | 755 | |
| ORF19A | 42216 | 44678 | + | 820 | 1.3 | + | + | + | + | NR | 475 | Lipase superfamily |
| ORF4 | 44772 | 45308 | + | 178 | 1.8 | + | + | + | + | | 612 | US22 superfamily |

$^a$17160-18566;
$^b$23921-25243;
$^c$26607 28940;
$^d$35330-36400;
$^e$38124-38381;
$^f$41149-41541. Codon.
* = FAdV-1 and FAdV-9 ORF20A do not begin with a start The protein-coding potential for each ORF as listed in Table 1 is indicated by the background colour in the leftmost column with dark and light grey representing high and low protein-coding potential, respectively. In all other columns, dark grey fields indicate characteristics that suggest an ORF is protein-coding and light grey fields designate characteristics that suggest an ORF is noncoding. Normalized BDGF scores are listed for each ORF unless the score was ≥0 or the ORF was excluded by the BDGF algorithm (denoted with a dash). Instances where BDGF designated a start codon other than that defining the largest potential ORF are indicated by a superscript letter. The occurrence of an orthologous ORF in FAdV-1 and/or FAdV-9 is indicated as positive (+) for >50% nt sequence conservation shown with mVISTA LAGAN and indicated as positive (+) for a statistically significant BLASTP, with E value >10-4 left uncoloured. Transcription of an orthologous ORF is indicated as positive (+) if experimental detection of mRNA expression has been reported (Cao, J. X., Krell, P. J. & Nagy, E. (1998). Sequence and transcriptional analysis of terminal regions of the fowl adenovirus type 8 genome. J Gen Virol 79 (Pt 10), 2507-2516; Ojkic, D., Krell, P. J. & Nagy, E. (2002). Unique features of fowl adenovirus 9 gene transcription. Virology 302, 274-285; Payet, V., Arnauld, C., Picault, J. P., Jestin, A. & Langlois, P. (1998). Transcriptional organization of the avian adenovirus CELO. J Virol 72, 9278-9285). Protein expression of the orthologous ORFs is indicated as positive (+) if reports have demonstrated protein expression or that a point mutation or deletion has resulted in an altered phenotype (Francois, A., Eterradossi, N., Delmas, B., Payet, V. & Langlois, P. (2001). Construction of avian adenovirus CELO recombinants in cosmids. J Virol 75, 5288-5301; Lehrmann, H. & Cotten, M. (1999). Characterization of CELO virus proteins that modulate the pRb/E2F pathway. J Virol 73, 6517-6525.). The abbreviation NR indicates that no reports were identified.

b) Identification of the Most Probable Protein-Coding and Noncoding Open Reading Frames (ORFs) as Well as the ORFs that Contribute to Upstream ORFs (uORFs) as a Basis for Functional Studies.

i) Phylogeny

Figure 3:
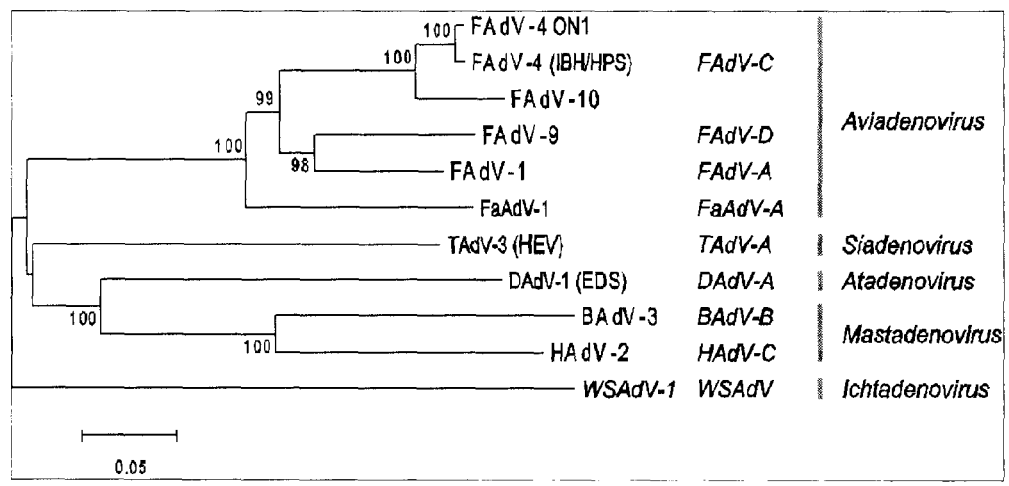
FIG. 3 shows the phylogenetic analysis of FAdV-4 based on the predicted amino acid sequences of the hexon. The phylogenetic tree was constructed using the neighbor-joining, p-distance method in MEGA version 4.0 (Tamura, K., Dudley, J., Nei, M. & Kumar, S. (2007). MEGA4: Molecular Evolutionary Genetics Analysis (MEGA) software version 4.0. Mol Biol Evol 24, 1596-1599). The Gonnet protein weight matrix was used to generate the ClustalW alignments. Percentage bootstrap confidence levels as determined for 1000 pseudoreplicates are shown at the relevant internal nodes. Genetic distance in substitutions per nucleotide is indicated by the scale in the lower left of each panel. White sturgeon adenovirus (WSAdV-1) was included as an outgroup. FaAdV=Falcon adenovirus; EDS=Egg drop syndrome virus; HEV=hemorrhagic enteritis virus; IBH/HPS=IBH/hydropericardium syndrome-associated strain from India.

Phylogenetic analysis of the predicted amino acid sequences of the hexon gene was performed using the neighbour-joining method of Molecular Evolutionary Genetics Analysis (MEGA) 4.0 (Tamura et al., 2007). The FAdV-4 ON1 isolate clustered as expected with species FAdV-C, close to an IBH/HPS-associated strain of FAdV-4, supported by high bootstrap values at all nodes (≥98%) (FIG. 3).

Figure 4:
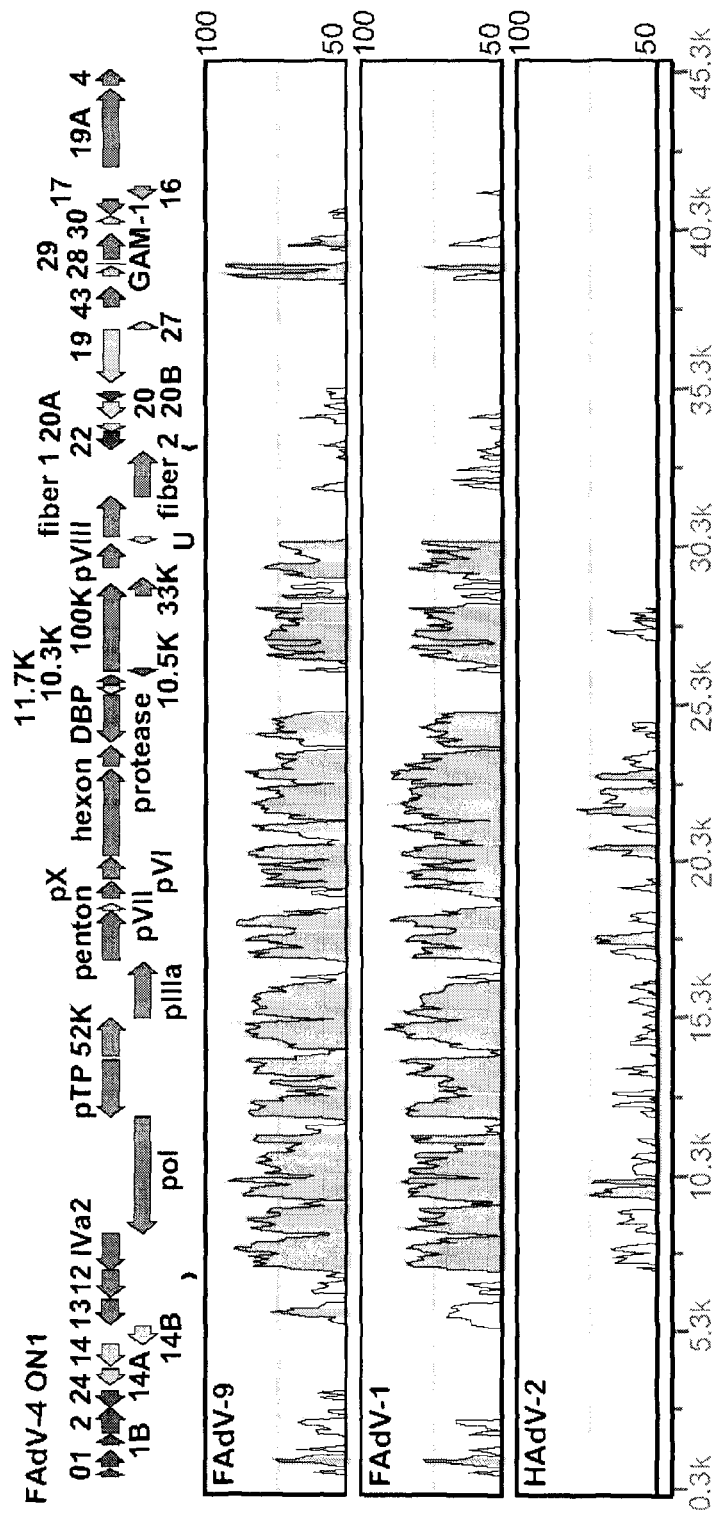
FIG. 4 shows the global pairwise sequence alignment of FAdV-4 with FAdV-9, FAdV-1, and HAdV-2, using mVISTA LAGAN. The height of the plot on the y-axis indicates the percentage nucleotide identity of selected AdV genomes with the FAdV-4 genome. The x-axis indicates the nucleotide position on the FAdV-4 genome. Regions of high sequence conservation are coloured. The FAdV-4 genome is shown to-scale above the alignment. ORFs are depicted as arrows with dark grey and light grey representing high and low protein-coding potential, respectively. Chevrons depict the boundaries of the central genomic region.

A global pairwise alignment of the genome sequence of FAdV-4 with those of FAdV-1, FAdV-9, and human adenovirus 2 (HAdV-2) was carried out using mVISTA Limited Area Global Alignment of Nucleotides (LAGAN) software (Brudno et al., 2003) (FIG. 4). The central region of the FAdV-4 genome displayed high sequence conservation (FIG. 4, shaded regions) with FAdV-1 and FAdV-9 and moderate sequence conservation with HAdV-2 (FIG. 4, white regions). The terminal regions of the FAdV-4 genome showed low sequence conservation with FAdV-1 and FAdV-9 and no sequence conservation with HAdV-2. The specific ORFs that showed regions with greater than 50% sequence conservation with FAdV-1 and/or FAdV-9 are also noted in Table 1.

ii) Protein-Coding Potential Analysis

Figure 5:
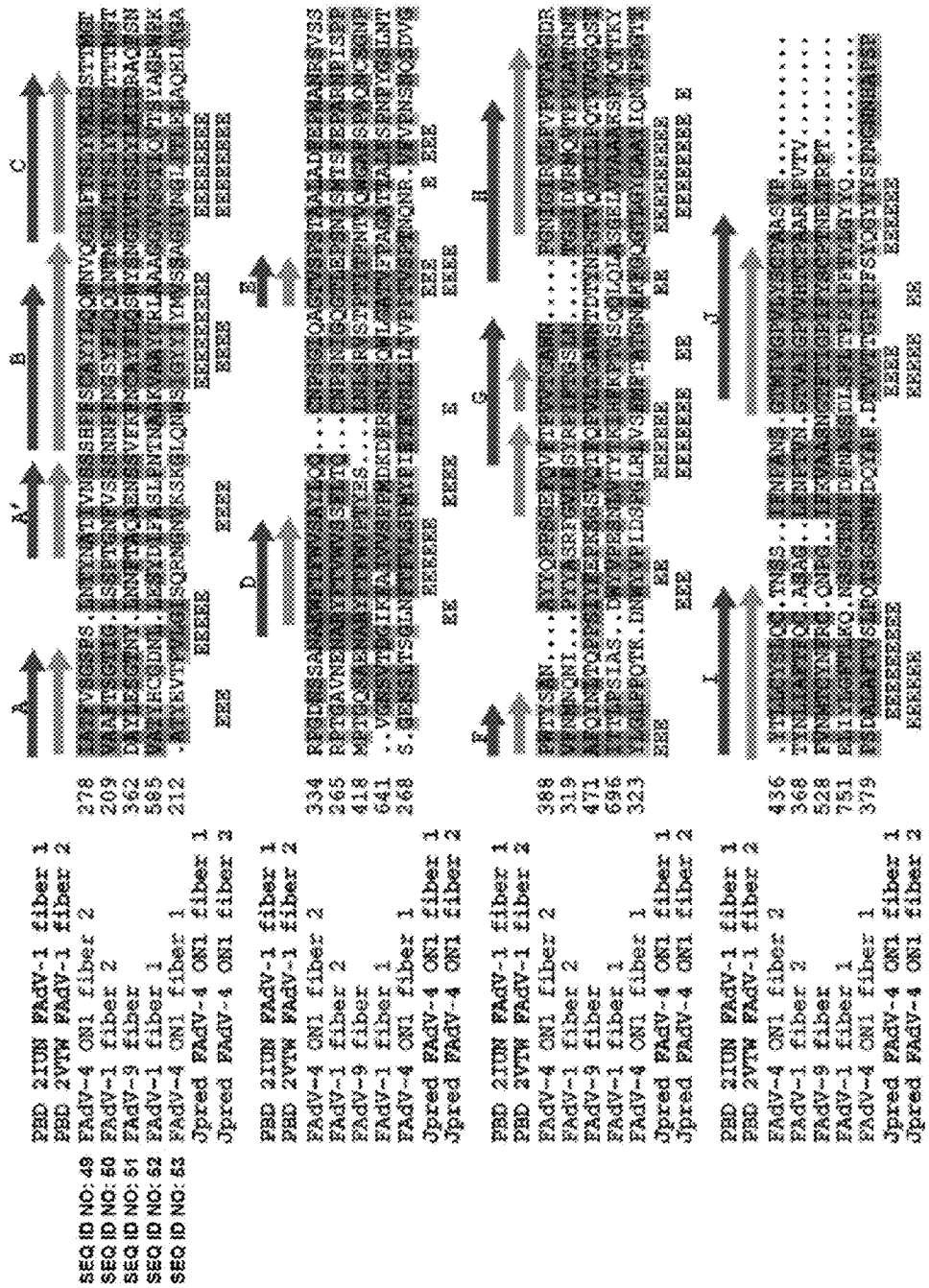
FIG. 5 shows the multiple alignment of the fiber head domains of selected FAdVs and structural analysis of FAdV-4 fiber 2. The sequence alignment of the selected FAdV fiber head domains was performed with ClustalX (Larkin, M. A., Blackshields, G., Brown, N. P., Chenna, R., McGettigan, P. A., McWilliam, H., Valentin, F., Wallace, I. M., Wilm, A. & other authors. (2007). Clustal W and Clustal X version 2.0.

Assessment of the protein-coding potential of the 46 identified ORFs was carried out by processing the genomic DNA sequence with the BD-based Gene Identification tool (IBM Inc.), an application of the Bio-Dictionary-based Gene Finder (BDGF) algorithm (Shibuya & Rigoutsos, 2002) for which there is precedent for eukaryotic viral gene prediction (Murphy et al., 2003; Rigoutsos, I., Novotny, J., Huynh, T., Chin-Bow, S., Panda, L., Platt, D., Coleman, D. & Shenk, T. (2003). In silico pattern-based analysis of the human cytomegalovirus genome. J Virol 77, 4326-4344). A combined analysis that further took into account (i) the existence of orthologous ORFs in other FAdVs, (ii) experimental detection of orthologous transcripts (Cao et al., 1998; Ojkic et al., 2002; Payet et al., 1998), and (iii) explicitly demonstrated orthologous protein expression, or implied protein expression through a point mutation resulting in an altered viral growth phenotype in FAdV-1 (François et al., 2001; Lehrmann & Cotten, 1999) was used. Of the 21 ORFs located within the central genomic region, 18 were homologues of genus-common genes, and, with the exception of U exon and pVII, were assigned high protein-coding potential by BDGF (FIG. 2 and Table 1). Based on the known functions of the genus-common genes in the mastadenoviruses, these 18 ORFs can be expected to encode proteins that are indispensable (Berk, A. (2007). Adenoviridae: the viruses and their replication. In Fields virology, 5th ed, pp. 2355-2394. Edited by D. Knipe, P. Howley, D. Griffin, R. Lamb, M. Martin, B. Roizman & S. Straus. Philadelphia, Pa.: Lippincott Williams & Wilkins.; Davison, A. J., Benko, M. & Harrach, B. (2003a). Genetic content and evolution of adenoviruses. J Gen Virol 84, 2895.). The most notable features observed within the central genomic region were the two predicted fiber genes, fiber 1 and fiber 2, and the three hypothetical genes with predicted molecular masses of 11.7, 10.3, and 10.5 kDa, respectively (11.7K, 10.3K, and 10.5K) (FIG. 2). The two fiber genes were located adjacent to one another between U exon and ORF22. Jpred secondary structure prediction of the FAdV-4 fiber 1 and fiber 2 head domains showed a similar 6-strand arrangement to FAdV-1 fiber 1 and fiber 2, indicating that both fiber genes are likely to encode functional proteins (FIG. 5). Three hypothetical ORFs, nonhomologous to the genus-common genes, were located between DNA-binding protein (DBP) and 100K; 11.7K was assigned low protein-coding potential (LP-CP) and 10.3K and 10.5K were assigned high protein-coding potential (HP-CP) by BDGF (FIG. 2 and Table 1).

Of the 25 ORFs located within the left and right terminal genomic regions that were homologous to genus-specific genes, 15 and 10 ORFs were assigned high and low protein-coding potential, respectively (FIG. 2 and Table 1). Among the 15 ORFs assigned high protein-coding potential were ORF1, ORF22, and GAM-1 (SEQ ID NO:43), whose orthologs in FAdV-1 are the only FAdV genus-specific genes with functionally characterized proteins (Chiocca, S. (2007). Viral control of the SUMO pathway: Gam1, a model system. Biochem Soc Trans 35, 1419-1421; Glotzer, J. B., Saltik, M., Chiocca, S., Michou, A. I., Moseley, P. & Cotten, M. (2000). Activation of heat-shock response by an adenovirus is essential for virus replication. Nature 407, 207-211; Lehrmann & Cotten, 1999; Weiss, R. S., Lee, S. S., Prasad, B. V. V. & Javier, R. T. (1997). Human adenovirus early region 4 open reading frame 1 genes encode growth-transforming proteins that may be distantly related to dUTP pyrophosphatase enzymes. J Virol 71, 1857-1870); ORF2, ORF12, ORF13, ORF19A, and ORF4, which have cellular and/or viral homologues within the Parvoviridae, Herpesviridae, or Poxviridae families (Chiocca et al., 1996; Corredor et al., 2008; Corredor of al., 2006; Ojkic & Nagy, 2000; Washietl, S. & Eisenhaber, F. (2003). Reannotation of the CELO genome characterizes a set of previously unassigned open reading frames and points to novel modes of host interaction in avian adenoviruses. BMC Bioinformatics 4, 55); and ORF16, which shows conservation of a cellular ADP-ribosyltransferase domain (Corredor et al., 2006; Washietl & Eisenhaber, 2003) (Table 1). The six remaining genus-specific gene orthologues that were assigned high protein-coding potential in our analysis, namely, ORF0 (SEQ ID NO:3), ORF1B (SEQ ID NO:5), ORF24 (SEQ ID NO:7), ORF20B (SEQ ID NO:37), ORF43 (SEQ ID NO:40), and ORF17 (SEQ ID NO:45), were without identifiable functional domains or cellular or viral homologues (Table 1). Of the 15 ORFs assigned high protein-coding potential by BDGF, only three, ORF43, ORF19A (SEQ ID NO:47), and ORF4 (SEQ ID NO:48), were not conserved between FAdV-4 and FAdV-1 and/or FAdV-9 in the BLASTP and LAGAN analyses (Table 1 and FIG. 4), and all 15 ORFs were conserved between FAdV-4 CA, FAdV-10 C-26 (Corredor et al., 2008; Corredor et al., 2006), and FAdV-4 ON1. Ten of the ORFs had orthologues in FAdV-1 and/or FAdV-9 with reported mRNA expression, including ORF1 (SEQ ID NO:4), ORF1B (SEQ ID NO:5), ORF2 (SEQ ID NO:6), ORF13 (SEQ ID NO:11), ORF12 (SEQ ID NO:12), ORF22 (SEQ ID NO:34), ORF20B (SEQ ID NO:37), GAM-1 (SEQ ID NO:43), ORF16 (SEQ ID NO:46), and ORF19A (Table 1). Lastly, eight of the 15 ORFs had orthologues in FAdV-1 that either encode proteins or for which indirect evidence of protein expression had been shown through mutational analysis or deletion resulting in an altered phenotype, namely ORF1, ORF2, ORF24, ORF12, ORF22, GAM-1, ORF17, and ORF16 (Table 1). The 10 ORFs that were assigned low protein-coding potential consisted of ORF14A (SEQ ID NO:8), ORF14 (SEQ ID NO:9), ORF14B (SEQ ID NO:10), ORF20A (SEQ ID NO:35), ORF20 (SEQ ID NO:36), ORF19 (SEQ ID NO:38), ORF27 (SEQ ID NO:39), ORF28 (SEQ ID NO:41), ORF29 (SEQ ID NO:42), and ORF30 (SEQ ID NO:44). Of these, only ORF19 had an orthologue with a functional domain or cellular or viral homologue (Corredor et al., 2008; Washietl & Eisenhaber, 2003). Three of the 10 ORFs, ORF20A, ORF20, and ORF29, were highly conserved between FAdV-4 and FAdV-1 and/or FAdV-9 in the BLASTP and LAGAN analyses (Table 1 and FIG. 3), and four ORFs, ORF14A, ORF14, ORF14B, and ORF19, were highly conserved between FAdV-4 and FAdV-1 and/or FAdV-9 in the BLASTP analysis (Table 1). Only two of the ten ORFs, ORF20 and ORF19, had orthologues in FAdV-1 and/or FAdV-9 with reported mRNA expression, and only ORF14 had an orthologue for which there was indirect evidence of protein expression (Table 1). A flowchart of the analysis is depicted in FIG. 6.

The biological significance of the two fiber genes that were predicted to be protein-coding (Table 1 and FIG. 5) is unknown; however, both FAdV-1 and the enteric HAdV-F serotypes, HAdV-40 and -41, contain two fiber genes. In FAdV-1, fiber 1 (the long fiber) is dispensable for binding avian cells in vitro, but required for CAR-binding, and FAdV-1 fiber 2 (short fiber) is thought to bind a receptor that is present on avian and not mammalian cells (Tan, P. K., Michou, A. I, Bergelson, J. M. & Cotten, M. (2001). Defining CAR as a cellular receptor for the avian adenovirus CELO using a genetic analysis of the two viral fibre proteins. J Gen Virol 82, 1465-1472). In HAdV-41, the long fiber is known to bind CAR while the short fiber does not (Roelvink, P. W., Lizonova, A., Lee, J. G. M., Li, Y., Bergelson, J. M., Finberg, R. W., Brough, D. E., Kovesdi, I. & Wickham, T. J. (1998). The coxsackievirus-adenovirus receptor protein can function as a cellular attachment protein for adenovirus serotypes from subgroups A, C, D, E, and F. J Virol 72, 7909-7915), and it has been theorized that short fiber mediates altered tropism that results in the gastroenteritis associated with species HAdV-F viruses (Favier, A. L., Schoehn, G., Jaquinod, M., Harsi, C. & Chroboczek, J. (2002). Structural studies of human enteric adenovirus type 41. Virology 293, 75-85). We, therefore, speculate that the FAdV-4 fiber 2 (short fiber) might bind a receptor other than CAR and determine the tissue tropism of FAdV-4, perhaps leading to the unique clinical features associated with infection with virulent FAdV-4.

The protein-coding potential of FAdV-4 was evaluated and each of the putative genes was discriminated into one of two classes, representing either low or high protein-coding potential. Through RT-PCR analysis, it was determined that several ORFs that were assigned low protein-coding potential occurred as large uORFs, greater than 153 nt (50 aa) in length, ORF20A and ORF20 in the ORF22 mRNA (Table 1 and FIG. 7) and ORF29 in the GAM-1 mRNA (Table 1).

iii) uORFs in the 5'-UTR Region of FAdV-4 mRNAs

To explain the occurrence of several ORFs that were not predicted to have high protein-coding potential, but were highly conserved among FAdVs, a subset of the low coding potential ORFs that corresponded to a peptide <100 aa in length (ORF20A, ORF20, ORF27, ORF28, ORF29, ORF30) was considered to contribute to uORFs, defined by a start codon in the 5' UTR that is out-of-frame with the downstream coding sequence. Reverse transcription-PCR (RT-PCR) was carried out on RNA extracted from FAdV-4-infected cells with ORF22 gene-specific primers (see FIG. 7B, upper panel for primer locations and FIG. 8 for primer sequences). ORF22 mRNA was detected at 6, 12, and 18 hours post-infection (hpi) (FIG. 7A). Sequencing of the PCR product revealed that ORF20A and ORF20 both contributed to large uORFs in the ORF22 mRNA (FIG. 7B, upper panel). The ORF22 mRNA contained a long 5'-UTR, greater than 718 nts in length. The ORF20 uORF was >277 nt (91 aa) in length with several upstream start codons (uAUGs), and the ORF20A uORF, located immediately upstream (3 nts) of the ORF22 AUG, was 267 nt in length (91 aa) with no intervening uAUGs (FIG. 7B, upper panel). The ORF22 mRNA transcript sequences of FAdV-1 and FAdV-9 was reconstituted in silico, based on the experimentally determined splice donor and acceptor sites (Ojkic et al., 2002; Payet et al., 1998) and used GeneQuest (Lasergene v8.0; DNASTAR, Inc.) to examine the transcripts for the presence of uORFs. While splicing did not occur within the sequenced region of the FAdV-4 ORF22 5'-UTR, analysis of the FAdV-1 and FAdV-9 ORF22 5'-UTRs showed interspecies variation in splice donor and acceptor sites that directed the removal of different portions of ORF20 and ORF20A (FIG. 7B, lower panels). All three of the examined FAdV serotypes (FAdV-1, -4, -9) had a long ORF22 5'-UTR that contained a minimum of 4 uAUGs and at least one large uORFs. Additional RT-PCR analysis revealed that ORF29 was a uORF in the 5'-UTR of the FAdV-4 GAM-1 mRNA and that the TR-1 repeat region, nested entirely within ORF29, conferred with each repeat unit an additional uAUG to ORF29.

Codon usage analysis with DAMBE revealed that 11 of the 14 ORFs with the largest cumulative difference in codon usage from gallus gallus were ≤100 aa in length, eight of which were low coding potential ORFs, namely ORF29, pVII, hypothetical 11.7 kDa, ORF30, ORF27, U exon, ORF28, ORF20A (Table 1).

The conventional FAdV annotation criterion that defines the minimal ORF size as corresponding to 50 aa in length (Chiocca et al., 1996; Ojkic & Nagy, 2000) is sensible; however, it increases the likelihood that spurious ORFs are retained within genome annotations. It appears that BDGF discriminated between small ORFs of high (ORF0, 10.3K, and 10.5K) and low (pVII, 11.7K, U exon, ORF20A, ORF27, ORF28, ORF29, ORF30) protein-coding potential (Table 1). Sequence conservation among closely related species has proven to effectively identify protein-coding regions (Clamp, M., Fry, B., Kamal, M., Xie, X. H., Cuff, J., Lin, M. F., Kellis, M., Lindblad-Toh, K. & Lander, E. S. (2007). Distinguishing protein-coding and noncoding genes in the human genome. Proc Natl Acad Sci USA 104, 19428-19433; Davison, A. J., Dolan, A., Akter, P., Addison, C., Dargan, D. J., Alcendor, D. J., McGeoch, D. J. & Hayward, G. S. (2003b). The human cytomegalovirus genome revisited: comparison with the chimpanzee cytomegalovirus genome. J Gen Virol 84, 17-28), and the BDGF assignments of protein-coding potential generally correlated with sequence conservation among FAdV species and with reports in the literature supporting the conclusion of an orthologous ORF being protein-coding (Table 1 and FIG. 6).

A detailed list of uORFs in the FAdVs with their nucleotide coordinates is provided as Table 2.

TABLE 2

Unabridged list of ORFs in FAdVs

| | | | uORF | | | | | |
|---|---|---|---|---|---|---|---|---|
| | | | | Sequence overlap (in frame) with annotated ORF | | # of uAUGs within uORF and prior to | Position relative | | |
| Virus | Location | Size (aa) | Name | Overlap | sAUG of CDS | to CDS | CDS | CDS function |
| FAdV-1 | 519-596, 789-977 | 88 | ORF0 | 519-596 | 1 | overlap | ORF1 | functional dUTPase |
| | 4462-5385 | 309 | ORF12 | entire (bicistronic) | 6 | overlap | ORF13 | unknown (Rep homologue) |
| | 5088-5231 | 47 | — | — | 1 | upstream | ORF13 | " |
| | 5061-5072 | 3 | — | — | 1 | upstream | ORF13 | " |
| | 4980-4988 | 2 | — | — | 1 | upstream | ORF13 | " |
| | 4655-4729 | 24 | — | — | 1 | upstream | ORF13 | " |
| | 16727-16897 | 56 | pVII | 16727-16897 | 2 | upstream | pX (μ) | core |
| | 16894-16926 | 10 | — | — | 2 | upstream | pX (μ) | " |
| | 16910-17044 | 44 | — | — | 1 | overlap | pX (μ) | " |
| | 39291-39705, 24764-24780 | 143 | ORF16 | 39291-39705 (bicistronic) | 4 | upstream | DBP | DNA-binding protein during replication |
| | 39642-39650 | 2 | — | — | 1 | upstream | DBP | DNA-binding protein during replication |
| | 39609-39626 | 5 | — | — | 1 | upstream | DBP | DNA-binding protein during replication |
| | 39446-39466 | 6 | — | — | 1 | upstream | DBP | DNA-binding protein during replication |
| | 39374-39445 | 23 | — | — | 1 | upstream | DBP | DNA-binding protein during replication |
| | 39302-39313 | 3 | — | — | 1 | upstream | DBP | DNA-binding protein during replication |
| | 39291-39305, 24716-24780, 23455-23667, 23289-23340 | 114 | — | — | 2 | overlap | DBP | DNA-binding protein during replication |
| | 23198-23566 | 122 | — | — | 2 | upstream | 100K | ribosome shunting in HAdV-2 |
| | 23223-23327 | 34 | — | — | 1 | upstream | 100K | " |
| | 43059-43071, 33917-33936 | 10 | — | — | 1 | upstream | ORF22 | proliferation (binds pRB) |
| | 33887-33906, 33070-33204, 32431-32473 | 65 | ORF20 | 32892-33906 | 3 | upstream | ORF22 | " |
| | 33 uORFs on mRNA | | — | — | | | ORF19 | lipase that is predicted to be nonfunctional due to frameshift |
| FAdV-9 | 575-744 | 56 | ORF0 | 575-746 | 1 | upstream | ORF1 | unknown (dUTPase homologue) |
| | 17377-17388 | 3 | — | — | 1 | upstream | ORF13 | unknown (Rep homologue) |
| | 16276-16281, 11440-11454 | 6 | — | — | 1 | upstream | DNA Pol | frameshift in C-terminus |
| | 11244-11252 | 2 | — | — | 1 | upstream | DNA Pol | " |
| | 10951-11247 | 98 | — | — | 2 | upstream | DNA Pol | " |
| | 11019-11129 | 36 | — | — | 1 | upstream | DNA Pol | " |
| | 17377-17388 | 3 | — | — | 1 | upstream | pTP | protein priming during replication |
| | 36426-36443, 34040-34060 | 12 | — | — | 1 | upstream | ORF22 | proliferation (binds pRB) |
| | 33998-34018, 32741-32986 | 88 | — | — | 4 | upstream | ORF22 | " |
| | 40881-40997 | 38 | — | — | 2 | upstream | ORF11 | unknown (IgG-like) |
| | 40945-40992 | 15 | — | — | 2 | upstream | ORF11 | " |
| | 41008-41287, 41378-41385 | 95 | — | — | 1 | upstream | ORF11 | " |

Similar analysis of previously reported transcript sequences for the mastadenoviruses, HAdV-2 and bovine adenovirus 3 (BAdV-3) revealed uORFs in a number of early gene transcripts (Table 3). In both HAdV-2 and BAdV-3, the sole transcript detected encoding E1B-55K is partially overlapped by E1B-19K in a potential bicistronic mRNA (Broker, T. (1984). Animal Virus RNA Processing. In Processing of RNA, pp. 181-212. Edited by D. Apirion. Boca Raton, Fla.: CRC Press, Inc.; Reddy, P. S., Chen, Y., Idamakanti, N., Pyne, C., Babiuk, L. A. & Tikoo, S. K. (1999). Characterization of early region 1 and pIX of bovine adenovirus-3. Virology 253, 299-308; Zheng, B. J., Graham, F. L. & Prevec, L. (1999). Transcription units of E1a, E1b and pIX regions of bovine adenovirus type 3. J Gen Virol 80, 1735-1742).

TABLE 3 uORFs in HAdV-2, BAdV-3, FAdV-1, and FAdV-9 mRNAs

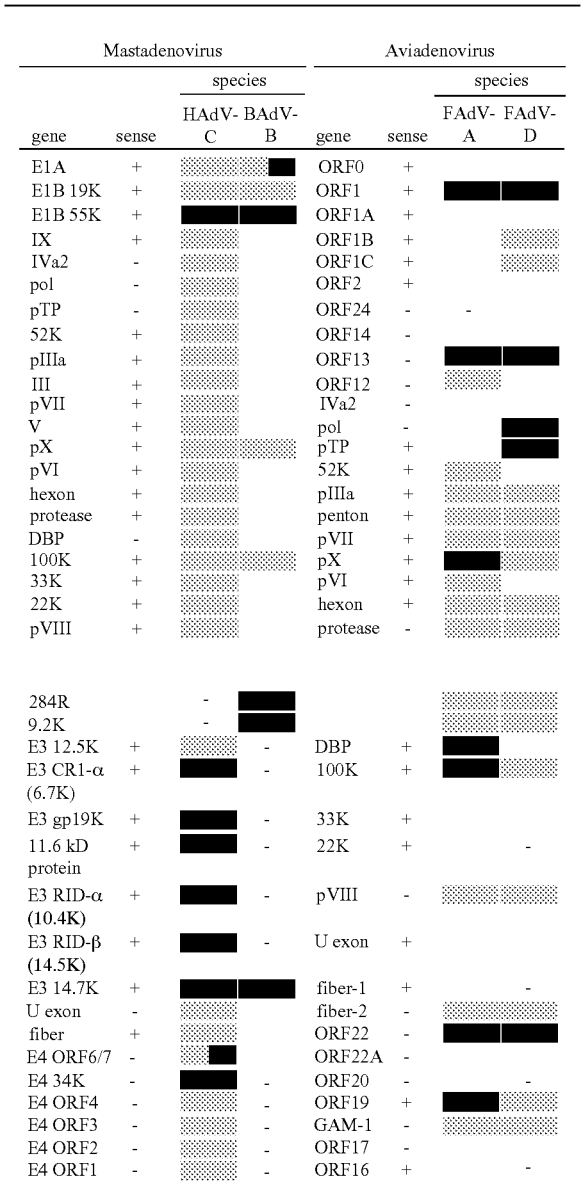

| | Mastadenovirus species | | | Aviadenovirus species | | |
|---|---|---|---|---|---|---|
| gene | sense | HAdV-C | BAdV-B | gene | sense | FAdV-A | FAdV-D |
| E1A | + | | | ORF0 | + | | |
| E1B 19K | + | | | ORF1 | + | | |
| E1B 55K | + | | | ORF1A | + | | |
| IX | + | | | ORF1B | + | | |
| IVa2 | - | | | ORF1C | + | | |
| pol | - | | | ORF2 | + | | |
| pTP | - | | | ORF24 | - | - | |
| 52K | + | | | ORF14 | - | | |
| pIIIa | + | | | ORF13 | - | | |
| III | + | | | ORF12 | - | | |
| pVII | + | | | IVa2 | - | | |
| V | + | | | pol | - | | |
| pX | + | | | pTP | + | | |
| pVI | + | | | 52K | + | | |
| hexon | + | | | pIIIa | + | | |
| protease | + | | | penton | + | | |
| DBP | - | | | pVII | + | | |
| 100K | + | | | pX | + | | |
| 33K | + | | | pVI | + | | |
| 22K | + | | | hexon | + | | |
| pVIII | + | | | protease | - | | |
| 284R | - | | | | | | |
| 9.2K | - | | | | | | |
| E3 12.5K | + | | - | DBP | + | | |
| E3 CR1-α (6.7K) | + | | - | 100K | + | | |
| E3 gp19K | + | | - | 33K | + | | |
| 11.6 kD protein | + | | - | 22K | + | - | |
| E3 RID-α (10.4K) | + | | - | pVIII | - | | |
| E3 RID-β (14.5K) | + | | - | U exon | + | | |
| E3 14.7K | + | | - | fiber-1 | + | - | |
| U exon | - | | | fiber-2 | - | | |
| fiber | + | | | ORF22 | + | | |
| E4 ORF6/7 | - | | | ORF22A | - | | |
| E4 34K | - | | - | ORF20 | - | - | |
| E4 ORF4 | - | | - | ORF19 | + | | |
| E4 ORF3 | - | | - | GAM-1 | - | | |
| E4 ORF2 | - | | - | ORF17 | - | | |
| E4 ORF1 | - | | - | ORF16 | + | - | |

TABLE 3-continued

| | | | | | |
|---|---|---|---|---|---|
| BAdV E4 ORF1 | - | - | ORF9 | + | - |
| BAdV E4ORF2 | - | - | ORF10 | + | - |
| BAdV E4ORF3 | - | - | ORF11 | + | |
| BAdV E4ORF4 | - | - | ORF23 | - | - |
| BAdV E4ORF5 | - | - | ORF25 | + | - |
| | | | ORF26 | + | - |

The absence or occurrence of one or more upstream ORFs (uORFs) within the 5'-UTR of each mRNA is indicated. Transcript sequences were reconstituted in silica based on the experimentally determined splice donor and acceptor sites that are reported for FAdV-1 (Payet et al., 1998), FAdV-9 (Ojkic et al., 2002), HAdV-2 (Broker, 1984; Perricaudet, M., Akusjarvi, G., Virtanen, A. & Pettersson, U. (1979). Structure of 2 spliced messenger-rnas from the transforming region of human subgroup-c adenoviruses. Nature 281, 694-696; Virtanen, A., Gilardi, P., Naslund, A., Lemoullec, J. M., Pettersson, U. & Perricaudet, M. (1984). messenger-RNAs from human adenovirus-2 early region 4. J Viral 51, 822-831; Wold, W. S. M., Cladaras, C., Magie, S. C. & Yacoub, N. (1984). Mapping a new gene that encodes an 11,600-molecular-weight protein in the E3 transcription unit of adenovirus-2. J Viral 52, 307-313), and BAdV-3 (Idamakanti, N., Reddy, P. S., Babiuk, L. A. & Tikoo, S. K. (1999). Transcription mapping and characterization of 284R and 121R proteins produced from early region 3 of bovine adenovirus type 3. Virology 256, 351-359; Reddy et al., 1999; Reddy, P. S., Idamakanti, N., Zakhartchouk, A. N., Baxi, M. K., Lee, J. B., Pyne, C., Babiuk, L. A. & Tikoo, S. K. (1998). Nucleotide sequence, genome organization, and transcription map of bovine adenovirus type 3. J Viral 72, 1394-1402; Zheng et al., 1999). Fields showing two colours indicate that transcripts encoding this gene have been detected with and without a uORF(s). A detailed list of the FAdV uORFs is provided as Table 2.

Reliable interpretation of genome deletions is important for vaccine vector design and functional studies. Further, uORF-dependent translational regulation of the as-yet-undetermined virulence factors of FAdVs may play a role in FAdV pathogenesis, including FAdV-4-associated IBH/HPS.

Example 2

Pathogenicity Studies for FAdV-4 ON1 a) Experimental Design

A trial in white Leghorn specific pathogen free (SPF) chickens was conducted to assess the pathogenic potential of the virus. Briefly, 10-day old chicks were inoculated intramuscularly (im) or orally, with $2 \times 10^8$ plaque forming units (pfu) of the virus. The control birds received PBS. All chickens were re-inoculated at 14 days of age with the same dose of virus. The birds were observed daily (3×) for clinical signs and drown randomly for necropsy at each 0, 3, 5, 7, 14, 21, 28 days post-infection (d.p.i.). The chickens were euthanized, necropsied, examined for the presence of gross lesions and tissues from liver, bursa of Fabricius and cecal tonsils (ct) were collected. Cloacal swabs were taken from all birds at 0, 3, 5, 10, 14, 21, 28 d.p.i. and their virus titers were determined in CH-SAH cells. In addition, chickens were bled at weekly intervals 0, 7, 14, 21, 28 d.p.i. and serum samples were tested for FAdV-specific antibodies (Abs) by enzyme-linked immunosorbent assay (ELISA).

b) Pathogenicity of FAdV-4 ON1: Clinical Signs, Gross Lesions and Histology

Clinical signs or pathologic changes of inclusion body hepatitis were not seen in groups of chicks after intramuscular or oral administration of virus. The classical signs of IBH characterized by intranuclear inclusion bodies in hepatocytes were not present in any of the inoculated chickens.

c) Quantitative Real Time PCR (qPCR) Analysis (to Determine Viral Load in Organs)

To determine the viral load in tissues, real time PCR using Syber Green as intercalating dye was developed. The FAdV-4 ORF14 gene was used as an indicator for the presence of viral DNA with primers; forward primer: 5'-AGTGTGTATGT-GCGTTGGGTAG-3' (SED ID NO: 66) and reverse primer: 5'-CATTGTCATAAC GATGGTGTAG-3' (SED ID NO: 67). The 20 μl qPCR reaction containing 1 μl (10 pmol) of each primer, 10 μl of QuantiTec SYBR Green I PCR Master Mix (Qiagen), 2 μl DNA and 6 μl nuclease free water, was prepared using the computerized automated liquid handling robotics CAS-1200 (Corbett Research). The qPCR program was first run at 15 min at 95° C. to activate the Taq polymerase, followed by 40 cycles of 95° C. for 20 sec, 57° C. for 15 sec, 72° C. for 20 sec, with an acquiring step at 75° C. for 15 sec, using the Corbett Research Rotor-Gene 6000 System. Quantitative measurement of the PCR product was carried out by incorporation of the SYBR Green I fluorescent dye. To establish the standard curves, 10-fold serial dilutions ($10^{-1}$ to $10^{-7}$) of FAdV-8 genomic DNA starting at 12.2 ng/μl ($2.4 \times 10^8$ copies/μl) were made and used as qPCR templates. Melting curve analysis was performed after each run to monitor the specificity of the PCR products. Negative control using DNA extracted from uninfected chicken and no template control (NTC) were routinely included in each experiment.

d) Statistical Analysis

Kruskal-Wallis test was performed to evaluate whether viral copy numbers differed among tissues. Following statistically significant P-value, pair-wise comparison was performed between different tissues. P-values of 0.05 were considered to be statistically significant.

e) Replication of FAdV-4 ON1

A pathogenicity study in specific pathogen free (SPF) chickens was performed. There were no clinical signs in any of the chickens inoculated either orally or intramuscularly inoculated. A very high amount ($2 \times 10^8$ plaque forming unit/chicken) of virus was used for the inoculation of 10-day-old chickens. Tissues were collected from euthanized birds at different times post-inoculation for histopathological evaluation; no lesions were found in any of the analyzed tissues: liver, bursa of Fabricius, cecal tonsils.

Quantitative real-time PCR was employed to establish viral genome copy numbers in liver, bursa of Fabricius and cecal tonsil of birds infected either orally or intramuscularly (im) with strain FAdV-4 ON1. No viral DNA was detected in any tissues from any chicken in trial before inoculation and in mock-infected chickens. The results are summarized in FIG. 9.

The virus and each inoculation group (oral and intramuscular) were subjected separately to the Kruskal-Wallis test to evaluate differences in number of viral copies among tissues. The cecal tonsil was the organ with the highest number of viral copies, followed by liver and then bursa, irrespective of inoculation route in both groups. At group level, for FAdV-4 orally-inoculated birds there were significant differences ($P<0.001$) in number of viral copies whereas for the im group, the differences tended to be significant ($P=0.06$).

For orally inoculated birds, cecal tonsil viral copy number was higher than viral copy number in liver ($P=0.0207$), and bursa ($P=0.0001$), whereas viral copy numbers in liver ranked only marginally higher than viral copy numbers in bursa ($P=0.0759$).

For im inoculated birds, only cecal tonsil viral copy number was higher that viral copy number in bursa ($P=0.0154$), whereas difference among other organs were not significant ($P>025$).

f) Virus Titers in the Feces of Chickens Inoculated Orally or Intramuscularly with FAdV-4 ON1

No virus was present in cloacal swabs in any groups of chickens before inoculation and in the mock infected group at all time (FIG. 10). The results showed that the difference in titers between chickens inoculated orally and im was statistically significant ($P<0.001$) when it was tested 2-sample Wilcoxon test. The oral group had higher ranks. The highest virus titer in the orally inoculated group was found at day 3 post-infection (p.i.) and 5 p.i. Chickens shed the virus through the entire study period in both oral and im group.

g) Antibody (Ab) Response to Viral Proteins in Chickens Inoculated with FAdV-4 ON1

The immune response was studied by determining the antibody titers by ELISA in serum samples. Abs against FAdV-4 were not detected in any chick used in trial before inoculation (0 d.p.i.) and in the mock-infected group at all times (FIG. 11). Ab response to viral proteins appeared at 7 d.p.i. with significant differences between inoculated groups and negative control. The difference in titer between FAdV-4 and control chickens were statistically significant over the entire period ($P<0.001$). Titers of inoculated chickens were higher.

The difference in titers between groups inoculated im and orally were significant ($P<0.001$) when tested by ELISA using FAdV-4 as antigen (ELISA-4). Chickens inoculated im had higher titer than chickens inoculated orally.

Similarly, the difference in titers between FAdV-4 inoculated im and orally were significant ($P=0.004$) when tested by ELISA using FAdV-9 as antigen (ELISA-9). Chickens inoculated im had higher titers than chickens inoculated orally.

When both im and orally inoculated chickens were considered together, and titers from ELISA-4 and ELISA-9 were compared, the difference in titres was significant ($P<0.001$). ELISA titers with homologous virus were higher.

Similarly ELISA-4 and ELISA-9 yielded different OD when only orally inoculated animals were considered ($P<0.001$). Homologous virus yielded higher titers, proving hypothesis that heterologous virus can be used to detect the presence of adenovirus Abs in general.

A stronger immune response (FIG. 11) was induced by intramuscular administration compared to oral administration.

The present invention should not be interpreted only in the light of the examples, as several modifications thereto are possible, such as the exogenous nucleotide sequence inserted in the viral vector. Therefore, the present invention shall not be construed as limited except for the prior art teachings and for the appended claims.

All publications, patents and patent applications are herein incorporated by reference in their entirety to the same extent as if each individual publication, patent or patent application was specifically and individually indicated to be incorporated by reference in its entirety.

The invention claimed is:

1. A non-pathogenic fowl adenovirus serotype 4 viral vector comprising a nucleotide sequence with at least 95% sequence identity to SEQ ID NO: 2 and an exogenous nucleotide sequence coding for a polypeptide of interest.

2. The viral vector of claim 1, comprising a nucleotide sequence with at least 98% sequence identity to SEQ ID NO: 2.

3. The viral vector of claim 1, comprising the nucleotide sequence of SEQ ID NO: 2.

4. The viral vector of claim 1 comprising an exogenous nucleotide sequence coding for at least one antigenic site of a disease of concern.

5. The viral vector of claim 4, wherein the exogenous nucleotide sequence is selected from antigenic sites sequences against influenza, infectious laryngotracheitis, infectious bronchitis, bursa of Fabricius' infection (Gumboro), hepatitis, viral rhinotracheitis, infectious coryza, *Mycoplasma hyopneumonieae*, pasteurellosis, Porcine Respiratory and Reproductive Syndrome (PRRS), circovirus, bordetellosis, parainfluenza, or any other antigen which size allows its insertion into the corresponding viral vector.

6. The viral vector of claim 1, wherein the exogenous nucleotide sequence is operably linked to a control sequence, optionally a promoter sequence.

7. A host cell comprising the viral vector of claim 1.

8. A method for producing the viral vector of claim 1, comprising the steps of:
   a) optionally amplifying the exogenous nucleotide sequence of interest;
   b) inserting the exogenous nucleotide sequence of interest in the viral vector; and,
   c) introducing the infectious clone thus produced into a suitable cell line.

9. The method of claim 8, wherein the exogenous nucleotide sequence of interest is selected from antigenic sites sequences against influenza, infectious laryngotracheitis, infectious bronchitis, bursa of Fabricius' infection (Gumboro), hepatitis, viral rhinotracheitis, infectious coryza, *Mycoplasma hyopneumonieae*, pasteurellosis, Porcine Respiratory and Reproductive Syndrome (PRRS), circovirus, bordetellosis, parainfluenza, or any other antigen which size allows its insertion into the corresponding viral vector.

10. An immunogenic composition comprising at least a viral vector of claim 1 obtained from the fowl adenovirus with nucleotide sequence SEQ ID NO:2 with an exogenous nucleotide sequence coding for at least one antigenic site of a disease of concern inserted therein.

11. The immunogenic composition of claim 10, further comprising a pharmaceutically acceptable carrier.

12. The fowl adenovirus of claim 1, wherein the fowl adenovirus is capable of reaching a viral titer of at least 3 $\log_{10}$ in CH-SAH cells 3 days after infection with the fowl adenovirus at a multiplicity of infection (m.o.i) of 5 for one hour at room temperature.

* * * * *